US008158832B2

(12) United States Patent
Carroll et al.

(10) Patent No.: US 8,158,832 B2
(45) Date of Patent: Apr. 17, 2012

(54) PHOTOCHEMICAL METHODS AND PHOTOACTIVE COMPOUNDS FOR MODIFYING SURFACES

(75) Inventors: Gregory T. Carroll, New York, NY (US); Denong Wang, Palo Alto, CA (US); Nicholas J. Turro, New York, NY (US); Jeffrey T. Koberstein, Storrs, CT (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1498 days.

(21) Appl. No.: 11/595,292

(22) Filed: Nov. 9, 2006

(65) Prior Publication Data

US 2010/0099580 A1 Apr. 22, 2010

Related U.S. Application Data

(60) Provisional application No. 60/735,402, filed on Nov. 9, 2005, provisional application No. 60/776,096, filed on Feb. 23, 2006.

(51) Int. Cl.
*C07C 49/303* (2006.01)
(52) U.S. Cl. ........................................ 568/332
(58) Field of Classification Search .................. 568/332
See application file for complete search history.

(56) References Cited

U.S. PATENT DOCUMENTS

| | | | |
|---|---|---|---|
| 5,120,569 | A | 6/1992 | Zupancic et al. |
| 5,370,974 | A | 12/1994 | Agostino et al. |
| 6,368,838 | B1 | 4/2002 | Singhvi et al. |
| 2003/0228637 | A1 | 12/2003 | Wang |
| 2004/0025268 | A1 | 2/2004 | Porat et al. |
| 2004/0033546 | A1 | 2/2004 | Wang |
| 2004/0106886 | A1 | 6/2004 | Verdonk et al. |
| 2004/0249186 | A1 | 12/2004 | Balzer et al. |
| 2004/0253634 | A1 | 12/2004 | Wang |
| 2005/0080213 | A1 | 4/2005 | Meyer et al. |
| 2005/0112292 | A1 | 5/2005 | Parker et al. |

FOREIGN PATENT DOCUMENTS

WO WO-02/064556 A2 8/2002

OTHER PUBLICATIONS

Shoji, et al. Document No. 141:380733 retrieved from CAPLUS on Dec. 29, 2010.*
Wu, et al. Document No. 137:185881 retrieved from CAPLUS on Dec. 29, 2010.*
Nagai, et al. Document No. 134:223720 retrieved from CAPLUS on Dec. 29, 2010.*
Fuerstner, et al. Document No. 125:58472 retrieved from CAPLUS on Dec. 29, 2010.*
Fuerstner, et al. Document No. 123:227347 retrieved from CAPLUS on Dec. 29, 2010.*
Morinaga, et al. Document No. 91:141668 retrieved from CAPLUS on Dec. 29, 2010.*
Willson, et al. Document No. 120:26125 retrieved from CAPLUS on Dec. 29, 2010.*
Becker, et al. Document No. 114:246519 retrieved from CAPLUS on Dec. 29, 2010.*
Gruetzmacher, et al. Document No. 112:54548 retrieved from CAPLUS on Dec. 29, 2010.*
Ito, et al. Document No. 110:56843 retrieved from CAPLUS on Dec. 29, 2010.*
Kempter, et al. Document No. 87:184455, retrieved from CAPLUS on Dec. 29, 2010.*
Pacifici, et al. Document No. 87:153560, retrieved from CAPLUS on Dec. 29, 2010.*
Andrews, et al. Document 85:6112 retrieved from CAPLUS on Dec. 29, 2010.*
Fuson, et al. Document 55:105676 retrieved from CAPLUS on Dec. 29, 2010.*
Havens, et al. Document 54:4418 retrieved from CAPLUS on Dec. 29, 2010.*
Rosen. Document 87:6660 retrieved from CAPLUS on Dec. 29, 2010.*
Pitts, J.D. et al., "New Photoactivators for Multiphoton Excited Three-dimensional Submicron Cross-linking of Proteins: Bovine Serum Albumin and Type 1 Collegen," Photochemistry and Photobiology, 2002, 76(2): 135-144.
Lee, M. et al. "Facile Preparation of Carbohydrate Microarrays by Site-Specific, Covalent Immobilization of Unmodified Carbohydrates on Hydrazide-Coated Glass Slides," Organic Letters, 2005, vol. 7, No. 19, 4269-4272.
Gan, D. et al., "Thin-Film Morphologies of Random Copolymers as Functions of Thermal History," Journal of Colloid and Interface Science 239, 272-277 (2001).
Allen, C.F.H. et al., "Use Potassium Phthalimide for Identification of Alkylene Bis Halides and Bis Sulfonates," Analytical Chemistry, vol. 44, No. 9, Aug. 1972, 1694-1696.
Schmelmer, U. et al., "Surface-Initiated Polymerization of Self-Assembled Monolayers: Amplification of Patterns on the Micrometer and Nanometer Scale," Angew. Chem. Int. Ed. 2003, 42, No. 5, pp. 559-563.
International Search Report and Written Opinion issued for corresponding International Patent Application No. PCT/US2006/043614.
Andrews et al., "Photopolymerization via the paterno-Buechi reaction. II. reaction of aromatic diketones with furans," Journal of polymer Science, Polymer Chemistry Edition, Interscience publishers, New York, NY. vol. 14, pp. 331-341 (1976).
Becker et al., "Ions derives from dianthrylethane species. How to mode of linking affects the intramolecular electron transfer," Journal of the american chemical society, vol. 113, pp. 1121-1127 (Feb. 1991).

(Continued)

*Primary Examiner* — Shawquia Young
(74) *Attorney, Agent, or Firm* — Wilmer Cutler Pickering Hale and Dorr LLP

(57) ABSTRACT

Compounds and methods for controlling the surface properties are described. Compounds of the invention can form radicals upon exposure to irradiation, which can then react with nearby molecules to alter the surface properties of various substrates. The invention can provide surfaces that are resistant to dewetting, surfaces that have immobilized molecules such as carbohydrates and polymers immobilized, and surfaces that have metals deposited on the surface. The invention can be utilized in a wide range of application, such as sensors, microreactors, microarrays, electroless deposition of metals, and the like.

1 Claim, 41 Drawing Sheets

OTHER PUBLICATIONS

Database Beilstein, Beilstein Institute for organic Chemistry, XP 002587789, Frankfurt, Chemische Berichte, vol. 62, pp. 1410 (1929).
Database Beilstein, Beilstein institute for organic chemistry, XP 002587785, Chemische Berichte, vol. 122, pp. 2291-2298 (1989).
Database Beilstein, Beilstein Institute for organic Chemistry, XP 002587790, Frankfurt, JACS, vol. 74, pp. 1621 (1952).
Database Beilstein, Beilstein Institute for Organic Chemistry, XP 002587787, Journal fur praktische Chemi, vol. 319, pp. 589-600 (1977).
Extended Search Report mailed on Jul. 26, 2010 for European patent Application No. 06851911.5 filed Nov. 9, 2006.
Fuerstner et al., High-surface sodium as a reducing agent for TiCl3<' Synthesis, Georg Thieme Verlag, Stuttgart, pp. 63-68 (Jan. 1995).
Fuerstner et al., "Syntheses, structures, and complexation properties of photoresponsive crownophanes," Liebigs annalen: Organic and Bioorganic Chemistry, VCH Publisher, pp. 655-662 (May 1, 1996).
Ito et al., "Photochemistry of bichromophoric aromatic diketones: the effects of methylene chain," Journal of Organic Chemistry, American Chemical society, Eaton, vol. 54, pp. 506-509 (Jan. 1989).
Pitts et al., "New Photoactivators for multiphoton excited three-dimensional submicron Cross-linking of proteins: Bovine Serum Albumin and Type 1 Collagen," Photochemistry and photobiology, vol. 76, pp. 135-144 (2002).
Angeloni, S. et al. "Glycoprofiling with micro-arrays of glycoconjugates and lectins." Glycobiology, 15:31-41. (2005).
Blawas, A. S. & W. M. Reichert, Biomaterials, 19:595-609. (1998).
Blixt, O. et al. "Printed covalent glycan array for ligand profiling of diverse glycan binding proteins." PNAS USA, 101(49):17033-17038. (2004).
Borman, Stu, "Antibody Could Lead to Anthrax Test." Chemical & Engineering News. (Aug. 23, 2006).
Bryan, M. C. et al. "High-throughput identification of fucosyltransferase inhibitors using carbohydrate micoarrays." Bioorg. Med. Chem. Lett., 14:3185-3188. (2004).
Carroll, Gregory et al. "Photochemical Micropatterning of Carbohydrates on a Surface." Langmuir, 22:2899-2905. (2006).
Carroll, Gregory T. et al. "Photoactive Additives for Cross-Linking Polymer Films: Inhibition of Dewetting in Thin Polymer Films." Langmuir, 22:7748-7754. (2006).
Chen, C. S. et al. "Geometric control of cell life and death." Science, 276:1425-1428. (1997).
Constans, Aileen, "High-Carb Science with Sugarcoated Arrays." The Scientist, p. 33. (Nov. 8, 2004).
De Smet et al. "Covalently attached saccharides on silicon surfaces." J. Am. Chem. Soc., 125:13916-13917. (2003).
Disney, Matthew D. and Peter H. Seeberger, "The use of carbohydrate microarrays to study carbohydrate-cell interactions and to detect pathogens." Chem. Biol., 11:1701-1707. (2004).
Fazio, F. et al. "Synthesis of Sugar Arrays in Microtiter Plate." J. Am. Chem. Soc., 124:14397-14402. (2002).
Fodor, S. P. A. et al. "Light-directed, spatially addressable parallel chemical synthesis." Science, 251:767-773. (1991).
Fukui, S. et al. "Oligosaccharide microarrays for high-throughput detection and specificity assignments of carbohydrate-protein interactions." Nature Biotechnol., 20:1011-1017. (2002).
Husemann, M. et al., "Manipulation of Surface Properties by Patterning of Covalently Bound Polymer Brushes." J. Am. Chem. Soc., 122, 1844-1845. (2000).

Jelinek, R. and S. Kolusheva, "Carbohydrate Biosensors." Chem. Rev., 104:5987-6015. (2004).
Kanaoka, Y. "Photoreactions of cyclic imides. Examples of synthetic organic photochemistry." Acc. Chem. Res., 11:407-413. (1978).
Langer, R. and J. P. Vacanti, "Tissue engineering." Science, 260:920-926. (1993).
Lee, K. et al. "Photolithographic Technique for Direct Photochemical Modification and Chemical Micropatterning of Surfaces." Langmuir, 20, 1812-1818. (2004).
Liu, G. Y. and N. A. Amro, "Positioning protein molecules on surfaces: a nanoengineering approach to supramolecular chemistry." Proc. Natl. Acad. Sci. USA, 99(8):5165-5170. (2002).
Lopez, G. P. et al. "Imaging of features on surfaces by condensation figures." Science, 260:647-649. (1993).
Moon, J. H. et al. "Formation of Uniform Aminosilane Thin Layers: An Imine Formation to Measure Relative Surface Density of the Amine Group." Langmuir, 12:4621-4624. (1996).
Nimrichter, L. et al. "Intact cell adhesion to glycan microarrays." Glycobiology, 14(2):197-203. (2004).
Park, S. and I. Shin, "Fabrication of carbohydrate chips for studying protein-carbohydrate interactions." Angew. Chem. Int. Ed. Engl., 41(17):3180-3182. (2002).
Park, S. et al. "Carbohydrate chips for studying high-throughput carbohydrate-protein interactions." J. Am. Chem. Soc., 126:4812-4819. (2004).
Pirrung, M. C., "How to make a DNA chip." Angewandte Chemie, International Edition, 41:1276-1289. (2002).
Prucker, O. et al. "Photochemical Attachment of Polymer Films to Solid Surfaces via Monolayers of Benzophenone Derivatives." J. Am. Chem. Soc., 121:8766-8770. (1999).
Ratner, Daniel et al. "Probing Protein—Carbohydrate Interactions with Microarrays of Synthetic Oligosaccharides." Chem Bio Chem, 5:379-383. (2004).
Rozsnyai, L. F. et al. "Photolithographic immobilization of biopolymers on solid supports." Angew. Chem., 31(6):759-761. (1992).
Shin, I., et al. "Carbohydrate microarrays: An advanced technology for functional studies of glycans." Chem. Eur. J., 11:2894-2901. (2005).
Takahashi, S. and J. Anzai. "Phenylboronic acid monolayer-modified electrodes sensitive to sugars." Langmuir, 21:5102-5107. (2005).
Tamborrini, Marco et al. "Anti-Carbohydrate Antibodies for the Detection of Anthrax Spores." Agnew. Chem. Int. Ed., 45:1-3. (2006).
Turro, N. J. "Modern Molecular Photochemistry." University Science Books, Sausalito, CA. (1991).
Wang, D. et al. "Carbohydrate microarrays for the recognition of cross-reactive molecular markers of microbes and host cells." Nature Biotechnol., 20:275-281. (2002).
Whitesides, G. M. et al. "Soft lithography in biology and biochemistry." Annu. Rev. Biomed. Eng., 3:335-373. (2001).
Willats, William G. T. et al. "Sugar-coated microarrays: a novel slide surface for the high-throughput analysis of glycans." Proteomics, 2:1666-1671. (2002).
Yeong, W. Y. et al. "Rapid protyping in tissue engineering: challenges and potential." Trends Biotechnol., 22(12), 643-652. (2004).

* cited by examiner

| 5 X 5 um AFM Images |  | | | |
|---|---|---|---|---|
| % BP | 0% | .006% | .03% | .07% |
| Ave Roughness (nm) | 1.9±.5 | 1.8±.4 | 1.0±.4 | .31±.04 |
| Ave Height (nm) | 7±2 | 6±1 | 4±1 | 2.3±.1 |

Poly (vinyl alcohol) photografted onto Phthalmide SAM Samples rinsed with heated water (95 C).

PHOTOCHEMICAL METHODS AND PHOTOACTIVE COMPOUNDS FOR MODIFYING SURFACES

CROSS-REFERENCE TO RELATED APPLICATIONS

The present application claims the benefit of the filing dates of U.S. Provisional Application No. 60/735,402, filed on Nov. 9, 2005, and U.S. Provisional Application No. 60/776,096, filed on Feb. 23, 2006, both of which are incorporated by reference herein in their entireties.

STATEMENT REGARDING FEDERALLY SPONSORED RESEARCH OR DEVELOPMENT

Work described herein may have been supported by, or in part by, U.S. Army Research Laboratory and the U.S. Army Research Office under contract/grant number DA W911NF-04-1-0282 and in part by the National Science Foundation under grant numbers DMR-02-14263, IGERT-02-21589, CHE-04-15516, and RF CUNY #404340001A. The U.S. Government may have certain rights in the invention.

INCORPORATION BY REFERENCE

The disclosures of all patents and publications referenced in this application are hereby incorporated by reference into this application in their entireties in order to more fully describe the state of the art as known to those skilled therein as of the date of the invention described and claimed herein.

COPYRIGHT NOTICE

The disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

In many applications, control of the surface properties is important. For example, controlling the dewetting properties of thin polymer films on an organic or inorganic substrate are important in numerous applications such as sensors, coatings, adhesives, resist layers, lubricating surfaces, and microelectronics. A smooth surface is thought to be wetted by an adsorbed species when van der Waals interactions at the substrate-liquid, liquid-air, and substrate-air interfaces allow the liquid to spread on the surface such that the contact angle is zero or very close to zero. When a thin film is cast on a nonwettable surface for which the interfacial tensions do not favor wetting, dewetting can occur, a process in which the film retracts from the surface, typically forming holes.

Currently, thin amorphous polymer films, such as polystyrene films, are applied to a surface and vitrified to stabilize the film. However, such glassy films are metastable and can spontaneously dewet when exposed to a solvent vapor or heated above the glass transition temperature. Such dewetting of films after exposure to solvent vapor is a current problem in developing sensors to detect nerve agents.

Control of surface properties can also enable new fields of study. For example, glycomics (a field that explores the information content of carbohydrates) has emerged recently. Patterning a surface with carbohydrate microarrays can allow investigation of carbohydrate interactions with viruses, enzymes, cells, antibodies, proteins and the like. However, most current methods for generating carbohydrate microarrays involve either a noncovalent immobilization that becomes less stable as the molecular weight of the carbohydrate decreases, or synthetic methods in which each carbohydrate to be spotted must first be chemically modified.

Accordingly, improved control of surface properties is currently needed to improve various applications, such as sensors, coatings, adhesives, resist layers, lubricating surfaces, microelectronics, etc., and to enable new applications.

SUMMARY OF THE INVENTION

In some aspects, the invention provides photoactive compounds of formula (I):

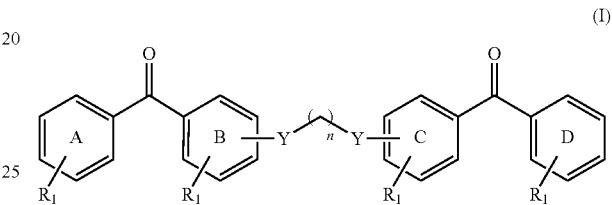

wherein each of the rings A-D can independently be substituted with one or more $R_1$ groups and n can be any integer from 1 to 1000 (e.g., 1 to 10, such as 2). In formula (I), $R_1$ can independently be a hydrogen, a halogen, a hydroxyl, an aryl, an amide, a cyano, a substituted or unsubstituted straight- or branched-chain alkyl containing, for example, 1 to 6 carbons, a substituted or unsubstituted alkene containing, for example, 2 to 4 carbons, —C(O)$R^3$, —CO$_2$$R^3$, —OC(O)$R^3$, —O$R^3$, or —OC(O)$R^5$. Each $R^3$ can independently be a hydrogen, a substituted or unsubstituted $C_1$-$C_{10}$ straight-chain or branched-chain alkyl, or a substituted or unsubstituted alkene. Each $R^5$ can independently be a hydrogen, an unsubstituted straight- or branched-chain alkyl which contains 1-6 carbons, or a straight- or branched-chain alkyl which contains 1-6 carbons and is substituted by an alkyne. Y can independently be —CH$_2$—, —C(O)—, —OC(O)—, —C(O)O—, —C(O)N$R^3$—, or —N$R^3$C(O)—.

In other aspects, the invention provides photoactive compounds of formula (II):

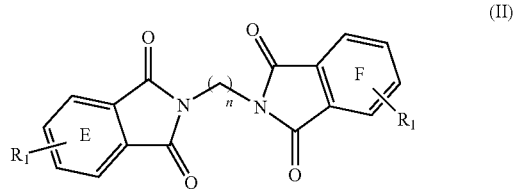

wherein each of the rings E and F can independently be substituted with one or more $R_1$ groups and n can be any integer from 1 to 1000 (e.g., 1 to 10, such as 2). In formula (II), $R_1$ can independently be a hydrogen, a halogen, a hydroxyl, an aryl, an amide, a cyano, a substituted or unsubstituted straight- or branched-chain alkyl containing, for example, 1 to 6 carbons, a substituted or unsubstituted alkene containing, for example, 2 to 4 carbons, —C(O)$R^3$, —CO$_2$$R^3$, —OC(O)$R^3$, —O$R^3$, or —OC(O)$R^5$. Each $R^3$ can independently be a hydrogen, a substituted or unsubstituted $C_1$-$C_{10}$ straight-chain or branched-chain alkyl, or a substituted or unsubstituted alkene. Each $R^5$ can independently be a hydrogen, an unsubstituted straight- or branched-chain alkyl which contains 1-6 carbons, or a straight- or branched-chain alkyl which contains 1-6 carbons and is substituted by an alkyne.

In other aspects, the invention provides photoactive compounds of formula (IV):

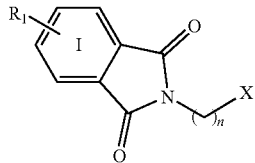

(IV)

wherein ring I can be substituted with one or more $R_1$ groups and n can be any suitable integer from 1 to 100 (e.g., 1 to 20, such as 11). In formula (IV), X can be $R^2$, —$CO_2R^3$, —$C(O)NR^3R^3$, —$SR^4$, —CN, —$OR^3$, a halogen, a β-diketone, a silane, a phosphate, a phosphonate, a polymer, or block copolymer. In some embodiments, X can be bound to a surface. $R_1$ can independently be a hydrogen, a halogen, a hydroxyl, an aryl, an amide, a cyano, —$R^2$, —$C(O)R^3$, —$CO_2R^3$, —$OC(O)R^3$, or —$OR^3$. Each $R^2$ can independently be hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —$OC(O)R^5$, wherein $R^5$ can independently be a hydrogen, an unsubstituted straight- or branched-chain alkyl which contains 1-6 carbons, or a straight- or branched-chain alkyl which contains 1-6 carbons and is substituted by an alkyne. Each $R^3$ can independently be a hydrogen, a substituted or unsubstituted $C_1$-$C_{10}$ straight-chain or branched-chain alkyl, or a substituted or unsubstituted alkene. Each $R^4$ can independently be hydrogen, —S-pyridyl, —$SR^3$, —$SO_2R^3$, or —$SR^8$, wherein the —$SR^8$ and the rest of formula (IV) can combine to form a bis-disulfide.

In one aspect, the invention provides methods for forming a non-dewetting cross-linked polymer film on a surface. Methods of the invention can include adding to a polymer film on a surface a compound of formula (I) or formula (II), and irradiating the compound to form a cross-linked polymer film. Alternatively, the method can include coating a surface with a composition that includes a compound of formula (I) or (II), and irradiating the composition to form a cross-linked polymer film. The cross-linked polymer film can be resistant to dewetting from the surface even after heating above the glass transition temperature or melting temperature of the polymer, or even after exposure to solvents. In some embodiments, irradiation of the polymer film may be through a photomask, resulting in a patterned array of cross-links.

In another aspect, the invention provides methods for immobilizing molecules on a surface. The method can include immobilizing a compound of formula (IV) on a surface; applying a molecule to be immobilized; and irradiating the compound. A photochemical reaction between the molecule and the compound can result in covalent links between the molecule and the compound and the compound can be immobilized on the surface. In some embodiments, the irradiation of the compound may be through a photomask. In other embodiments, the molecule may be a carbohydrate or a polymer. In some other embodiments, the invention also provides carbohydrate microarrays formed by the methods of the invention.

In yet another aspect, the invention provides arrays on a surface that includes a compound of formula (IV) immobilized on the surface and at least one molecule covalently attached to the compound of formula (IV). In some embodiments, the molecule covalently attached to the compound can be a carbohydrate, a polymer, a DNA, an RNA, a protein, a peptide, and the like.

DETAILED DESCRIPTION OF THE INVENTION

Figure 1:
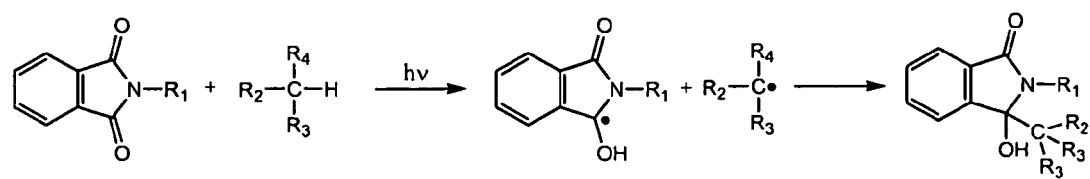
FIG. 1 shows a schematic of a photoactive compound of the invention undergoing a photochemical hydrogen abstraction reaction followed by recombination to form a covalent bond.

For the purposes of promoting an understanding of the principles of the invention, reference will now be made to specific embodiments. It will nevertheless be understood that no limitation of the scope of the invention is thereby intended. Alteration and further modifications of the invention, and further applications of the principles of the invention as illustrated herein, as would normally occur to one skilled in the art to which the invention relates, are also within the scope of the invention.

DEFINITIONS

At the outset, certain terms described in this application are defined below.

The term "alkyl" as used herein refers to a substituted or unsubstituted aliphatic hydrocarbon chain and includes, but is not limited to, straight and branched chains containing from 1 to 12 carbon atoms, or in some instances, from 1 to 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted.

The term "amide" refers to (—CONR$^9$R$^{10}$), wherein R$^9$ and R$^{10}$ are independently hydrogen or alkyl.

The term "aryl" as used herein refers to an aromatic hydrocarbon or heterocycle. The aromatic hydrocarbon or heterocycle can contain from 3 to 10 atoms in certain embodiments. For example, an aromatic hydrocarbon encompasses phenyl or naphthyl, and an aromatic heterocycle encompasses pyridyl, pyrrole, thiophene, furan, diazoles, thiazoles, oxazoles, and imidazoles.

The term "carbonyl" refers to —C(O)—.

The term "β-diketone" refers to —COCH$_2$C(O)R$^7$ wherein R$^7$ is alkyl.

The term "ether" refers to —OR$^6$, wherein R$^6$ is a straight- or branched-chain alkyl containing from 1 to 6 carbons or a substituted or unsubstituted aryl.

The term "ester" refers to —C(O)OR$^7$ wherein R$^7$ is alkyl.

The term "halogen" refers to bromine, chlorine, fluorine, and iodine.

The term "phosphate" refers to —PO$_4$H$_m$ and its salts, wherein m is 0-3, having a charge of 0, −1, or −2.

The term "phosphonate" refers to —P(OR$^3$)$_3$, where R$^3$ can independently be a hydrogen, a substituted or unsubstituted C$_1$-C$_{10}$ straight-chain or branched-chain alkyl, or a substituted or unsubstituted alkene.

The term "silane" refers to a group comprising silicon to which at least one hydrolyzable group is bonded, such as —Si(OCH$_3$)$_3$, —Si(OCH$_2$CH$_3$)$_3$, —Si(Cl)$_3$, -silylimidazoles, -silylamines, and the like.

The term "carbohydrate" refers to a natural or synthetic monosaccharide, oligosaccharide, polysaccharide, or a glycoside thereof.

The term "glycoside" refers to a —O—, —N—, or —S— glycoside.

The term "oligosaccharide" refers to 1-20 monosaccharides covalently bonded together forming linear or branched structures, or structures which are a combination of both. Such structures include natural and synthetic disaccharides and branched- or straight-chain tri-, tetra-, penta-, hexa-, hepta-, octa-, nona-, and decasaccharides.

The term "mixed monolayer" refers to a monolayer or a multilayer containing at least two different types of molecules, such as phthalimides and amines.

The term "SAM" refers to a self-assembled monolayer.

COMPOUNDS OF THE INVENTION

Certain embodiments of the invention are directed to photoactive compounds that are capable of forming covalent bonds with nearby molecules after irradiation. In some embodiments, the invention provides photoactive compounds that may or may not be surface bound and that are capable of linking two molecules, such as polymers or small molecules.

In one or more aspects, the invention provides photoactive compounds of formula (I):

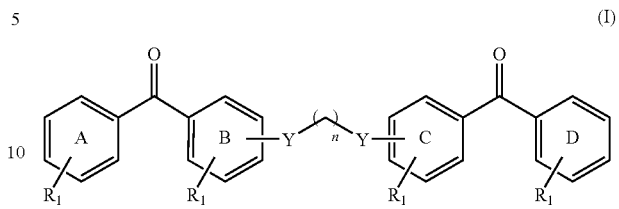

(I)

wherein each of the rings A-D can independently be substituted with one or more R$_1$ groups and n can be any integer from 1 to 1000 (e.g., 1 to 10, such as 2). In formula (I), R$_1$ can independently be a hydrogen, a halogen, a hydroxyl, an aryl, an amide, a cyano, a substituted or unsubstituted straight- or branched-chain alkyl containing, for example, 1 to 6 carbons, a substituted or unsubstituted alkene containing, for example, 2 to 4 carbons, —C(O)R$^3$, —CO$_2$R$^3$, —OC(O)R$^3$, —OR$^3$, or —OC(O)R$^5$. Each R$^3$ can independently be a hydrogen, a substituted or unsubstituted C$_1$-C$_{10}$ straight-chain or branched-chain alkyl, or a substituted or unsubstituted alkene. Each R$^5$ can independently be a hydrogen, an unsubstituted straight- or branched-chain alkyl which contains 1-6 carbons, or a straight- or branched-chain alkyl which contains 1-6 carbons and is substituted by an alkyne. Y can independently be —CH$_2$—, —C(O)—, —OC(O)—, —C(O)O—, —C(O)NR$^3$—, or —NR$^3$C(O)—. In one embodiment, one or more R$_1$ groups are at the meta and/or para positions of each of the rings A-D. Examples of compounds of formula (I) can include Compound 1 shown below and derivatives thereof:

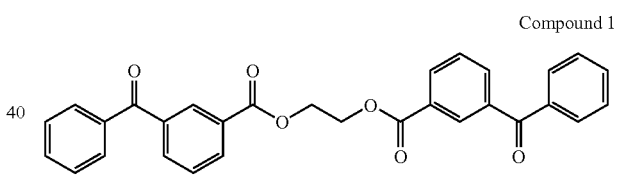

Compound 1

In other aspects, the invention provides photoactive compounds of formula (II):

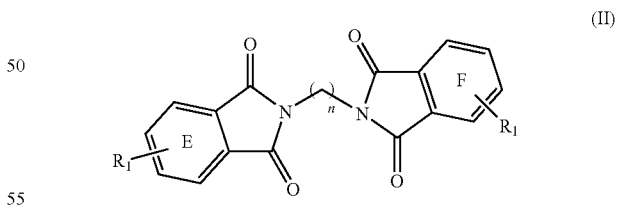

(II)

wherein each of the rings E and F can independently be substituted with one or more R$_1$ groups and n can be any integer from 1 to 1000 (e.g., 1 to 10, such as 2). In formula (II), R$_1$ can independently be a hydrogen, a halogen, a hydroxyl, an aryl, an amide, a cyano, a substituted or unsubstituted straight- or branched-chain alkyl containing, for example, 1 to 6 carbons, a substituted or unsubstituted alkene containing, for example, 2 to 4 carbons, —C(O)R$^3$, —CO$_2$R$^3$, —OC(O) R$^3$, —OR$^3$, or —OC(O)R$^5$. Each R$^3$ can independently be a hydrogen, a substituted or unsubstituted C$_1$-C$_{10}$ straight-chain or branched-chain alkyl, or a substituted or unsubstituted alkene. Each R⁵ can independently be a hydrogen, an unsubstituted straight- or branched-chain alkyl which contains 1-6 carbons, or a straight- or branched-chain alkyl which contains 1-6 carbons and is substituted by an alkyne. Examples of compounds of formula (II) can include Compound 2 shown below and derivatives thereof:

Compound 2

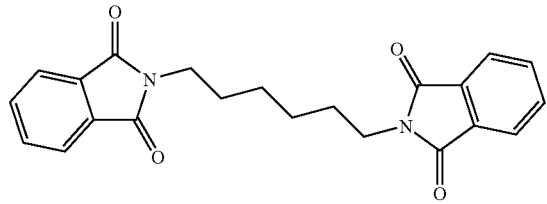

In some other aspects, the invention provides photoactive compounds of formula (III):

(III)

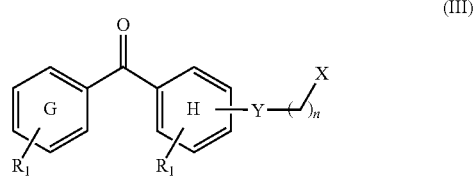

wherein each of the rings G and H can independently be substituted with one or more $R_1$ groups and n can be any suitable integer from 1 to 1000 (e.g., 1 to 100, 1 to 20, such as 11). In formula (III), X can be $R^2$, —$CO_2R^3$, —C(O)$NR^3R^3$, —$SR^4$, —CN, —$OR^3$, a halogen, a β-diketone, a silane, a phosphate, a phosphonate, a polymer, or block copolymer. In some embodiments, X can be bound to a surface. $R_1$ can independently be a hydrogen, a halogen, a hydroxyl, an aryl, an amide, a cyano, —$R^2$, —C(O)$R^3$, —$CO_2R^3$, —OC(O)$R^3$, or —$OR^3$. Each $R^2$ can independently be hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —OC(O)$R^5$, wherein $R^5$ can independently be a hydrogen, an unsubstituted straight- or branched-chain alkyl which contains 1-6 carbons, or a straight- or branched-chain alkyl which contains 1-6 carbons and is substituted by an alkyne. Each $R^3$ can independently be a hydrogen, a substituted or unsubstituted $C_1$-$C_{10}$ straight-chain or branched-chain alkyl, or a substituted or unsubstituted alkene. Each $R^4$ can independently be a hydrogen, —S-pyridyl, —$SR^3$, —$SO_2R^3$, or —$SR^8$, wherein the —$SR^8$ and the rest of formula (III) can combine to form a bis-disulfide. Y can independently be —$CH_2$—, —C(O)—, —OC(O)—, —C(O)O—, —C(O)$NR^3$—, or —$NR^3$C(O)—. Examples of a compound of formula (III) can include Compound 3 shown below and derivatives thereof:

Compound 3

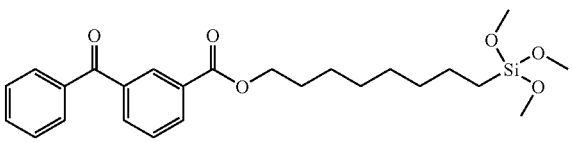

In other aspects, the invention provides photoactive compounds of formula (IV):

(IV)

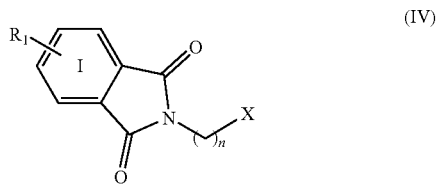

wherein ring I can be substituted with one or more $R_1$ groups and n can be any suitable integer from 1 to 1000 (e.g., 1 to 100, 1 to 20, such as 11). In formula (IV), X can be $R^2$, —$CO_2R^3$, —C(O)$NR^3R^3$, —$SR^4$, —CN, —$OR^3$, a halogen, a β-diketone, a silane, a phosphate, a phosphonate, a polymer, or block copolymer. In some embodiments, X can be bound to a surface. $R_1$ can independently be a hydrogen, a halogen, a hydroxyl, an aryl, an amide, a cyano, —$R^2$, —C(O)$R^3$, —$CO_2R^3$, —OC(O)$R^3$, or —$OR^3$. Each $R^2$ can independently be hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —OC(O)$R^5$, wherein $R^5$ can independently be a hydrogen, an unsubstituted straight- or branched-chain alkyl which contains 1-6 carbons, or a straight- or branched-chain alkyl which contains 1-6 carbons and is substituted by an alkyne. Each $R^3$ can independently be a hydrogen, a substituted or unsubstituted $C_1$-$C_{10}$ straight-chain or branched-chain alkyl, or a substituted or unsubstituted alkene. Each $R^4$ can independently be a hydrogen, —S-pyridyl, —$SR^3$, —$SO_2R^3$, or —$SR^8$, wherein the —$SR^8$ and the rest of formula (IV) can combine to form a bis-disulfide. Examples of a compound of formula (IV) can include Compound 4 shown below and derivatives thereof:

Compound 4

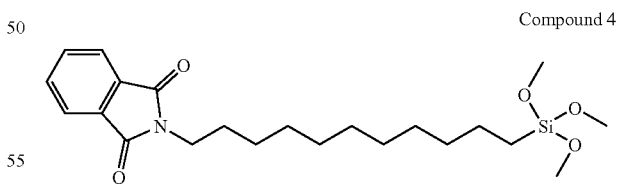

In some embodiments, the photoactive compounds of the invention can include compounds that can form radicals that lead to the formation of covalent bonds. For example, exposure to UV light can allow the photoactive compound to undergo photochemical hydrogen abstraction reactions (e.g., abstracting a hydrogen atom from a nearby molecule). The resulting radicals can then recombine, forming a covalent bond. In some embodiments, the photoactive compounds of the invention can include compounds that can form radicals near a carbonyl group. Moreover, the photoactive compounds of the invention can include aromatic carbonyl functional groups that can react with hydrogen atom donors (e.g., C—H groups, Si—H groups, S—H groups, and the like) upon absorption of a photo to form covalent bonds. As an example, FIG. 1 schematically demonstrates the abstraction of hydrogen from a phthalimide derivative, undergoing a transition to produce an excited n-π* state. As shown, a radical can be generated near a carbonyl group, which then can form a new covalent bond by reacting with nearby molecules. Other examples of photoactive compounds of the invention can include mono-benzophenone, bis-benzophenone, mono-phthalimide, bis-phthalimide, or derivative compounds thereof.

Alternatively, the photoactive compounds of the invention can abstract electrons from molecules that have suitable electron donating groups, such as amines and sulfides. Electron transfer to the photoactive compound can be followed by proton transfer and can result in covalent bond formation between the photoactive compound and the molecule having a suitable electron donating group in a manner similar to hydrogen abstraction described above.

The specific choice of photoactive compound for use in the invention will depend on characteristics of the desired application. For example, self quenching ability, quenching by a particular polymer, miscibility in various polymers, and whether there are chromophores in the surrounding that are affected by various wavelengths of light can all be factors to consider in choosing the desired photoactive compounds of the invention.

The invention also provides compounds of Formula (V):

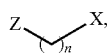
(V)

wherein X can be —$R^2$, —$CO_2R^3$, —$C(O)NR^3R^3$, —$SR^4$, —CN, —$OR^3$, a halogen, a β-diketone, a silane, a phosphate, a phosphonate, a polymer, or block copolymer; Z can be —$NR^3R^3$, —OH, —SH, —$C(O)NR^3R^3$, —$CO_2R^3$, a carboxylate, an ammonium, or a salt thereof; and n can be an integer from 1 to 1000, such as 1 to 100, 1 to 30, 1 to 20, 1 to 15, 1 to 10, 5 to 20, 5 to 15, 5 to 10, or 15 to 30, or n is 8, 9, 10, 11, 12, or 13. Each $R^2$ can independently be hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —$OC(O)R^5$, wherein $R^5$ can independently be a hydrogen, an unsubstituted straight- or branched-chain alkyl which contains 1-6 carbons, or a straight- or branched-chain alkyl which contains 1-6 carbons and is substituted by an alkyne. Each $R^3$ can independently be a hydrogen, a substituted or unsubstituted $C_1$-$C_{10}$ straight-chain or branched-chain alkyl, or a substituted or unsubstituted alkene. Each $R^4$ can independently be a hydrogen, —S-pyridyl, —$SR^3$, —$SO_2R^3$, or $SR^8$, wherein the —$SR^8$ and the rest of formula (V) can combine to form a bis-disulfide. In one embodiment, Z can be a polar group or a group that has a charge, such as a positive or negative charge. Examples of a compound of formula (V) can include Compound 5 shown below and derivatives thereof:

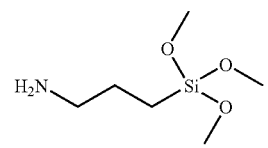
Compound 5

In some embodiments, compounds of Formula (III), (IV), and (V) can be immobilized on a surface as a mixture containing at least two of the compounds. For example, the compounds of Formula (V) can be mixed together with a compound of Formula (III) or (IV), or both, prior to or concurrently with addition to the surface. The compound of Formula (V) may be able to improve the biomolecular compatibility and/or binding affinity for molecules to be immobilized, such as a carbohydrate, to surfaces having the compounds of Formula (III) and/or (IV).

In some embodiments, the ratio of compound of Formula (V) to compound of Formula (III) and/or (IV) may be from about 100:1 to about 1:1. For example, the ratio of compound of Formula (V) to compound of Formula (III) and/or (IV) may be from about 100:1, 80:1, 60:1, 50:1, 30:1, 20:1, 10:1, 5:1, 2:1, and the like to about 1:1.

Therefore, the compounds of the invention have a number of significant advantages over those of the conventional art. For example, a protecting group is not needed which can facilitate in the synthesis of the compounds. Moreover, additional reagents are not needed to react with the compounds as the radicals that form upon irradiation can readily form covalent bonds with nearby molecules.

It should be noted that other photoactive compounds having a similar structure to that shown for compounds of Formula (I) through (IV) described above are within the scope of the invention. For example, the phthalimide or benzophenone portion of compounds of Formula (I) through (IV) can be replaced with acetone, xanthone, and other aromatic hydrocarbons having carbonyl groups. For example, compounds of Formula (VI) are within the scope of the invention,

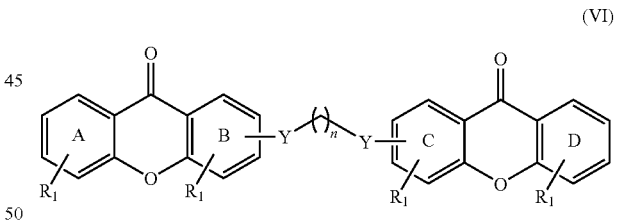
(VI)

wherein each of the rings A-D can independently be substituted with one or more $R_1$ groups and n can be any integer from 1 to 1000 (e.g., 1 to 10, such as 2). In formula (VI), $R_1$ can independently be a hydrogen, a halogen, a hydroxyl, an aryl, an amide, a cyano, a substituted or unsubstituted straight- or branched-chain alkyl containing, for example, 1 to 6 carbons, a substituted or unsubstituted alkene containing, for example, 2 to 4 carbons, —$C(O)R^3$, —$CO_2R^3$, —$OC(O)R^3$, —$OR^3$, or —$OC(O)R^5$. Each $R^3$ can independently be a hydrogen, a substituted or unsubstituted $C_1$-$C_{10}$ straight-chain or branched-chain alkyl, or a substituted or unsubstituted alkene. Each $R^5$ can independently be a hydrogen, an unsubstituted straight- or branched-chain alkyl which contains 1-6 carbons, or a straight- or branched-chain alkyl which contains 1-6 carbons and is substituted by an alkyne. Y can independently be —$CH_2$—, —C(O)—, —OC(O)—, —C(O)

O—, —C(O)NR$^3$—, or —NR$^3$C(O)—. In one embodiment, one or more R$_1$ groups can be at the meta and/or para positions of each of the rings A-D. Other exemplary compounds described above will be readily apparent to one of ordinary skill in the art.

Controlling Surface Properties of Material

The invention relates to methods for controlling surface properties of materials. In certain embodiments, methods for controlling the dewetting properties of layers on surfaces are described. In other embodiments, methods for providing a desired architecture on a surface are provided by controlling the dewetting properties of layers on surfaces. In yet other embodiments, methods for controlling the affinity for certain materials on the surface are provided.

In the following embodiments, compounds of formula (I), compounds of formula (II), compounds of formula (III), and/or compounds of formula (IV) can be utilized as a photoactive compound. For example, mono-benzophenone, bis-benzophenone, mono-phthalimide, bis-phthalimide, or derivative compounds thereof can be utilized. The amount of compound added will depend on the desired amount for each application, as can be readily determined by one skilled in the art. For example, the photoactive compound can be utilized as a 1% solution.

In certain embodiments, irradiation can be carried out with ultraviolet light. In some embodiments, light of wavelengths from 290-350 nm, (e.g., 290-300 nm and/or 330-350 nm) can be used in the invention. In one embodiment, the polymer film can be irradiated for a period of time suitable to form the desired amount of cross-links. For example, the polymer film can be irradiated for about an hour. The extent of reaction may be monitored with techniques known to the skilled artisan, such as optical microscopy and atomic force microscopy to look at the degree of dewetting, and infrared spectroscopy to look at the disappearance of the carbonyl peak.

The surface can be the surface of an inorganic material, an organic material, a polymer, and the like. For example, the surface can be the surface of silicon, titania, glass, gold, polycarbonate, polystyrene, poly(vinyl alcohol), poly(tert-butyl acrylate), poly(methyl methacrylate), paper, fingernail, and the like.

In certain embodiments, the surface can be the surface of a device, such as a chip, an optical lens, a plate, a sensor, a biomedical device, a circuit, a substrate for electroplating, or a combination thereof.

Controlling Dewetting Properties of Polymers

Figure 2:
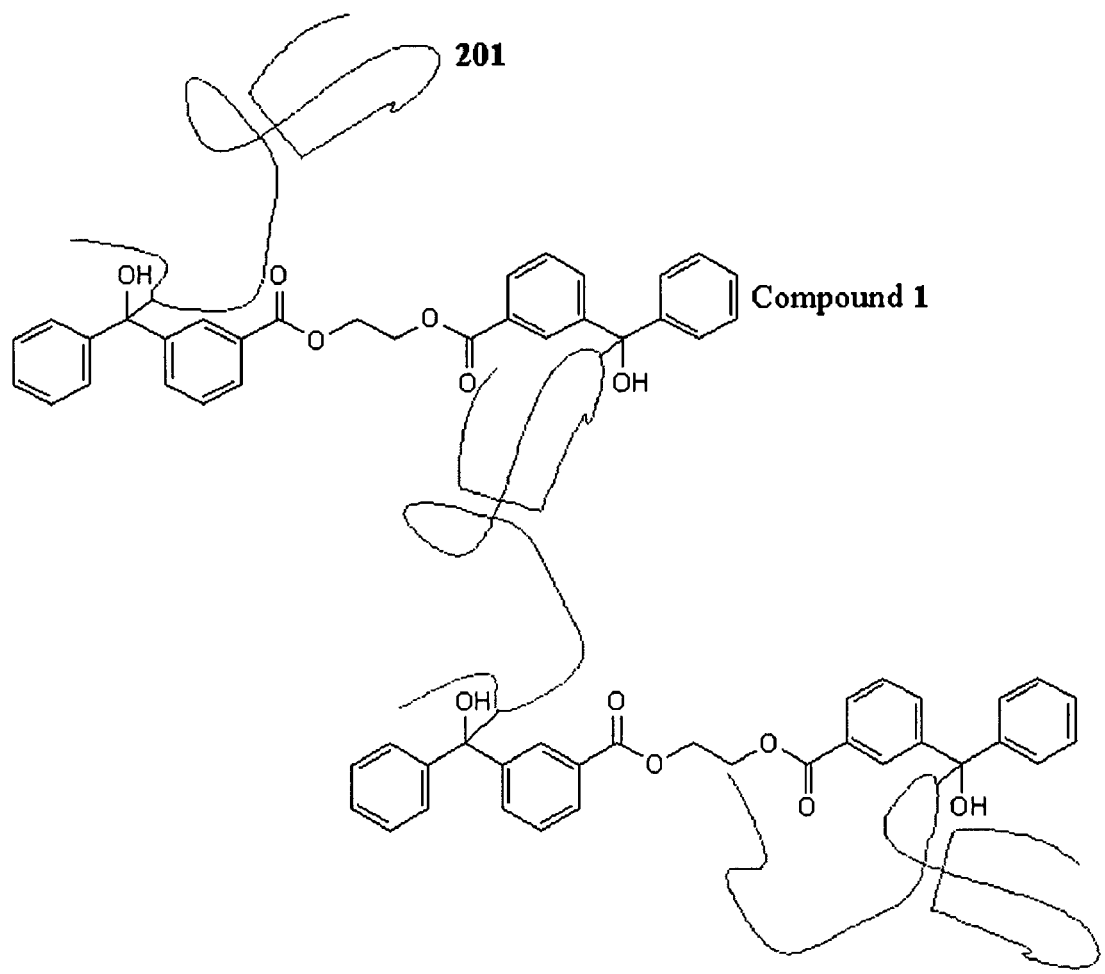
FIG. 2 shows a schematic of a polymer crosslinked with Compound 1 of the invention.

In certain embodiments, the invention relates to methods for stabilizing layers from dewetting from a surface. Methods of the invention can include (1) adding a photoactive compound (e.g. Compound 1 shown in FIG. 2) to a polymer 201 on a surface, where the photoactive compound is capable of forming covalent bonds with nearby molecules upon irradiation, and (2) irradiating the compound to form a cross-linked polymer. The resulting cross-linked polymer, schematically shown in FIG. 2, can be resistant to dewetting from the surface. For example, the cross-linked polymer can be resistant to dewetting even after heating above the glass transition temperature or melting temperature of the polymer and/or after exposure to one or more solvents.

In yet other embodiments, methods of the invention can include (1) coating a surface with a composition that include a polymer and a photoactive compound capable of forming covalent bonds with nearby molecules after irradiation, and (2) irradiating the composition to form a cross-linked polymer.

The cross-linked polymer described above can be formed as a coating on a surface, and at various thicknesses. For example, the cross-linked polymer can form a coating with a thickness of less than 5 nm, 10 nm, 20 nm, 50 nm, 100 nm, 500 nm, 1 micron, 10 micron, 50 micron, 100 micron, 200 micron, 300 micron, 500 micron and the like. If a monolayer of polymer is formed on the surface, the thickness can depend on the molecular weight of the polymer. In some embodiments, the polymer may be applied to the surface by spin coating, spray coating, or any other conventional techniques known in the art to obtain a uniform coating.

In some embodiments, the photoactive compound can further include a desired functional group. Some examples of desired functional group include functional groups that have specific affinity to other molecules, such as peptides or small molecules. In other embodiments, one or more additional compounds that are capable of providing a desired functionality can be added to a polymer on a surface. Some examples of one or more additional compounds can include one or more of a peptide, growth factor, antibody, small molecule drug, carbohydrate, lipid, antibiotic, antimicrobial, and the like. In some embodiments, the desired functionality may be at least some resistance to antigens, nerve agents, and the like.

Any polymer can be used in the invention. Some exemplary polymers can include polymers that contain a tertiary hydrogen and electron donating or withdrawing groups that can form resonance structures with the resulting radical after hydrogen abstraction occurs on the polymer chain, such as polystyrenes, polyethers, polyesters, polyamides, polyvinyls, polysaccharides, and the like.

The invention also provides methods for forming a non-dewetting, patterned array of cross-linked polymer. In certain embodiments, a robotic spotter can be utilized to pattern areas containing a photoactive compound and polymer, and the patterned array can be irradiated. Alternatively, a mask containing the desired pattern or image can be placed over a surface coated with a photoactive compound and polymer, and the coating can be irradiated though the mask. Other suitable methods to form a patterned array of cross-linked polymer will be readily apparent to one of ordinary skill in the art. The patterned array of cross-linked polymer can become resistant to dewetting.

The cross-linked polymer films of the invention have applications in thin film device fabrication, particularly in microelectronics, sensors, and coating compositions. For example, a polymer surface applied to a surface acoustic wave sensor can serve as an artificial nose or sniffer system. Generally, thin polymer films are coated onto quartz, and an aromatic ketone group on the surface reacts in the presence of light, where adsorption causes a change in the wave sensor. The invention can provide polymer films that can be utilized to form stable surfaces that that normally would not be stable and improve the performance of these devices.

Other examples include use of the polymer films as adhesives, such as self-adhesives, hot-melt adhesives, or as UV-curable binding agents in coating compositions, such as protective materials for coating mineral surfaces or as paints. The methods of the invention are particularly suitable for the production of coatings and protective films, such as coatings for clothing, cosmetics, and personal care products.

The cross-linked polymer film of the invention can also be applied as a removable layer in many applications. For example, a polymer can be applied to the skin of a burn patient, cross-linked to form a protective surface layer, and the cross-linked polymer can be peeled off later. A crosslinked polymer of the invention can also be used as a tough surface layer for inorganic substrates, such as hydrogels or monolayers.

The addition of a desired functionality to the non-dewetting cross-linked polymer film can be particularly desirable for some thin film applications. For example, the methods of the invention can be suitable for linking biological molecules such as peptides, growth factors, antibodies, small molecule drugs, carbohydrates, lipids, antibiotics and antimicrobials to non-dewetting polymer films. For wound healing applications, polymer films can be fabricated to deliver biological molecules such as growth factors or antigen-resistant drugs to the site of injury.

The methods of the invention are also applicable to the development of protective coatings for use against biological weapons. For example, a desired functionality such as nerve agent or antigen resistance can be provided to a polymer, and the polymer applied as a protective coating to clothing worn by military personnel.

Forming Three-Dimensional Structures on Surfaces

The invention also provides methods for forming three-dimensional structural features. Methods of the invention can include (1) adding a photoactive compound to a polymer on a surface, where the photoactive compound is capable of forming covalent bonds with nearby molecules upon irradiation, (2) placing a mask which contains a desired pattern, (3) irradiating the photoactive compound through the mask to form a pattern of cross-linked and uncrosslinked polymer, and (4) heating the pattern to a temperature that is near or above the glass transition temperature or the melting temperature of the polymer. Upon heating the surface, at least some of the uncrosslinked polymer can migrate toward the interface between the crosslinked and uncrosslinked regions to form a vertical structure.

In other embodiments, methods of the invention can include (1) coating a surface with a composition that includes a polymer and a photoactive compound capable of forming covalent bonds with nearby molecules after irradiation, (2) placing a mask which contains a desired pattern, (3) irradiating the photoactive compound through the mask to form a pattern of cross-linked and uncrosslinked polymer, and (4) heating the pattern to a temperature that is near or above the glass transition temperature or the melting temperature of the polymer. Upon heating the surface, at least some of the uncrosslinked polymer can migrate toward the interface between the crosslinked and uncrosslinked regions to form a vertical structure.

In yet other embodiments, methods of the invention can include (1) coating a surface with a polymer (2) forming on the polymer a pattern of photoactive compound capable of forming covalent bonds with nearby molecules after irradiation, (3) irradiating the photoactive compound to form a pattern of cross-linked and uncrosslinked polymer, and (4) heating the pattern to a temperature that is near or above the glass transition temperature or the melting temperature of the polymer. Upon heating the pattern, at least some of the uncrosslinked polymer can migrate toward the interface between the crosslinked and uncrosslinked regions to form a vertical structure.

In some embodiments, the polymer may be applied to the surface by spin coating, spray coating, or any other conventional techniques known in the art to obtain a uniform coating.

The polymer described above can be formed as a coating on a surface, and at various thicknesses. For example, the polymer may be formed as a coating with a thickness of greater than 1 nm, 5 nm, 10 nm, 20 nm, 50 nm, 100 nm, 500 nm, 1 micron, 10 micron, 50 micron, 100 micron, 200 micron, 300 micron, 500 micron and the like. If a monolayer of polymer is formed on the surface, the thickness can depend on the molecular weight of the polymer.

The pattern described above can be formed at various widths. For example, the uncrosslinked or crosslinked regions can be formed have a width that is greater than 20 nm, 50 nm, 100 nm, 500 nm, 1 micron, 10 micron, 50 micron, 100 micron, 200 micron, 300 micron, 500 micron, 1 mm, and the like.

The height of the vertical structure that builds up near the interface of the crosslinked and uncrosslinked regions can be dependent on the thickness of the polymer film and/or the width of the uncrosslinked regions. Greater thickness and width of the uncrosslinked regions may lead to greater height of the vertical structure near the interface. The height of the material that builds up near the interface can be greater than 5 nm, 10 nm, 20 nm, 50 nm, 100 nm, 200 nm, 300 nm, 500 nm, 1000 nm, and the like.

In some embodiments, the photoactive compound can further include a desired functional group. Some examples of desired functional group can include functional groups that have specific affinity to other molecules, such as peptides or small molecules. In other embodiments, a second compound that is capable of providing a desired functionality can be added to a polymer on a surface. Some examples of the second compound include one or more of a peptide, growth factor, antibody, small molecule drug, carbohydrate, lipid, antibiotic, antimicrobial, and the like. In some embodiments, the desired functionality may be at least some resistance to antigens, nerve agents, and the like.

Any suitable polymer can be used in the invention. Some exemplary polymers can include polymers that contain a tertiary hydrogen and electron donating or withdrawing groups that can form resonance structures with the resulting radical after hydrogen abstraction occurs on the polymer chain, such as polystyrenes, polyethers, polyesters, polyamides, polyvinyls, polysaccharides, and the like.

The patterned three-dimensional structures can be utilized in a number of different applications, such as for microreactors carrying out microscopic amounts of reaction near the surface. The patterned three-dimensional structures may be utilized as assays to determine which reactions are successful by placing suitable markers after reaction. For example, to test for successful synthesis of a particular carbohydrate, various different reagents can be utilized in each microreactor. After the surface has been subjected to a suitable reaction condition, a marker can be deposited into the microreactors, where the marker fluoresces only when it binds to the carbohydrates that form after a completed reaction. The detection of the fluorescence signal in various microreactors can be utilized to determine which reagents are suitable for a successful reaction.

Immobilizing Molecules on a Surface

Other embodiments of the invention also relate to methods for immobilizing molecules on a surface. Methods of the invention can include (1) immobilizing on a surface a photoactive compound capable of forming covalent bonds with nearby molecules after irradiation; (2) applying a molecule to the photoactive compound; and (3) irradiating the photoactive compound, wherein a photochemical reaction between the photoactive compound and the molecule results in covalent links between the molecule and the photoactive compound to immobilize the molecule near the surface. In certain embodiments, the photoactive compound can be immobilized on the surface as a self-assembled monolayer (see FIG. 3). In other embodiments, the photoactive compound can be immobilized on the surface as a multilayer.

In other some embodiments, methods of the invention can include (1) immobilizing on a surface a composition that includes a photoactive compound capable of forming covalent bonds with nearby molecules after irradiation and a second compound that can increase the affinity of desired molecules to the composition; (2) applying a molecule to the composition; and (3) irradiating the composition, wherein a photochemical reaction between the photoactive compound and the molecule results in covalent links between the molecule and the photoactive compound to immobilize the molecule near the surface. In certain embodiments, the composition can be immobilized on the surface as a self-assembled monolayer. In other embodiments, the photoactive compound can be immobilized on the surface as a multilayer.

In some embodiments, the molecule that forms covalent links with the photoactive compound can be a carbohydrate.

The invention also provides methods for immobilizing a patterned array of molecules on a surface. A mask containing the desired pattern or image can be placed over the coated surface and irradiated through the mask. Alternatively, a robotic spotter can be utilized to pattern areas containing a photoactive compound and a molecule, and the patterned array can be irradiated. Other suitable methods to form a patterned array of immobilized carbohydrates will be readily apparent to one of ordinary skill in the art.

The photoactive compound and/or the immobilized molecule can be formed as a coating on a surface, and at various thicknesses. For example, the molecule may form a coating with a thickness of less than 1 nm, 2 nm, 5 nm, 10 nm, 20 nm, 50 nm, 100 nm and the like. For example, if a monolayer of immobilized molecule is formed on the surface, the thickness can depend on the molecular weight of the molecule. In some embodiments, the molecule may be applied to the surface by spin coating, spray coating, or any other conventional techniques known in the art to obtain a uniform coating.

In some embodiments, the photoactive compound can further include a functional group capable of being immobilized on a surface. Some examples of functional group capable of being immobilized on a surface include a carboxylic acid, thiol, β-diketone, silane, phosphate, phosphonate, alkane, alkene, or alkyne, polymer, block co-polymer, and the like. In some other embodiments, the photoactive compound can be incorporated into polymers and/or hydrogels to modify the molecule-surface interfacial tension or to modify steric constraints that may make the photoactive portion of the molecule inaccessible.

Any suitable molecules can be utilized. Carbohydrates, polymers, lipids, proteins, and the like can be utilized. For example, carbohydrates, such as monosaccharides, disaccharides, trisaccharides, tetrasaccharides, oligosaccharides, polysaccharides, glycosides thereof, and the like, can be utilized in the invention. In some embodiments, the carbohydrate can be a simple carbohydrate, such as glucose or sucrose. In other embodiments, a 2000 kDA dextran can be utilized. In some other embodiments, the carbohydrates can be underivatized carbohydrates, without chemical modification. As another example, suitable polymers can include polyacrylic acid, polystyrene, polyvinyl alcohol, and the like. Other exemplary molecules that can be immobilized on a surface will be readily apparent to one of ordinary skill in the art.

The invention does not require the chemical modification of each molecule prior to deposition and it is not dependent on the molecular weight of the deposited molecule. Moreover, the invention can utilize bonds, such as C—H bonds, S—H bonds, Si—H bonds, and the like, which is present in many molecules (e.g., C—H bonds are readily found in carbohydrates). Moreover, the invention requires no reagents and generates no byproducts.

The invention has applications in a wide number of applications. For example, the invention can be utilized in tissue engineering, sensor fabrication, glycome sequencing, and in microarray construction for high-throughput characterization of carbohydrate enzyme activity and carbohydrate interactions with cells, antibodies, proteins and microorganisms.

Moreover, the surfaces may be used as biological sensors for identifying biological warfare agents. The invention also provides a platform for screening antibody activity towards various viruses, photopatterning any kind of polymer, biological or synthetic, that contains a C—H bond, and glycomic and proteomic studies aimed at the discovery of new drugs and the understanding of cellular processes.

The invention can also be utilized as immobilized coatings that impart desired functionality to a surface. For example, hydrophilic molecules can be immobilized on the surface of an optically transparent substrate to provide an anti-fogging substrate. An another example, hydrophobic molecules can be immobilized on the surface of a substrate to provide a surface that strongly repels water (e.g., to coat automobile windshield to repel rain water).

In some embodiments, arrays having the photoactive compounds of the invention immobilized on a surface can be utilized to covalently attach numerous molecules, such as DNA, RNA, proteins, polymers, carbohydrates, and the like to the photoactive compounds for applications described herein.

In addition, a patterned array of molecules can be utilized as a template for carrying out further reactions selectively in desired areas of the patterned surface.

Depositing Metals on a Surface

Other embodiments of the invention also relate to methods for depositing metals on a surface. Methods of the invention can include (1) immobilizing on a surface a photoactive compound capable of forming covalent bonds with nearby molecules after irradiation; (2) applying a molecule to the photoactive compound; (3) irradiating the photoactive compound, wherein a photochemical reaction between the photoactive compound and the molecule results in covalent links between the molecules and the photoactive compound to immobilize the molecule near the surface; (4) contacting the surface having immobilized molecules with a catalyst for forming a metal, where the catalyst has a selective affinity for the immobilized molecules; and (5) carrying out a metal reducing reaction to deposit metal near the immobilized molecules. In certain embodiments, the photoactive compound can be immobilized on the surface as a self-assembled monolayer. In other embodiments, the photoactive compound can be immobilized on the surface as a multilayer.

In some other embodiments, methods of the invention can include (1) immobilizing on a surface a composition that includes a photoactive compound capable of forming covalent bonds with nearby molecules after irradiation and a second compound that can increase the affinity of desired molecules to the composition; (2) applying a molecule to the composition; (3) irradiating the composition, wherein a photochemical reaction between the photoactive compound and the molecule results in covalent links between the molecule and the photoactive compound to immobilize the molecule near the surface; (4) contacting the surface having immobilized molecules with a catalyst for forming a metal, where the catalyst has a selective affinity for the immobilized molecules; and (5) carrying out a metal reducing reaction to deposit metal near the immobilized molecules. In certain embodiments, the photoactive compound can be immobilized on the surface as a self-assembled monolayer. In other embodiments, the photoactive compound can be immobilized on the surface as a multilayer.

In some embodiments, a mask containing the desired pattern or image can be placed over the surface and irradiated though the mask. Alternatively, a robotic spotter can be utilized to pattern areas containing a photoactive compound and a molecule, and the patterned array can be irradiated. Other suitable methods to form a patterned array of immobilized carbohydrates will be readily apparent to one of ordinary skill in the art.

The photoactive compound and/or the immobilized molecule can be formed as a coating on a surface, and at various thicknesses. For example, the molecule may form a coating with a thickness of less than 1 nm, 2 nm, 5 nm, 10 nm, 20 nm, 50 nm, 100 nm and the like. For example, if a monolayer of immobilized molecule is formed on the surface, the thickness can depend on the molecular weight of the molecule. In some embodiments, the molecule may be applied to the surface by spin coating, spray coating, or any other conventional techniques known in the art to obtain a uniform coating.

In some embodiments, the photoactive compound can further include a functional group capable of being immobilized on a surface. Some examples of functional group capable of being immobilized on a surface include a carboxylic acid, thiol, β-diketone, silane, phosphate, phosphonate, alkane, alkene, or alkyne, polymer, block co-polymer, and the like. In some other embodiments, the photoactive compound can be incorporated into polymers and/or hydrogels to modify the carbohydrate-surface interfacial tension or to modify steric constraints that may make the photoactive portion of the molecule inaccessible.

Any suitable molecules can be utilized. Carbohydrates, polymers, lipids, proteins, and the like can be utilized. Suitable polymers can include polyacrylic acid, polystyrene, polyvinyl alcohol, and the like. Other exemplary molecules than can be immobilized on a surface will be readily apparent to one of ordinary skill in the art.

Any suitable metals can be deposited on the surface with the use of appropriate catalysts. For example, nickel, copper, gold, silver, titanium, aluminum, silicon, and the like can be deposited. The invention has significant advantages over conventional techniques, such as electroplating, as expensive and potentially dangerous reaction conditions can be avoided.

Although the invention was described in reference to deposition of metals, other non-metals, such as insulator, semiconductors, organic molecules, polymers, and the like can be deposited, as will be readily apparent to one of ordinary skill in the art.

EXAMPLES

The invention will be further described with reference to the following examples; however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

Example 1

Synthesis of a Compound of Formula (I)

To a solution of 6.7 g (0.03 mol) of 3-benzoylbenzoic acid (Aldrich) in 250 ml of methylene chloride and 50 ml of ether in a 500 ml three necked round bottom flask which was equipped with a reflux condenser and sealed with argon was added 0.4 g (0.003 mol) of 4-pyrrolidinopyridine (Aldrich), and 6.1 g (0.03 mol) of DCC (Acros). The solution was stirred for 5 min. 0.93 g (0.015 mol) of ethylene glycol was added. The reaction mixture was stirred overnight and then refluxed for 5 hours to complete the esterification. After cooling to room temperature, the N,N-dicyclohexyl urea was removed by filtration. The filtrate was washed with water (3×100 ml), 5% acetic acid solution (3×100 ml), water (2×100 ml), and NaCl saturated water (100 ml). The solution was dried with anhydrous $Na_2SO_4$. After removing the solvent on a rotoevaporator, the product was chromatographed on silica gel with ethyl acetate/hexane (v/v=1/3). 6.5 g of Compound 1 was obtained (90% yield).

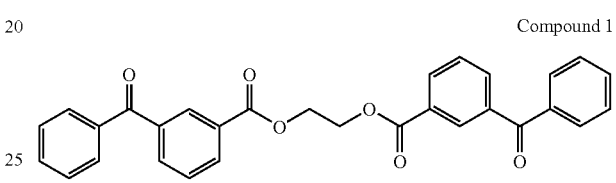

Compound 1

Example 2

Derivatization of Compound 1

Halogenation. Addition of a halogen with a Lewis acid allows for halogenation of the aromatic rings in the meta positions. The halogen can then be replaced by a molecule bearing a nucleophile.

Alkylation Using an Alkene. Addition of an alkene with a Bronsted or Lewis acid results in substitution in the meta positions.

Alkylation Using an Alcohol. Addition of an alcohol with a Bronsted or Lewis acid results in substitution in the meta positions.

Additionally, benzophenone derivatives bearing substituents that are amenable to derivatization (methoxy, alcohol, etc.) can be used to make the derivative compound of Compound 1.

Example 3

Synthesis of a Compound of Formula (II)

150 ml of DMF was added to a flask containing 1.056 g of potassium phthalimides. 0.7145 g of dibromohexane was added. The solution was stirred overnight at 20° C. 75 ml of chloroform were added to the solution followed by 50 ml $H_2O$. The organic layer was separated and extracted with 50 ml of chloroform two times. The combined organic layers were rinsed with 75 ml of $H_2O$ four times. Chloroform was removed under reduced pressure. A clear liquid removed. White needles of Compound 2 precipitated from the liquid after 12 hours. The product of was collected by filtration and washed with ether.

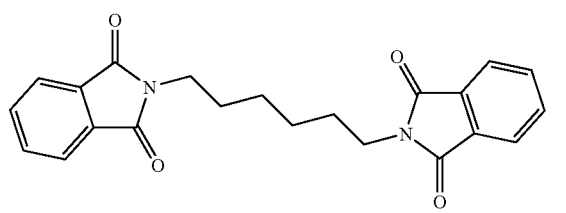

Compound 2

Example 3

Synthesis of a Compound of Formula (IV)

Figure 3:
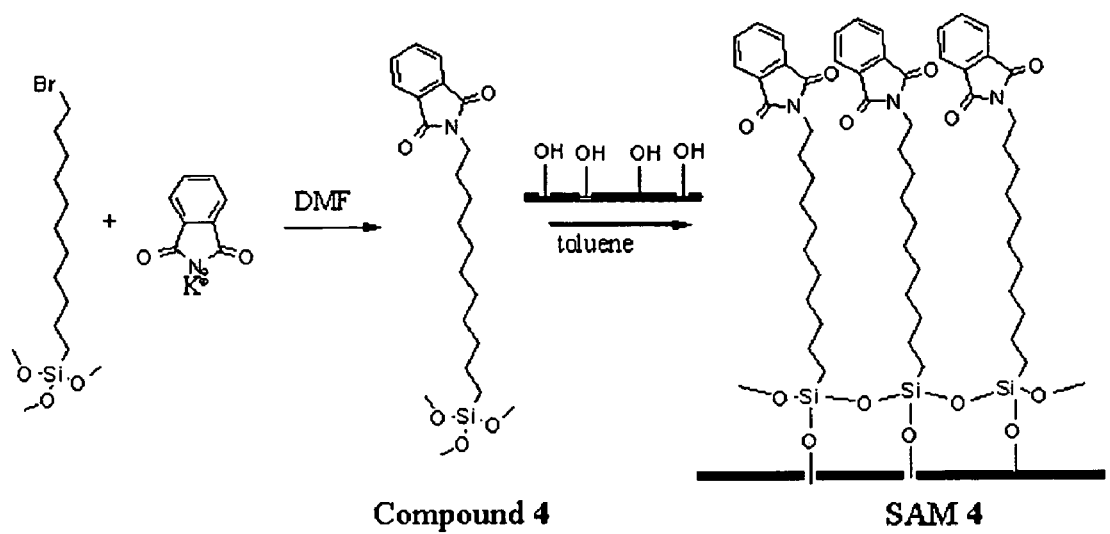
FIG. 3 shows the formation of a self-assembled monolayer containing Compound 4 of the invention form on a surface.

9.8 mmol of 11-bromoundecanetrimethoxysilane (Gelest) was added to a solution of an equimolar amount of potassium phthalimides (Aldrich) in 40 ml of anhydrous DMF (Aldrich) (see also FIG. 3). The solution was stirred overnight at room temperature under argon. 30 ml of chloroform were added. The solution was transferred to a separate flask containing 50 ml of $H_2O$. The aqueous layer was separated and then extracted with two 20 ml portions of chloroform. The combined chloroform extract was washed with three 20 ml portions of $H_2O$. The chloroform was removed by rotoevaporation to give approximately 20 ml of product (Compound 4). The compound was characterized by NMR and used without further purification.

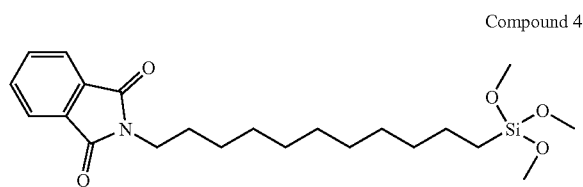

Compound 4

Example 5

Fabrication of Dewetting-Resistant Polymer Film

Figure 4:
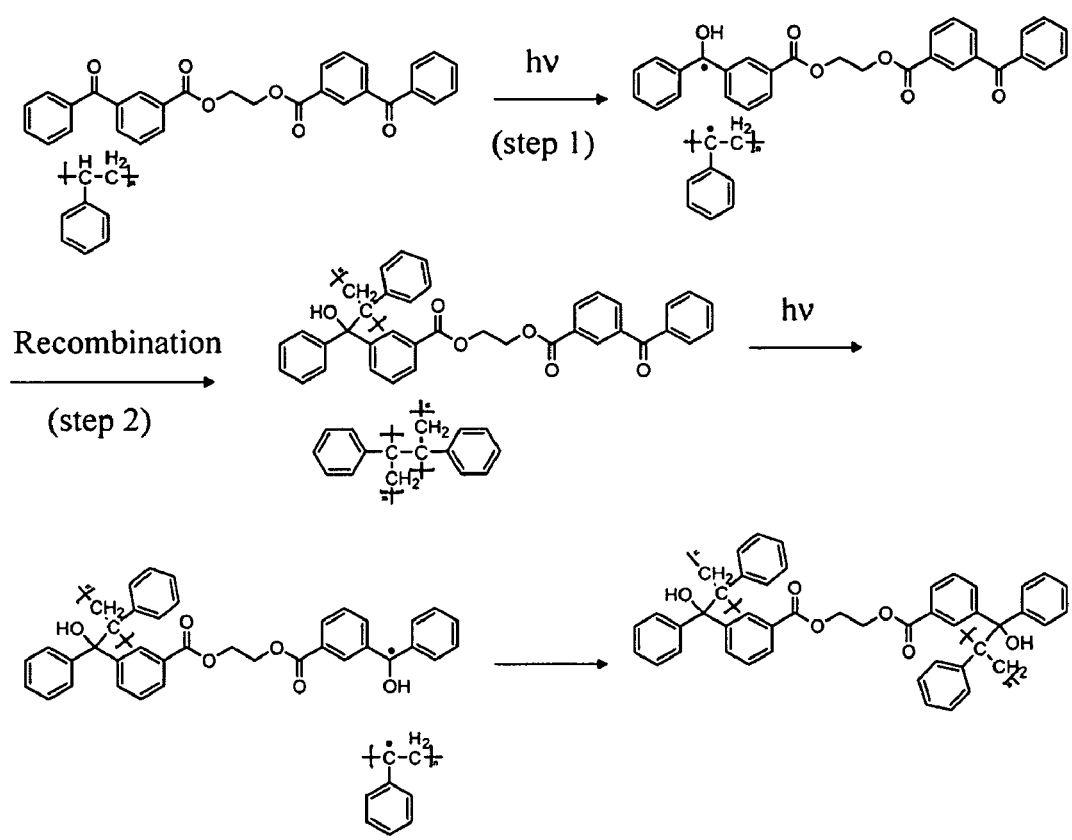
FIG. 4 shows plausible mechanisms for crosslinking of polystyrene (PS) by a Compound 1 of the invention.

Polymer films were prepared on Silicon wafers (Wafer World) by spin-coating toluene solutions containing varying amounts of polystyrene (PS) and Compound 1 (see FIG. 4). Typically, films were spun at 3000 rpm for 1 minute. Silicon wafers were cleaned by boiling in "piranha" solution (7:3 sulfuric acid/$H_2O_2$) for 1 hour followed by an extensive rinse with $H_2O$ and methanol. Surfaces were dried with a stream of argon and placed in a UV/ozone cleaner for 20 minutes prior to casting the film.

The films were placed in sealed glass vials and purged with argon for 10 minutes. The films were irradiated for 1 hour with a Rayonet Photochemical Reactor equipped with lamps that emit at 350 nm. FIG. 4 shows plausible mechanisms for the photoinduced cross-linking reaction. Irradiation is expected to produce an excited n-π* state that intersystem crosses to the triplet. One of several deactivation pathways includes hydrogen abstraction of a nearby C—H group on a PS chain (step 1). Hydrogen abstraction can form radicals that can recombine to form covalent bonds. Two potential recombination pathways can result in cross-links. First, radical centers on the PS chains can recombine with each other (step 2). This requires that the photogenerated PS radicals are located sufficiently close to each other. This pathway may be limited in that the chain motion can be hindered by the solid-state reaction conditions used to cross-link the film. Second, the inclusion of two benzophenone chromophores can supply an additional cross-linking pathway that circumvents the need to have two macroradical centers in close proximity. Recombination of two benzophenone ketyl radicals at the ends of a single molecule of Compound 1 with PS macroradicals results in cross-links without the need for two interacting PS radicals. The excitation wavelength of Compound 1 occurs around 340 nm, sufficiently separated from the absorption band of the PS phenyl rings that falls below 280 nm.

The irradiated PS films were examined by infrared (IR) spectroscopy and gel permeation chromatography (GPC). Hydrogen abstraction is expected to occur at the aromatic ketone as schematically illustrate in FIG. 4. Examination of the corresponding peak in the IR spectrum indicates whether this chromophore can participate in a photochemical reaction mixed within the polymer matrix. IR spectra show that the aromatic ketone at 1661 $cm^{-1}$ decays relative to the ester groups at 1725 $cm^{-1}$ over time (not shown). The observed decrease in the aromatic ketone absorbance as a function of time demonstrates that Compound 1 can undergo a photochemical reaction while confined in a polymer matrix.

Figure 5:
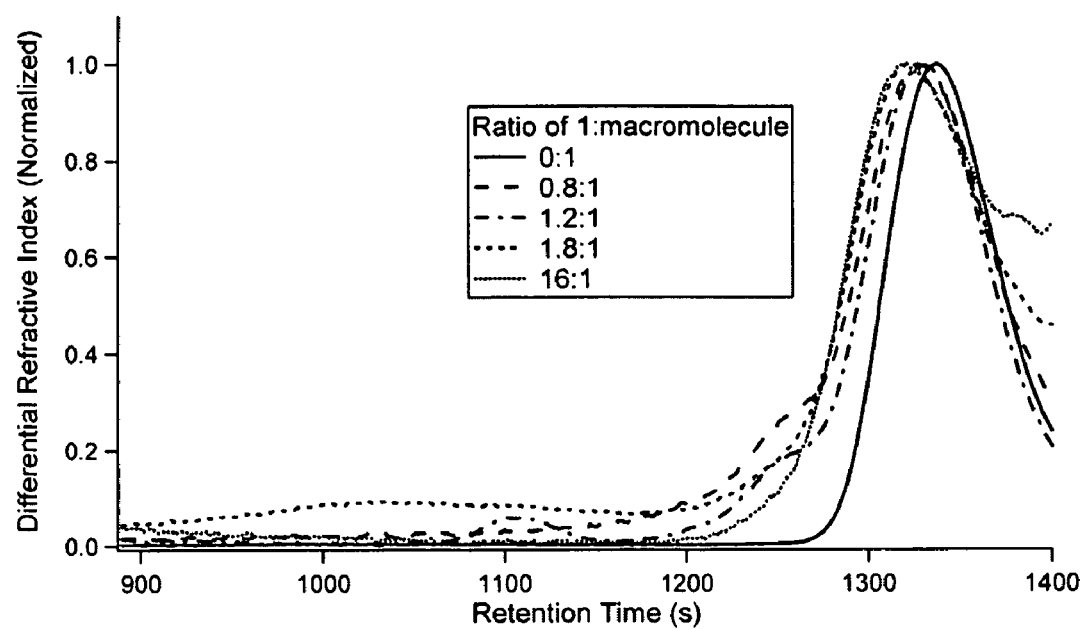
FIG. 5 shows normalized GPC traces of irradiated PS films containing varying ratios of Compound 1 of the invention to PS.

To further verify that PS can be photochemically cross-linked by photoexcitation of Compound 1 in a PS matrix, samples containing Compound 1 and PS ($M_n$=2600) were analyzed by GPC. It should be noted that GPC can qualitatively demonstrate the occurrence of cross-linking. Analysis of the GPC curves shown in FIG. 5 shows that the lowest molecular weight peak, which occurs at comparable retention times in all of the samples, shifted to higher molecular weight after irradiation. In some cases, the shift was accompanied by the growth of new peaks corresponding to higher molecular weights. The formation of higher molecular weight species suggests that irradiation of Compound 1 within the polymer film results in cross-linked (i.e., branched) PS chains. It is possible that insoluble higher molecular weight networks that were not detected using GPC were created. The decay of the aromatic carbonyl and an increase in the molecular weight of the PS chains after irradiation are consistent with the hypothesis that Compound 1 photochemically cross-links the PS chains as a result of photoinduced H abstraction.

Figure 6A:
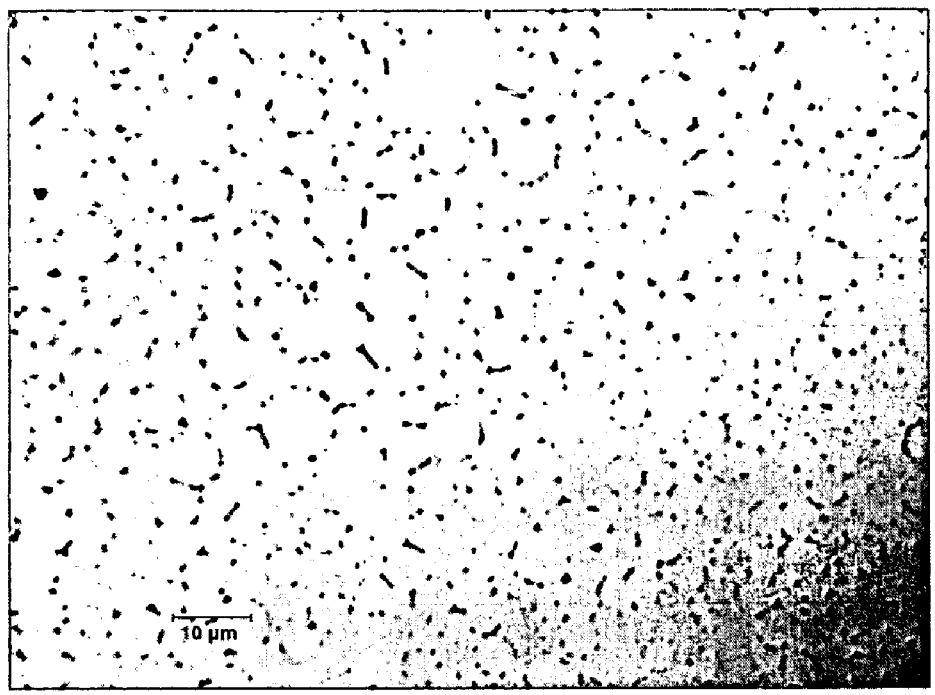
FIG. 6A shows an optical microscope image of dewetted PS film containing Compound 1 of the invention after heating at 170° C. overnight without irradiation.
Figure 6B:
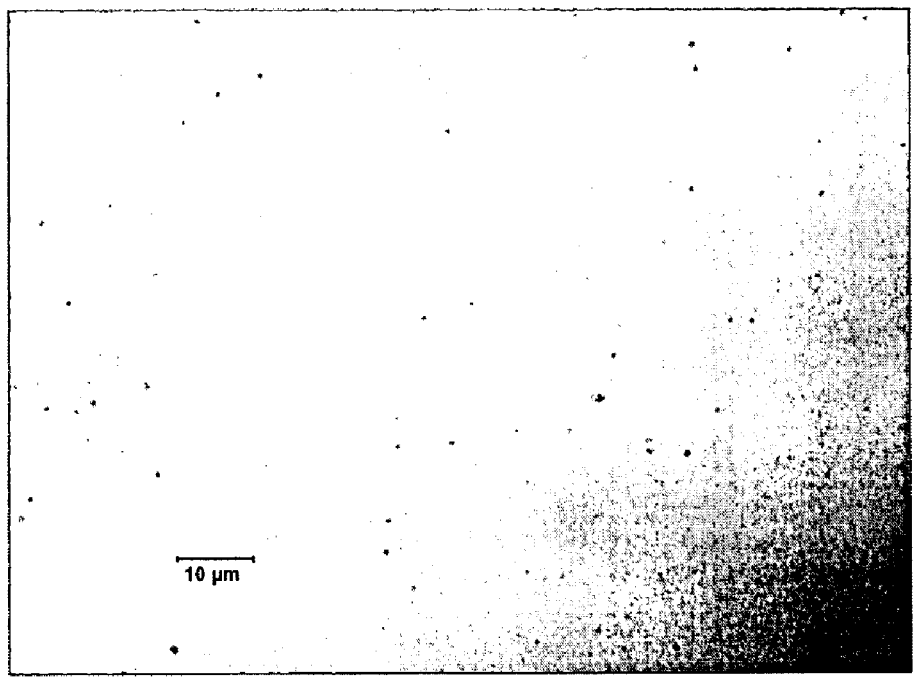
FIG. 6B shows an optical microscope image of dewetting resistant polystyrene (PS) film containing Compound 1 of the invention after irradiation and after heating at 170° C. overnight.
Figure 6C:
FIG. 6C shows an atomic force microscope (AFM) image of dewetted PS film without Compound 1 of the invention after heating at 170° C. overnight.
Figure 6D:
FIG. 6D shows an AFM image of dewetting resistant polystyrene (PS) film containing Compound 1 of the invention after irradiation and after heating at 170° C. overnight.
Figure 7A:
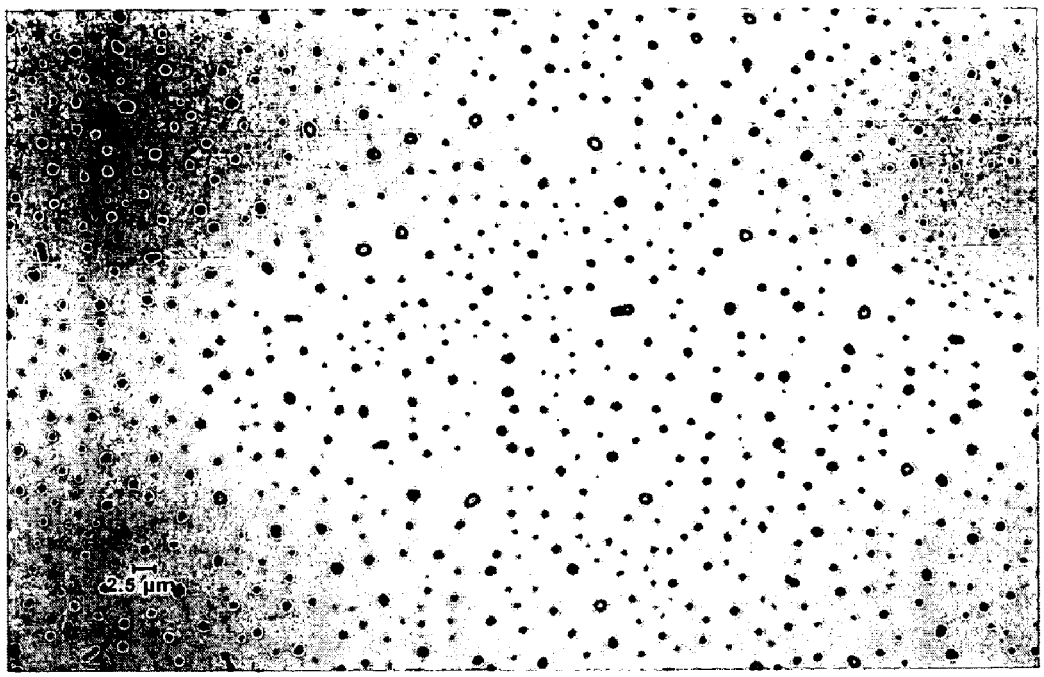
FIGS. 7A through 7D show optical microscope images of irradiated PS films containing 0 mM, 1.7 mM, 7.5 mM, and 24 mM amount of Compound 1 of the invention.
Figure 7B:
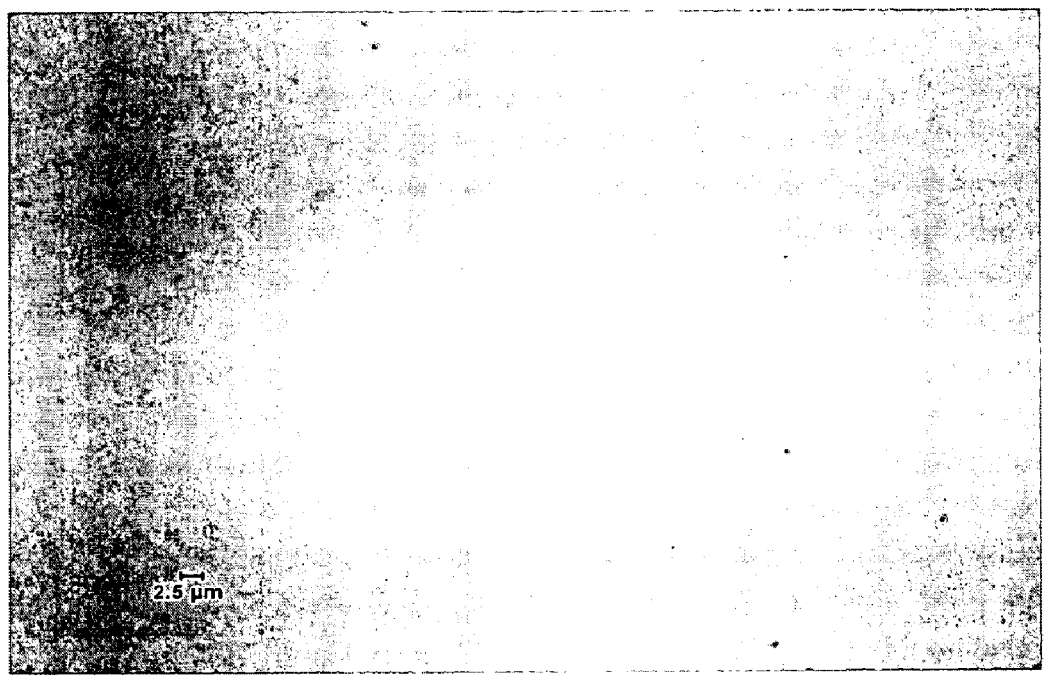
Figure 7C:
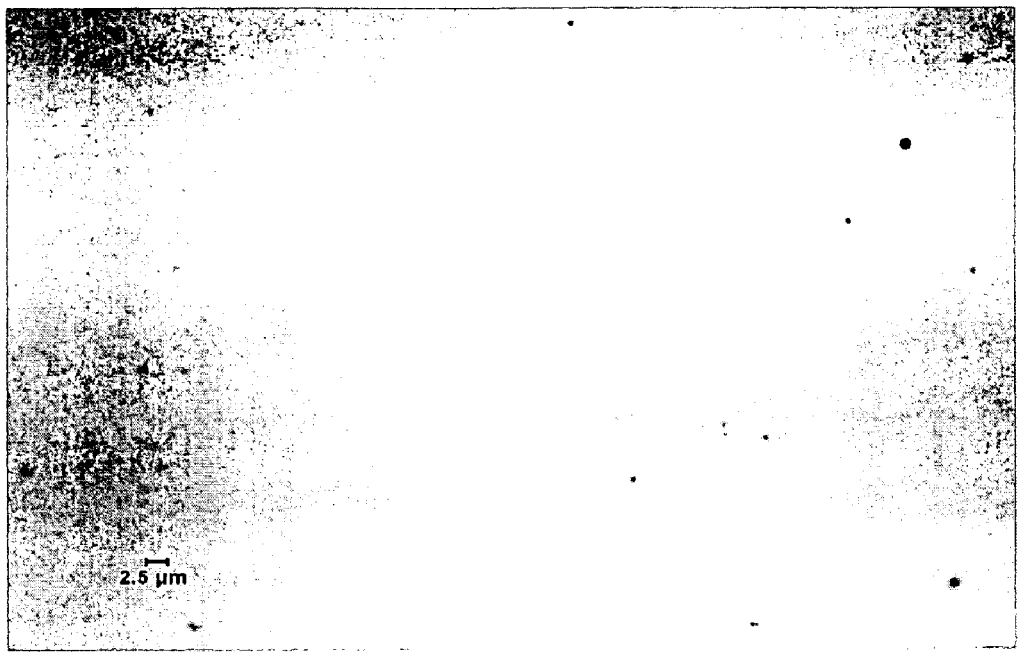
Figure 7D:
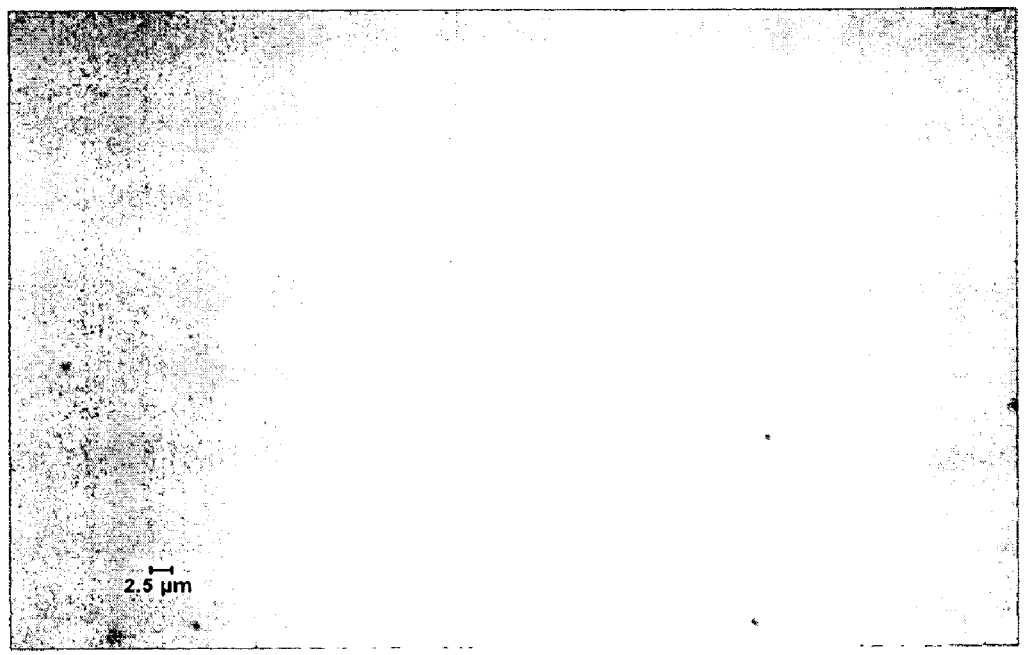

To examine the effect of crosslinking on the dewetting behavior of PS, samples having 29:1 ratio of Compound 1:PS and without any Compound 1 were heated to about 170° C. (Tg is about 100° C.). FIGS. 6A and 6B show optical microscope (OM) images of these samples (without and with Compound 1, respectively) and FIGS. 6C and 6D show atomic force microscope (AFM) images (without and with Compound 1, respectively) for these samples. As shown in FIGS. 6A and 6C, samples without any Compound 1 have numerous holes. However, as shown in FIGS. 6B and 6D, samples containing Compound 1 have significantly reduced amount of holes, suggesting increased resistance to dewetting. It should be noted that for this particular sample, the AFM images were not obtained until a hole could be found, biasing the experiment toward a positive hole result. Even with this built-in bias, the film appears to be less damaged than the sample without Compound 1. Moreover, the average roughness of the film containing Compound 1 is about 0.3 nm compared to the roughness value of 1.9 nm for the sample without Compound 1, a decrease by more than a factor of 6. These results show that irradiation of films containing Compound 1 results in cross-links that inhibit the polymer chains from reorganizing on the surface.

Figure 8A:
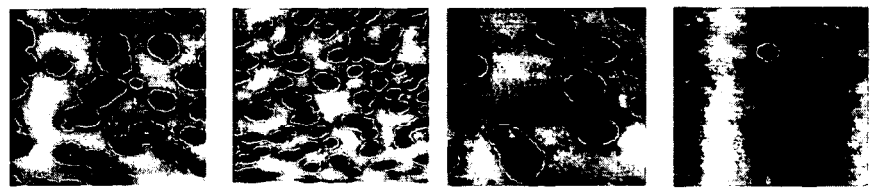
FIG. 8A shows AFM images of PS films containing varying amounts of a Compound 1 of the invention after irradiation and heating in a vacuum oven at 170° C. overnight, where the average height and average roughness were calculated by taking 3-5 random images and averaging the roughness and height.
Figure 8B:
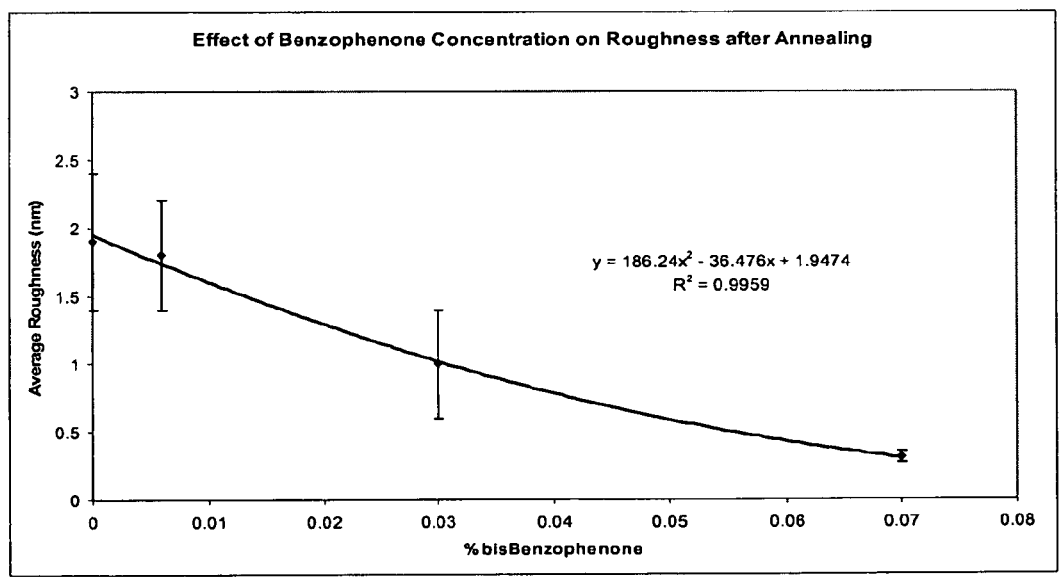
FIG. 8B shows a graph of the average roughness vs. the weight percentage of Compound 1 of the invention. Values were taken from FIG. 8A.
Figure 8C:
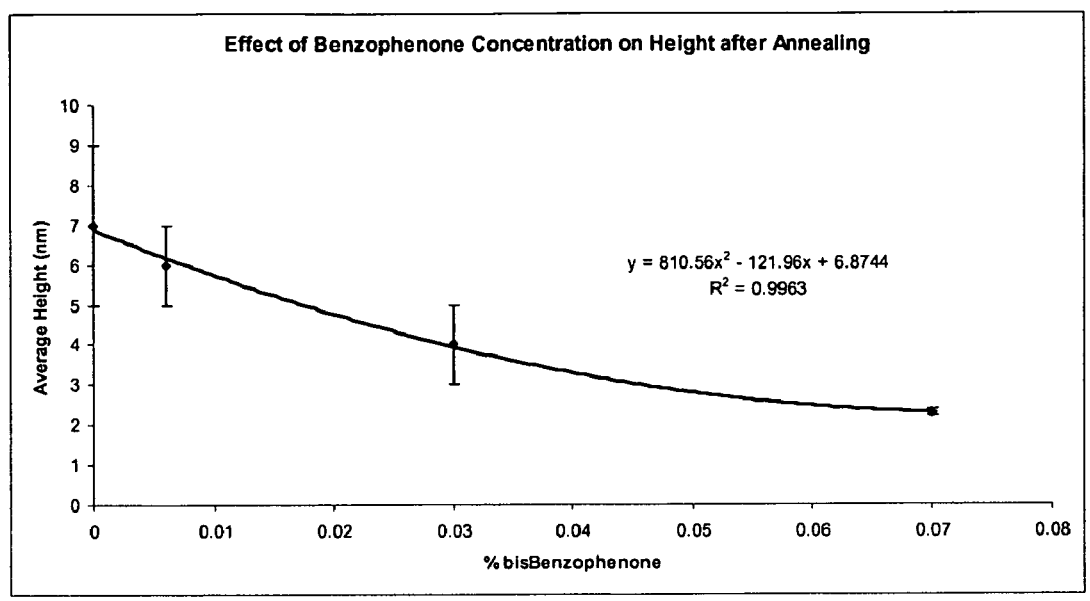
FIG. 8C shows a graph of the average height of the film vs. the weight percentage of photoactive compound of the invention. Values were taken from FIG. 8A.

Additional films were cast containing intermediate concentrations of Compound 1 relative to the 29:1 and 0:1 Compound 1:PS samples described above. FIGS. 7A through 7D show OM images of irradiated PS films containing 0, 1.7 mM, 7.5 mM, and 24 mM amounts of Compound 1 in PS, respectively. Average roughness of the baked films was determined as a function of the amount of Compound 1 in the sample from AFM images (see FIG. 8A). As shown in FIG. 8B, the roughness decreases as the amount of Compound 1 is increased. A similar trend is found when the corresponding heights of the PS films are plotted against the amount of Compound 1 in the spin-cast solution (see FIG. 8C). The average height of the annealed films decreases as the amount of cross-linker increases, suggesting that the irreversible expansion accompanied by heating a thin film above $T_g$ is attenuated. By adjusting the concentration of Compound 1 in the films, the surface topography can be controlled.

Figure 9:
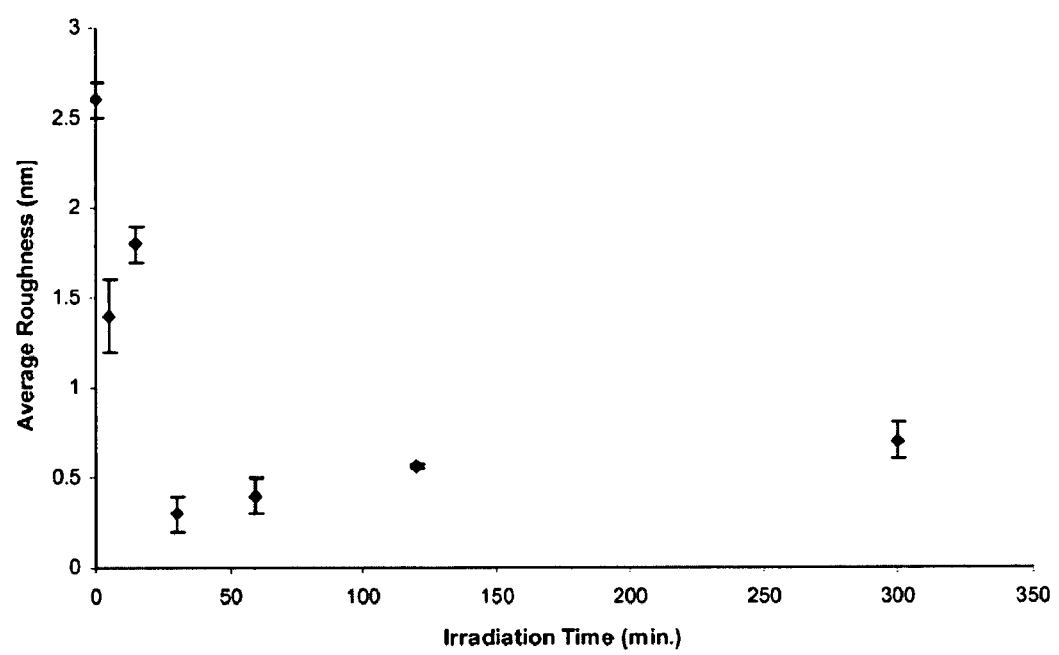
FIG. 9 shows a graph of the average roughness of PS films containing Compound 1 of the invention as a function of irradiation time. The ratio of the Compound 1 to PS is 60:1. The thickness of the films without addition of Compound 1 is approximately 2.5 nm. Data was obtained after irradiation and annealing at 170° C. overnight.

Additionally, the dosage of UV light was adjusted. FIG. 9 shows a graph of the average roughness as a function of the irradiation time for a sample containing 60:1 of Compound 1:PS. The observed dependence of surface roughness on irradiation time is in accord with surface modification via photochemical means. As shown, significant decrease in the roughness of the films is not observed after about 30 minutes of irradiation.

Figure 10A:
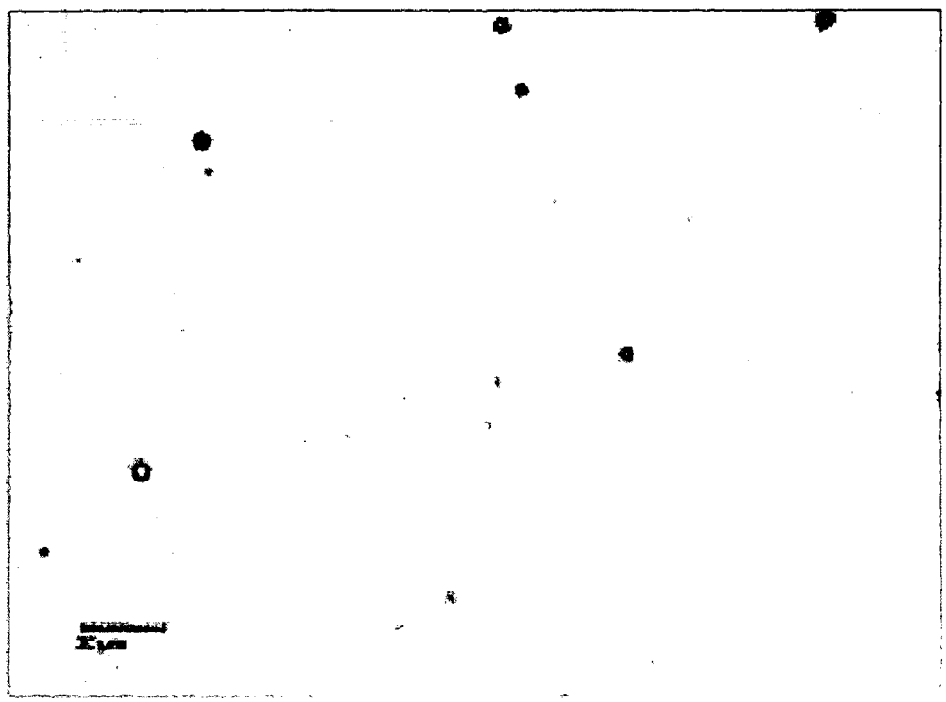
FIG. 10A shows an optical microscope image of 25 nm PS film containing Compound 1 of the invention (1:3 ratio of PS:Compound 1) after irradiation and annealing at 170° C. overnight.
Figure 10B:
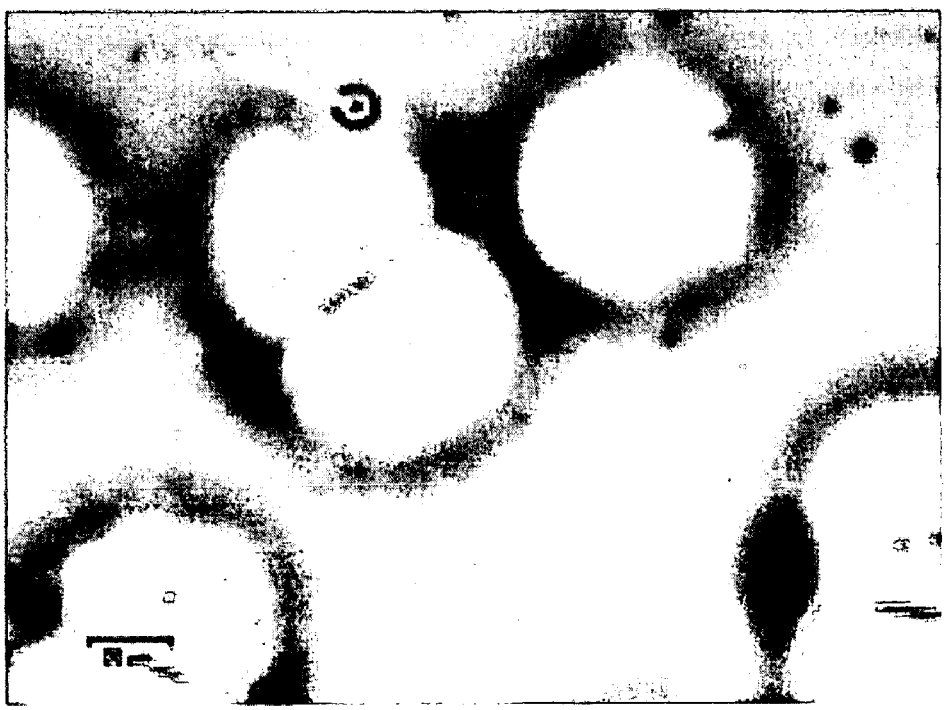
FIG. 10B shows an optical microscope image of 25 nm PS film without Compound 1 of the invention after annealing at 170° C. overnight.

Additionally, 25 nm films having ratios of 3:1 and 0:1 Compound 1:PS were spun cast on silicon wafers, irradiated for 1 hour, and annealed at 170° C. overnight. FIGS. 10A and 10B show optical microscope (OM) images of the 25 nm films having about 3:1 and 0:1 Compound 1:PS, respectively. As shown, 0:1 ratio sample exhibits large hole that are approximately 40 μm in diameter while the 3:1 ratio sample does not show such features.

Figure 11A:
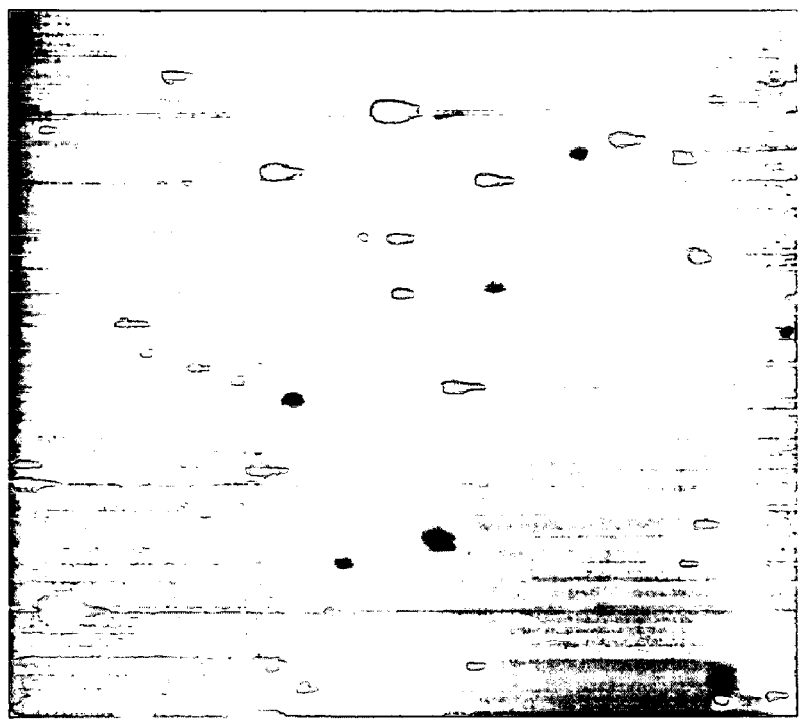
FIG. 11A shows an AFM image of a 7 nm PS film containing Compound 1 of the invention (1:17 ratio of PS:Compound 1) after irradiation and annealing at 170° C. overnight.
Figure 11B:
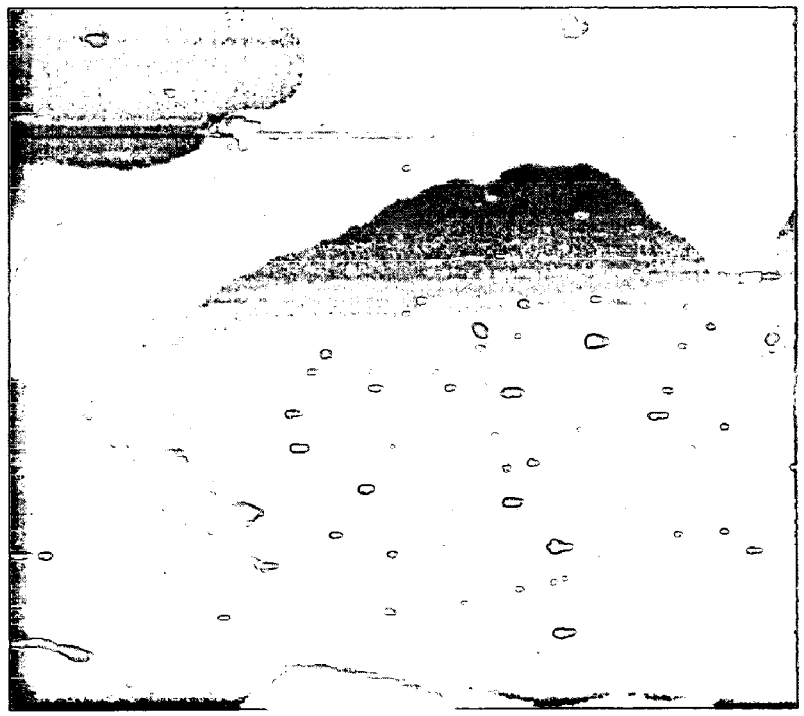
FIG. 11B shows an AFM image of 7 nm PS film without Compound 1 of the invention after annealing at 170° C. overnight.

7 nm films having 17:1 and 0:1 ratios of Compound 1:PS were also spun cast on silicon wafers, irradiated for 1 hour, and annealed at 170° C. overnight. FIGS. 11A and 11B show AFM images of the 7 nm films having about 17:1 and 0:1 Compound 1:PS, respectively. As shown, 0:1 ratio samples exhibit large holes that appear to have formed a ribbon while the 17:1 ratio samples do not show such features. Decreasing the ratio to 8:1 gave similar results. In contrast to the 25 nm film, a ratio of 3:1 is unable to prevent the formation of dewetting morphologies in the 7 nm film as evidenced by OM. 2 nm film also needed higher concentration of Compound 1 to prevent dewetting. Therefore, a greater amount of crosslinker may be utilized to stabilize the thinner films.

Dewetting Upon Exposure to Solvent Vapors

Dewetting of polymer films upon exposure to solvent vapors were also studied. The 7 nm and 25 nm PS films with and without Compound 1 were placed in a flask of saturated toluene vapor at room temperature. The resulting OM images are shown in FIGS. 12A through 13B.

Figure 12A:
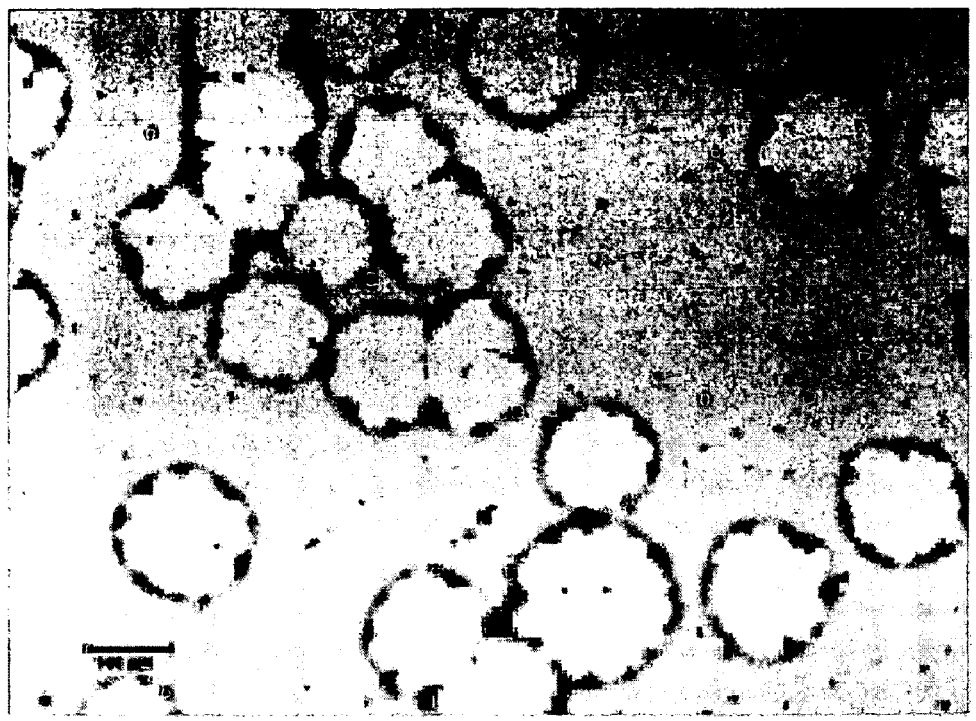
FIG. 12A shows an optical microscope image of a 7 nm PS film containing Compound 1 of the invention (1:18 ratio of PS:Compound 1) after irradiation and exposure to toluene vapor.
Figure 12B:
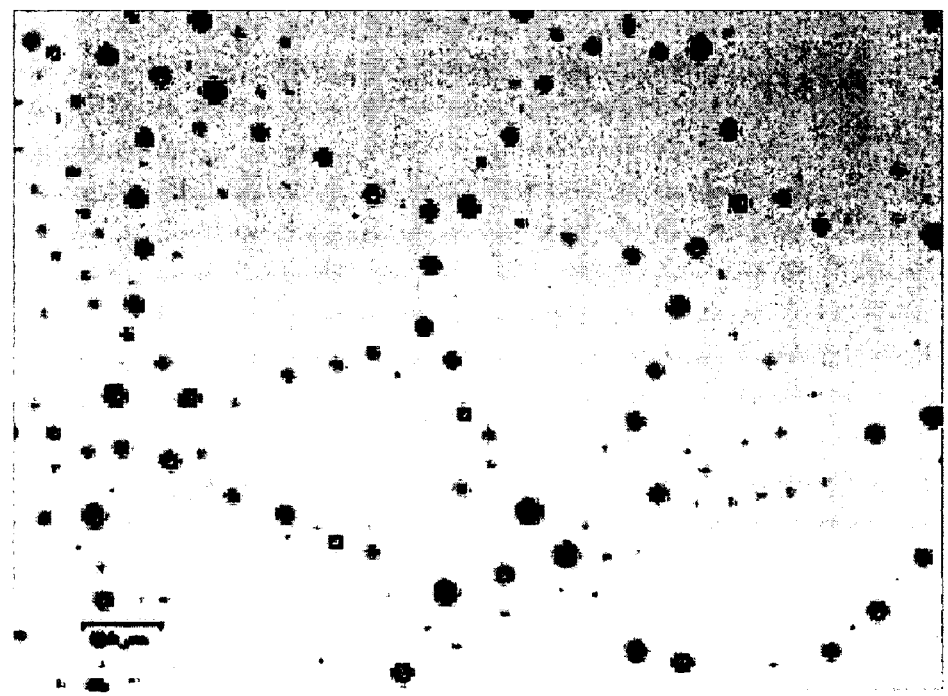
FIG. 12B shows an optical microscope image of a 7 nm PS film without Compound 1 of the invention after exposure to toluene vapor.

FIG. 12A shows a 7 nm PS film containing Compound 1 after irradiation and exposure to vapor. FIG. 12B shows a pure 7 nm PS film after exposure to vapor. Films containing irradiated Compound 1 formed holes whereas films without Compound 1 or unirradiated films containing Compound 1 formed droplets. The droplet formation is suggestive of further progression of dewetting as it is generally considered the final stage of dewetting.

Figure 13A:
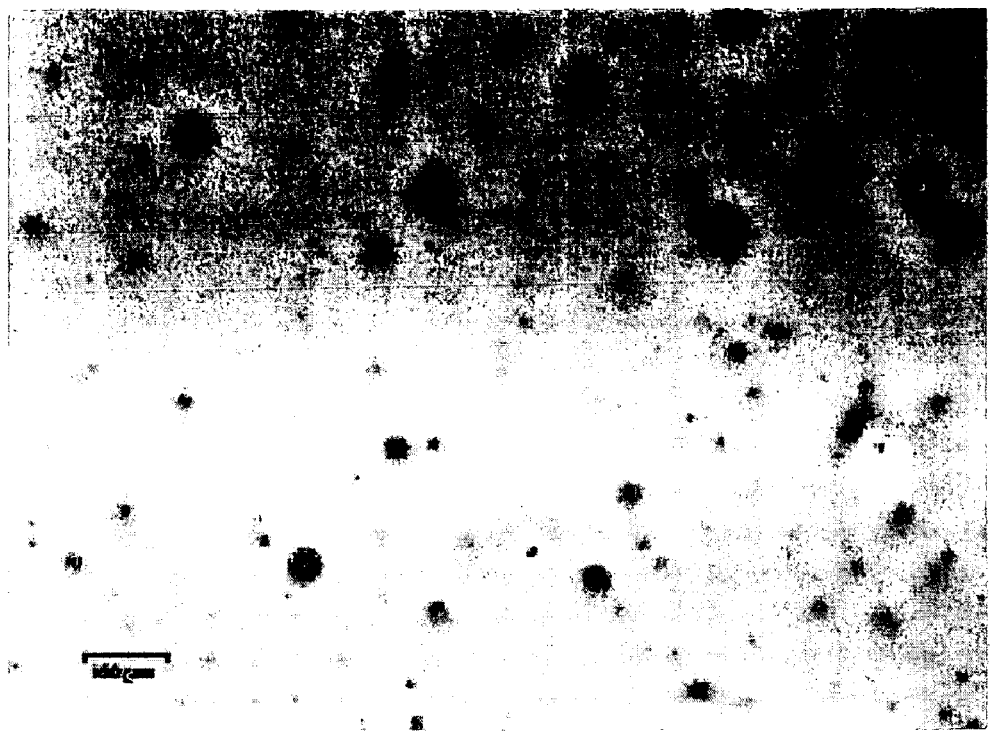
FIG. 13A shows an optical microscope image of a 25 nm PS film containing Compound 1 of the invention (1:4 ratio of PS:Compound 1) after irradiation and exposure to toluene vapor.
Figure 13B:
FIG. 13B shows an optical microscope image of a 25 nm PS film without Compound 1 of the invention after exposure to toluene vapor.

For the 25 nm films, the inhibition of dewetting is more pronounced. FIG. 13A shows an image of a 25 nm PS film containing Compound 1 after irradiation and exposure to toluene vapor. FIG. 13B shows the corresponding pure PS film. Once again, droplet formation is observed in the pure film. Only small imperfections appear in the irradiated film. As the amount of Compound 1 is decreased, the frequency of occurrence of these features decreases. The ability of the photocrosslinked film to inhibit film rupture in response to vapor suggests that the invention may allow stabilizing thin film devices that respond to chemical stimuli, such as surface acoustic wave devices that use polymer films as sensors for detecting vapors.

Dewetting-Resistant PS Films on Other Surfaces

Figure 14A:
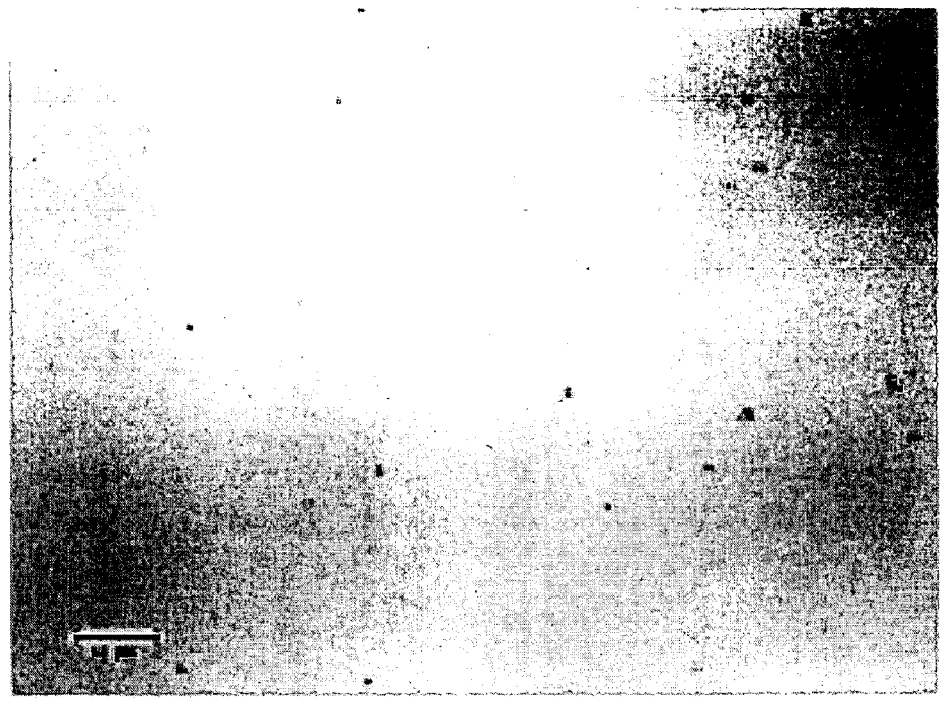
FIG. 14A shows an optical microscope image of a PS film containing Compound 1 of the invention (1:17 ratio of PS:Compound 1) on PMMA after irradiation and annealing at 170° C. overnight.
Figure 14B:
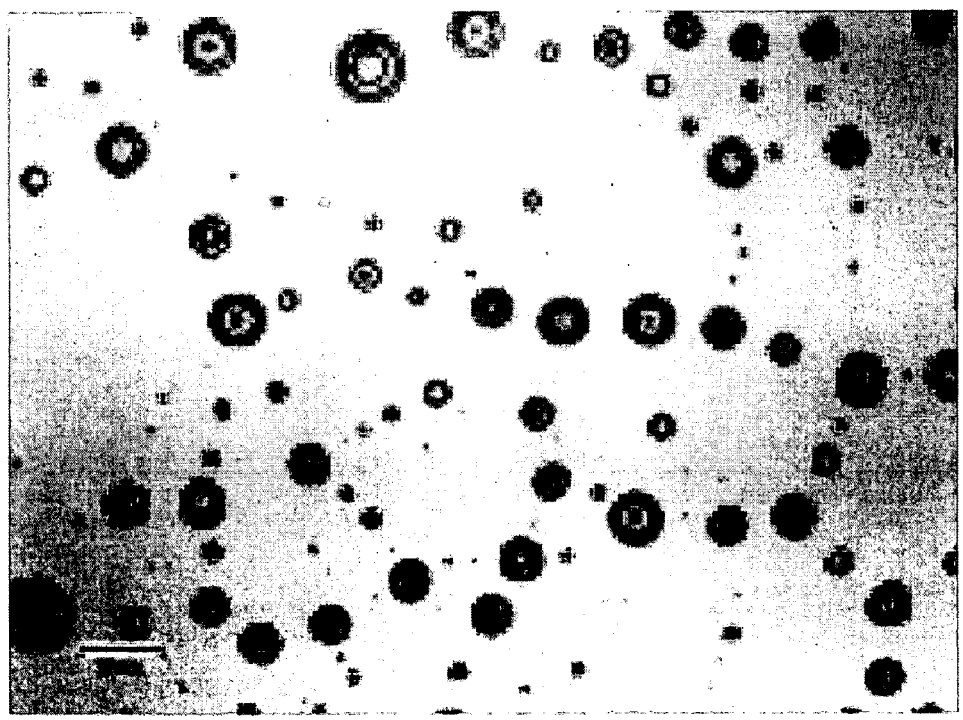
FIG. 14B shows an optical microscope image of a PS film without Compound 1 of the invention on PMMA after annealing at 170° C. overnight.
Figure 14C:
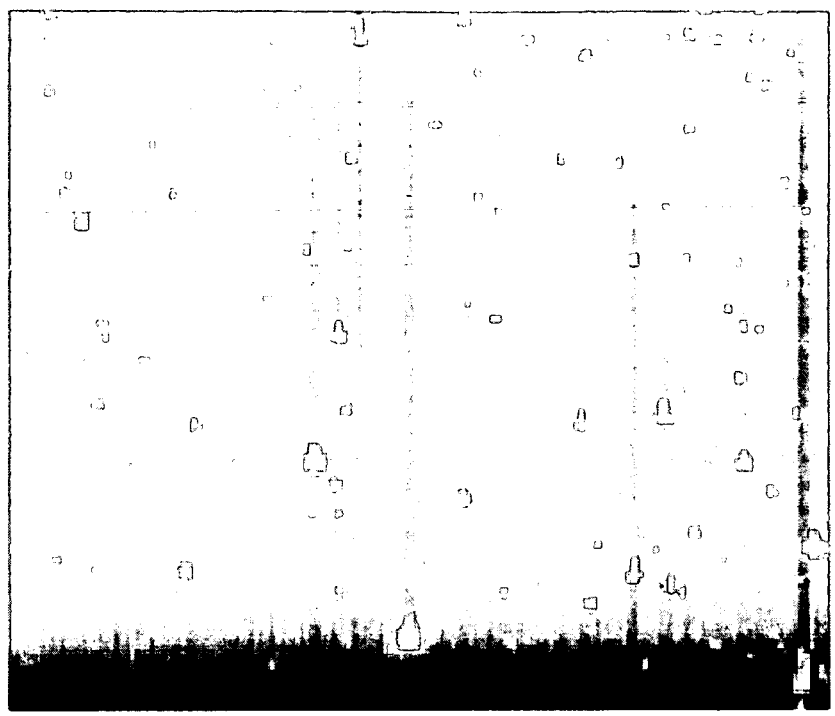
FIG. 14C shows an AFM image of a PS film containing Compound 1 of the invention (1:17 ratio of PS:Compound 1) on PMMA after irradiation and annealing at 170° C. overnight.
Figure 14D:
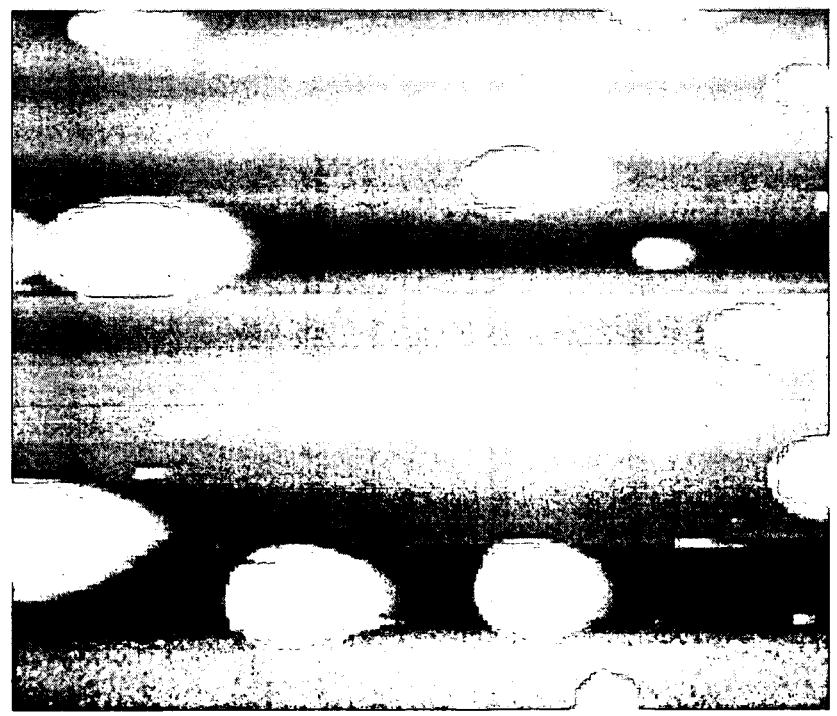
FIG. 14D shows an AFM microscope image of a PS film without Compound 1 of the invention after annealing at 170° C. overnight.

Films of PMMA were prepared on silicon, followed by deposition of a PS film containing Compound 1 (1:17 ratio of PS:Compound 1) on top of the PMMA film. FIGS. 14A and 14B show OM images and FIGS. 14C and 14D show AFM images of PS films on PMMA. As shown in FIGS. 14A and 14C, inhibition of dewetting is observed in the irradiated sample. The average roughness of the crosslinked film is about 0.90±0.1 nm as compared to the uncrosslinked films shown in FIGS. 14B and 14D (16±3 nm). Moreover, the average height of the uncrosslinked film is about 60±18 nm as compared to about 12±8 nm for the crosslinked film. Higher amounts of Compound 1 relative to PS were needed to see a noticeable inhibition of dewetting when compared to that observed on the silicon surface. Without wishing to be bound by theory, this may be attributed to a change in wettability as the contact angle of PS on Si is about 7.5° whereas the contact angle on PMMA is about 11.3°.

Figure 15A:
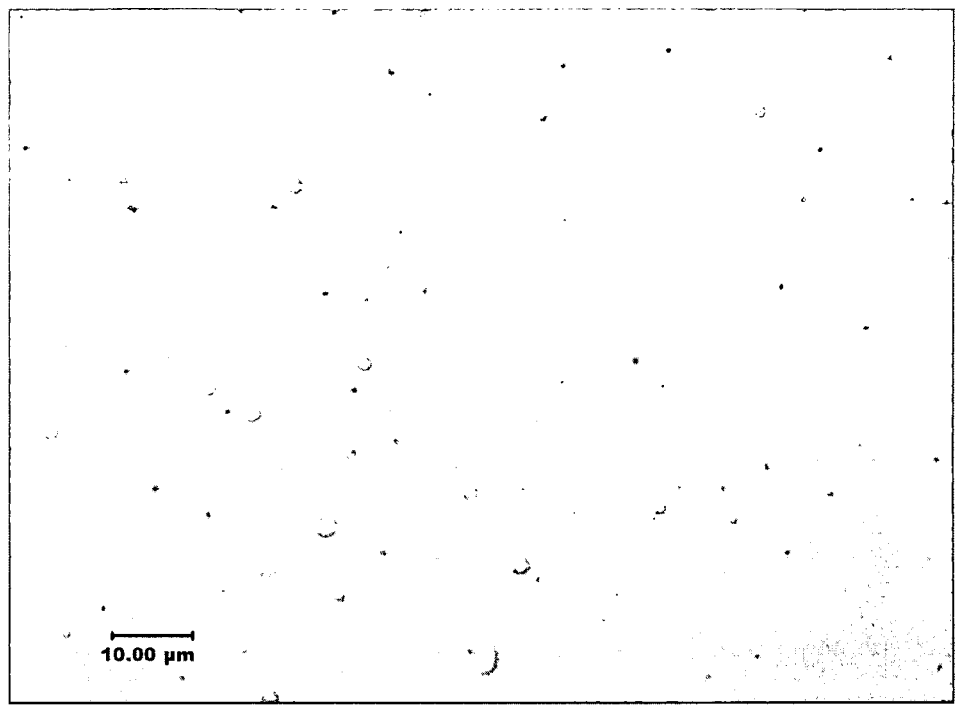
FIG. 15A shows an optical microscope image of an annealed PS film containing Compound 1 of the invention on a 100 nm gold film after irradiation.
Figure 15B:
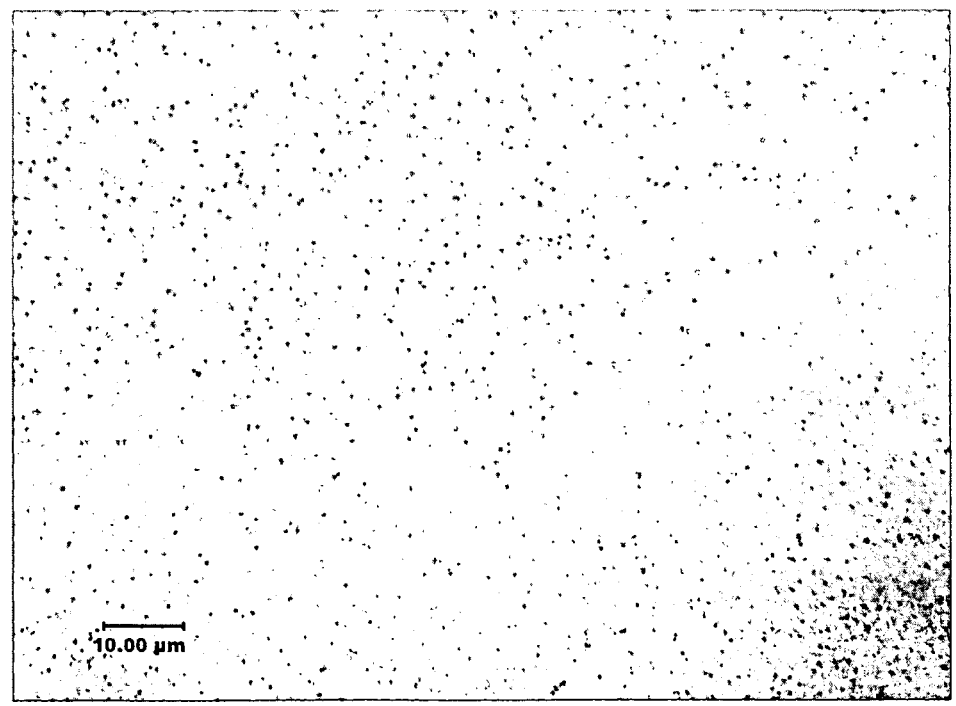
FIG. 15B shows an optical microscope image of an annealed PS film without a photoactive compound of the invention on a 100 nm gold film after irradiation.
Figure 15C:
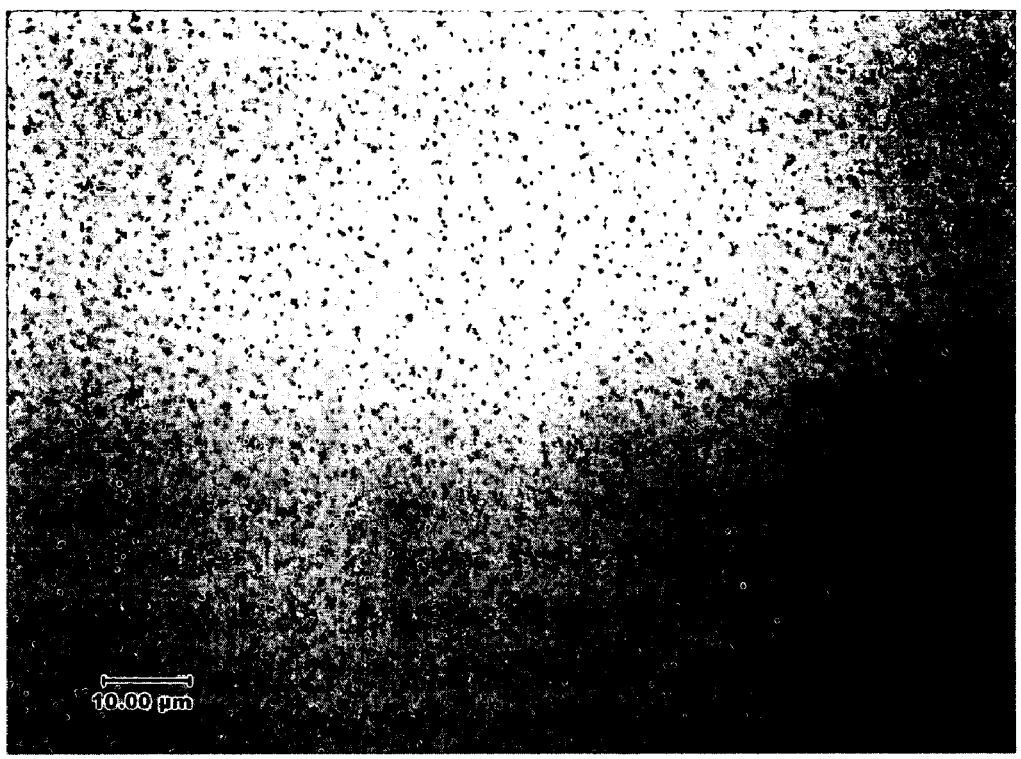
FIG. 15C shows an optical microscope image of an annealed PS film containing Compound 1 of the invention on a 100 nm gold film without irradiation.

100 nm gold film was also formed on silicon, followed by deposition of a PS film containing Compound 1 in the sample on top of the gold film. FIGS. 15A through 15C show OM images of an irradiated sample having Compound 1 (FIG. 15A), an irradiated sample without Compound 1 (FIG. 15B), and an unirradiated sample having Compound 1 (FIG. 15C). As shown, the irradiated sample containing Compound 1 (see FIG. 15A) shows less dewetting than the other two control samples (FIGS. 15B and 15C).

Irradiation Through a Photomask

Figure 16:
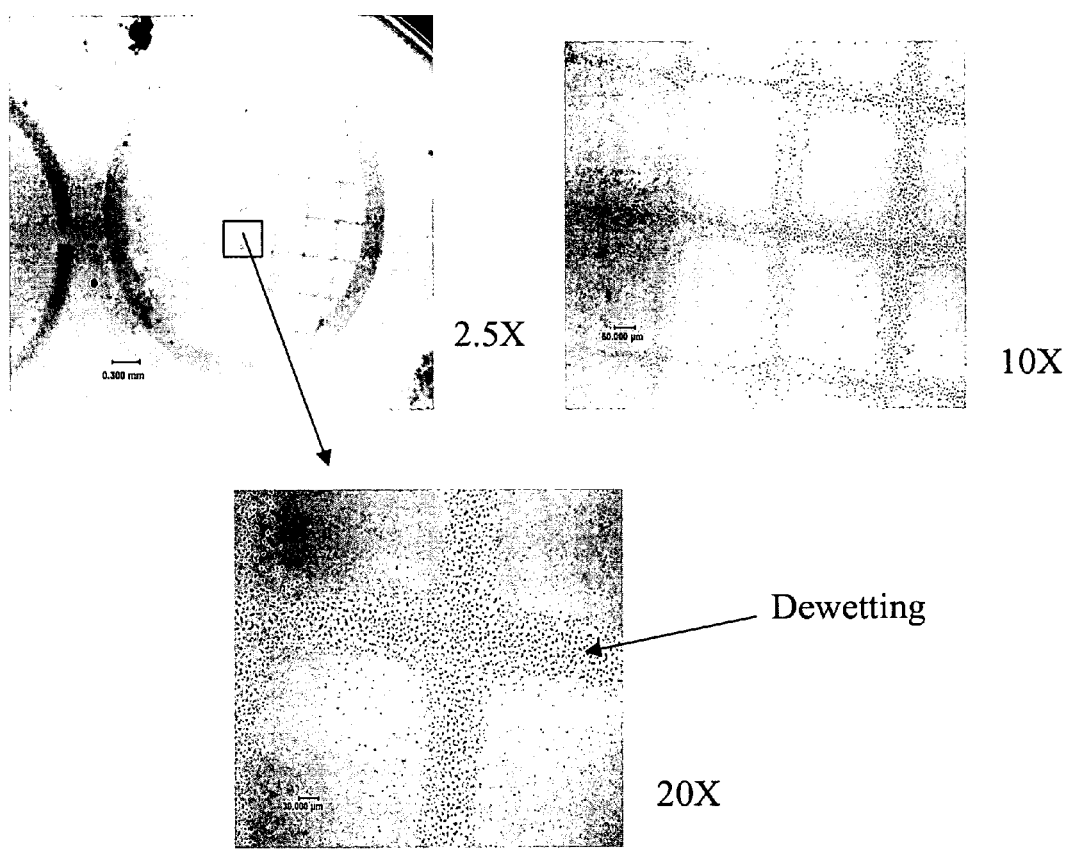
FIG. 16 shows dewetting patterns formed by irradiating a PS film containing Compound 1 of the invention through a photomask, where the dewetting occurs in the masked regions.

Additionally, irradiation was carried out using a photomask. As shown in the OM images of FIG. 16, dewetting occurs in the regions that were masked from irradiation when the sample was heated to about 170° C. The results show that the invention allows for controlling the position of where crosslinks can occur in a thin film.

Example 6

Fabrication of Three-Dimensional Structures

Figure 17:
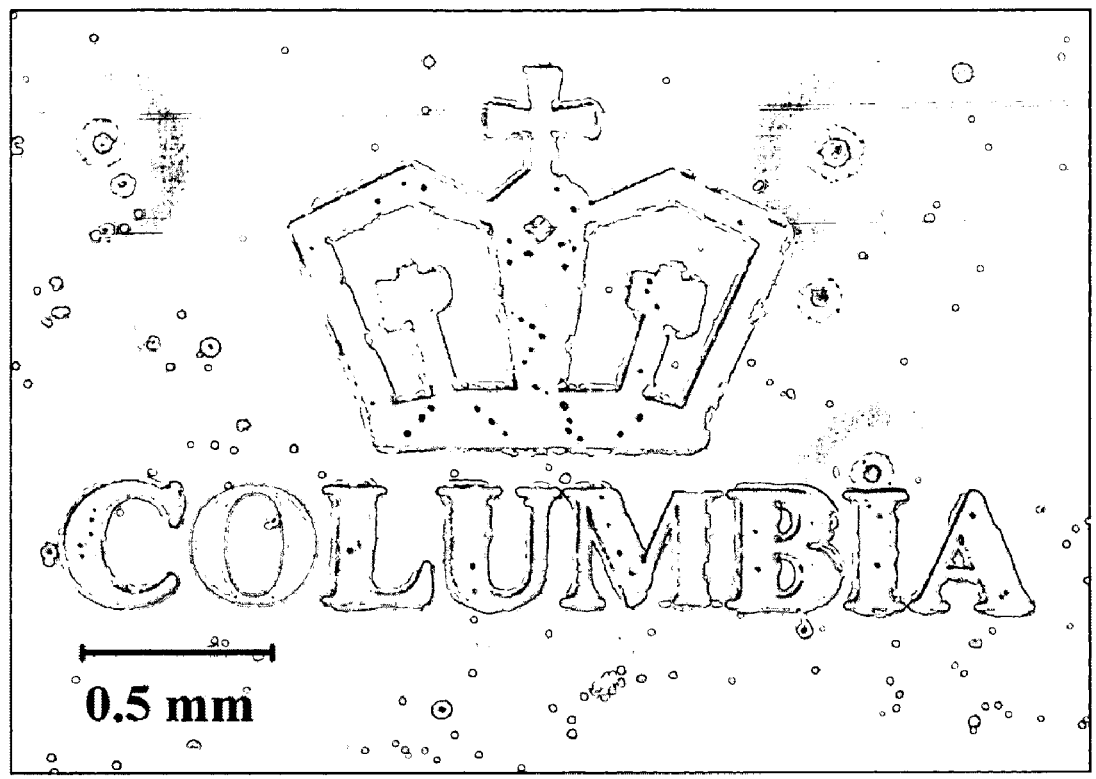
FIG. 17 show an optical microscope image of a PS film containing Compound 1 of the invention irradiated through a photomask followed by annealing above the glass transition temperature, where localized dewetting within the pattern occurs.

In order to pattern PS dewetting morphologies on a surface, a 30 nm thick PS film containing Compound 1 was irradiated through a photomask having Columbia University's crown logo. The film was then heated in a vacuum oven at 170° C. for 5 hours. The resulting pattern is shown in FIG. 17. The light colored regions are regions that have been masked from irradiation. As shown, dewetting is limited only to the unirradiated regions (see dark droplets indicative of dewetting within the crown logo). Interestingly, uncrosslinked polymer collects at the edges of the pattern to form a long ribbon of polymer. Typically, such shapes are unstable and decay due to Rayleigh instabilities. Heating the patterned surfaces overnight did not result in the decay of the shapes. The interface between cross-linked and uncrosslinked polymer appears to stabilize this structure.

Another feature of interest is the preference for droplet formation on the larger masked areas. Both the base of the crown and the middle bar show a more regular presentation of droplets as opposed to the thinner regions of the pattern.

Figure 18:
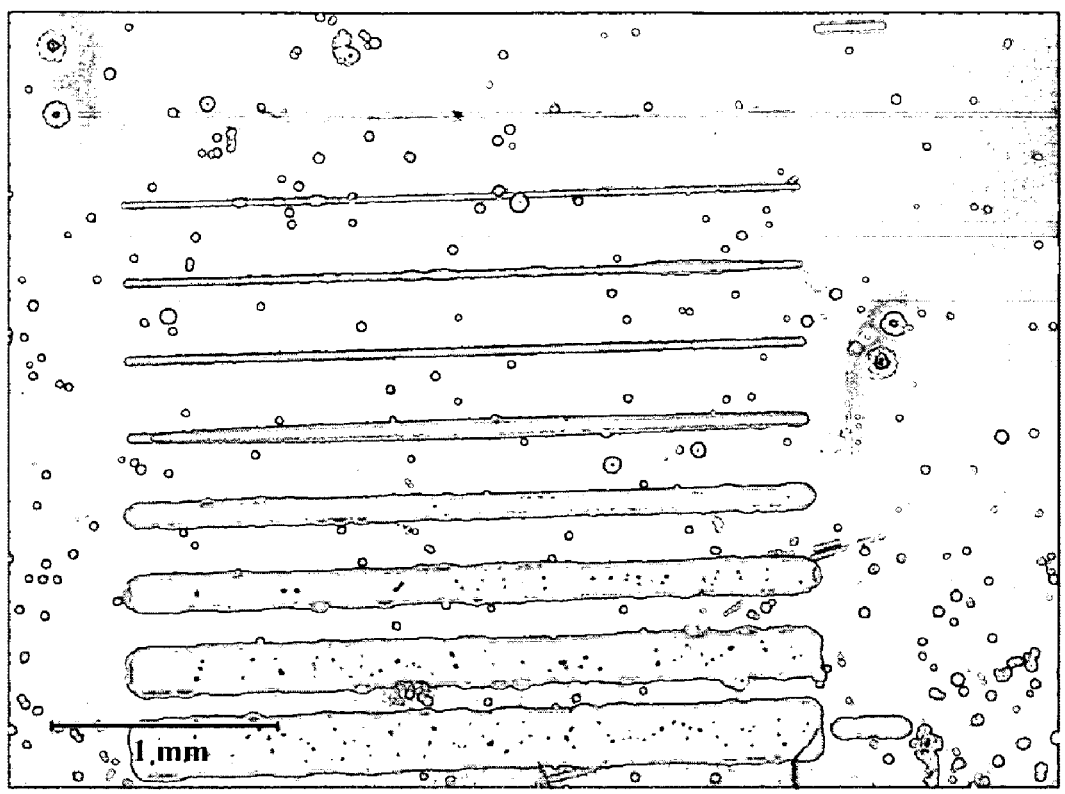
FIG. 18 shows an optical microscope image demonstrating that varying width of the uncrosslinked portions of the film affecting the dewetting behavior.

Microchannels of varying widths were also patterned. Irradiating and heating this sample as above resulted in the pattern shown in FIG. 18. The smallest channel has a width of approximately 20 µm. As described above, the various confinement regimes affect the dewetting behavior on different length scales. When the dewetted region is confined to a width of 47 µm, droplets do not form regularly. The next largest width, 86 µm, shows a regular arrangement of droplets throughout the pattern. The spacing appears to be too small for the typical arrangement of hexagons to develop because the dewetting width is jammed into a volume smaller than the size of the conventional pattern. As the dewetting width increases, the morphology of the ribbon begins to deviate from a straight-edge with bulges appearing regularly throughout.

Figure 19:
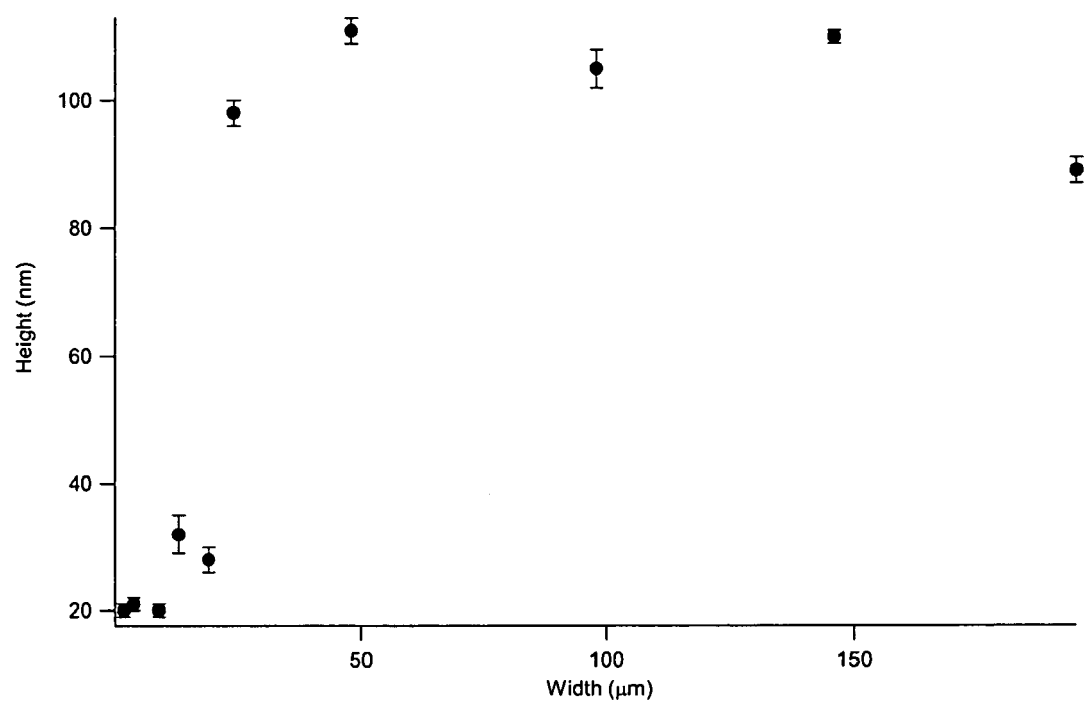
FIG. 19 shows a graph of the height of the channel wall as a function of the channel width.

Another feature of interest is the height of the matter that collects at the wall of the channel. The effect of the channel width on the height of the channel walls is illustrated in the graph in FIG. 19. The height of the walls increased as the width of the channel increases owing to more matter collecting at the interface. In these experiments, the maximum height was approximately 100 µm and was reached when the mask width was 24 µm. Increasing the mask width did not increase the height of the walls beyond 100 µm. The average diameter of a droplet for a film of this thickness is 25±6 µm. The height of the film increases sharply when the size of the pattern in the photomask is in this range. A pattern of 19 µm gives a height of only 28±2 µm.

Figure 20:
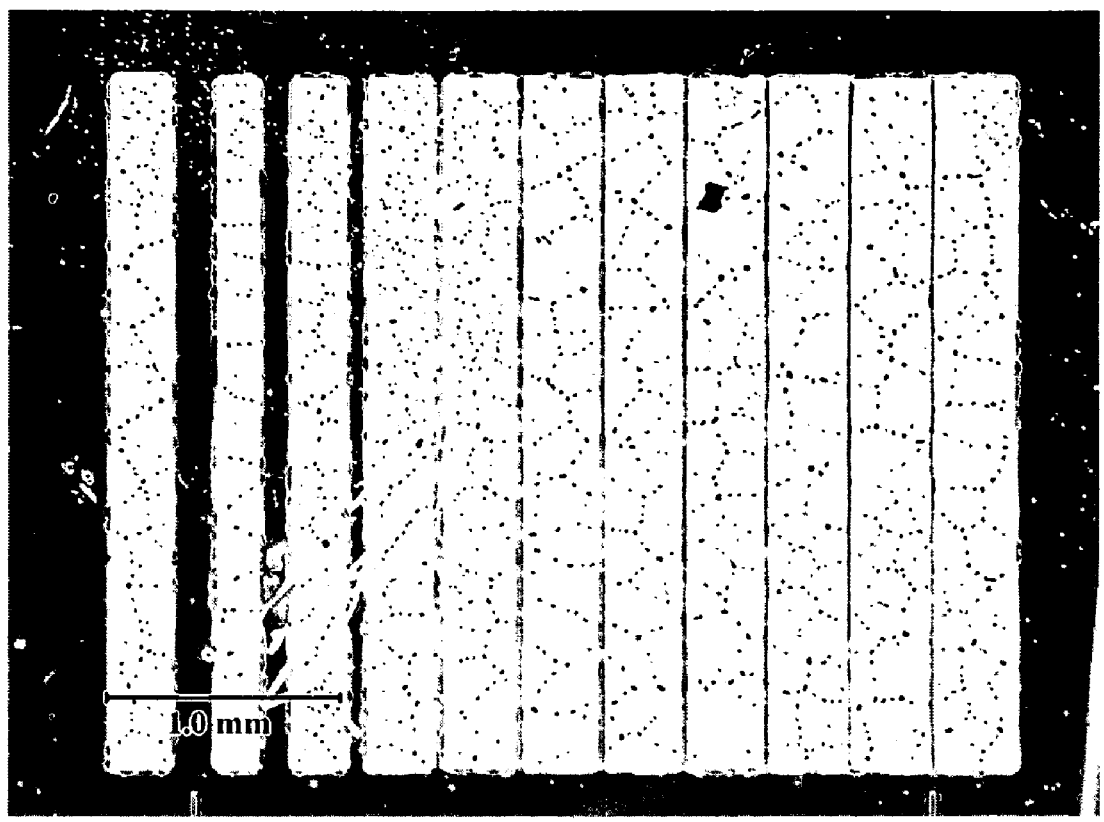
FIG. 20 shows an optical microscope image demonstrating that varying the width of the uncrosslinked portions of the film affects the alignment of droplets within the channel.

FIG. 20 displays a pattern of larger channels. As the width of the channels increase, the droplets evolve towards a polygonal pattern typical of PS dewetting in films of this thickness. As noted above, the width of a typical polygon for this film thickness is 280 ±20 µm. As the width of the dewetting region decreases the pattern formation is disrupted, resulting in branched, zigzag and linear assemblies of droplets. Another feature of interest is the width of the ribbon between the channels. As the width of the cross-linked area is decreased, the width of the ribbon that assembles at the interface decreases. This suggests that the uncross-linked PS localizes itself on the crosslinked PS when heated above $T_g$.

Figure 21A:
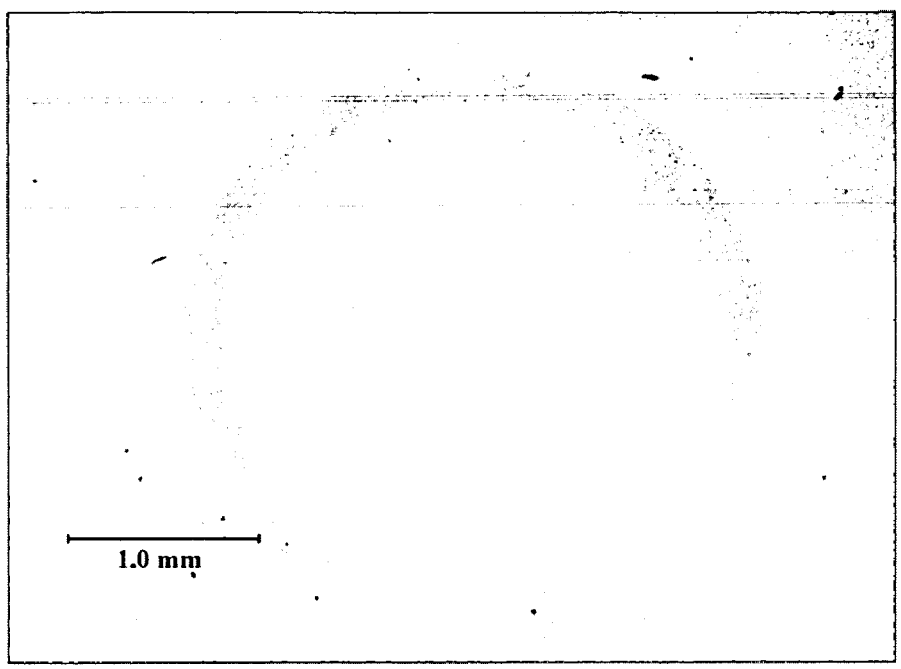
FIG. 21A shows an optical microscope image of the entire pattern of a 7 nm film after irradiation and annealing.
Figure 21B:
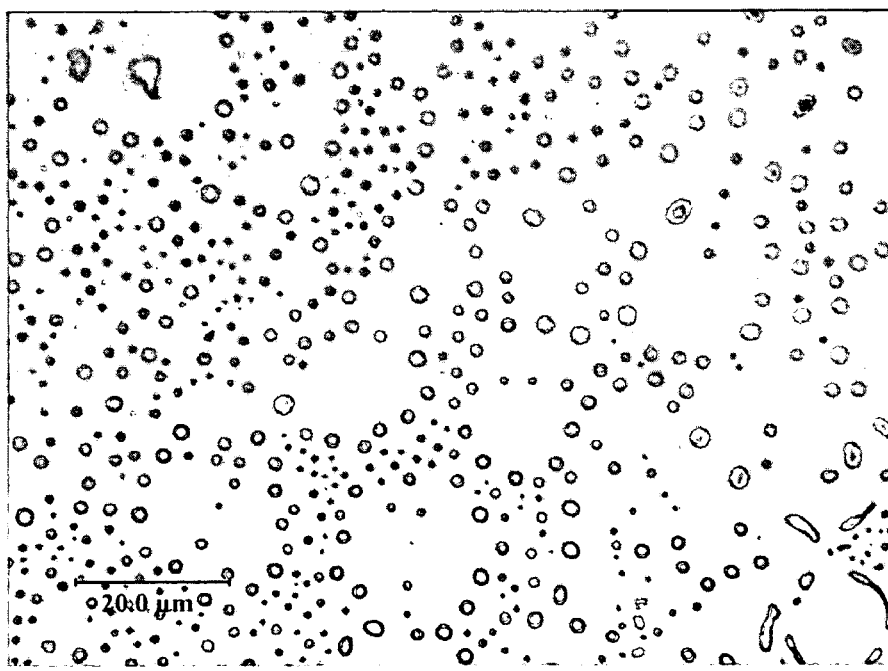
FIG. 21B shows an optical microscope image of the pattern corresponding to the outer rim portion of the photomask for a 7 nm film after irradiation and annealing.
Figure 21C:
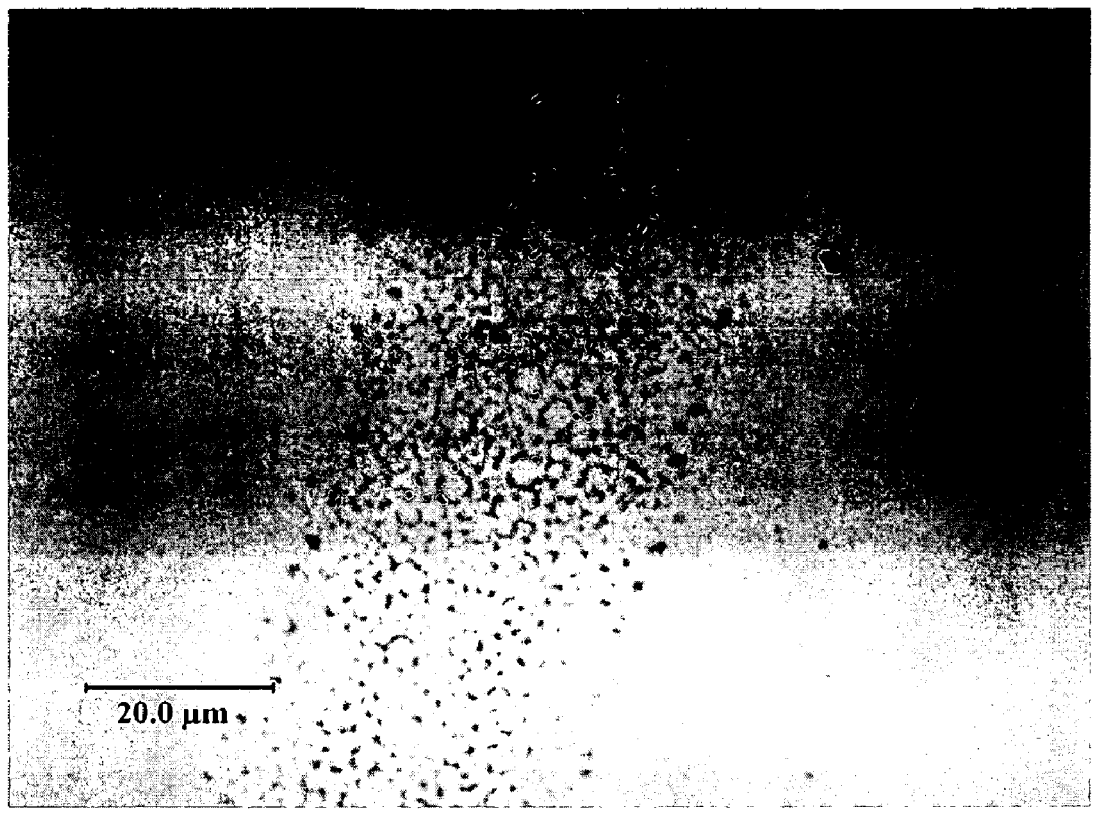
FIG. 21C shows an optical microscope image of the pattern corresponding to the inner bar portion of the photomask for a 7 nm film after irradiation and annealing.

An interesting characteristic of thin polymer films is the change in properties with a change in size. For example, it has been suggested that the mechanism by which dewetting occurs is dependent on the thickness of the film. For films of less than 10 nm, spinodal dewetting has been attributed to the rupture of the film whereas films greater than 10 nm are said to dewet by nucleation onto defect sites. The effect of film thickness on the confined dewetting behavior was examined. FIG. 21A displays an OM image of a patterned 7 nm film treated under the same conditions as above. The matter confined within the bars of the image (FIG. 21B) takes up a different shape than the droplets that appear in the larger circular rim of the pattern (FIG. 21C). The size of the dewetting regions within the checkerboard pattern is approximately 50 µm. The vertical structures at the interface of the crosslinked and uncrosslinked regions did not form for the 7 nm film, as they did for the 30 nm films.

Figure 22:
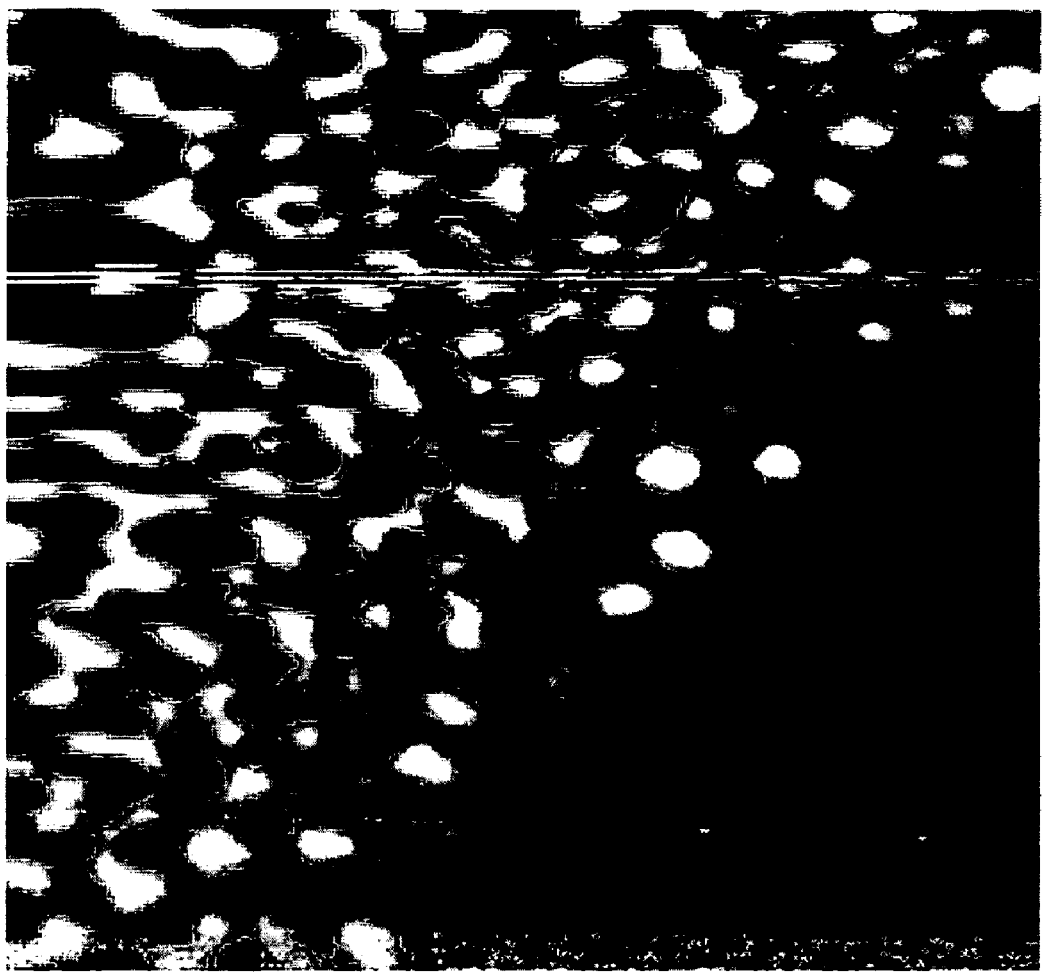
FIG. 22 shows an AFM image of the edge of a pattern in a 7 nm film after irradiation and annealing.

In order to visualize the edge of the pattern we obtained AFM images of the surface. FIG. 22 shows an AFM image of the edge of a channel within a patterned 7 nm film. Three distinct structural regions are evident from this image: 1) the uncrosslinked region showing a bicontinuous spinodal-like pattern, 2) the interphase region between the cross-linked and uncrosslinked film and 3) the smoother crosslinked area. The undulating pattern in the uncrosslinked region is reminiscent of spinodal dewetting. This area of the surface has the greatest amount of surface area and the highest peaks. Peaks as high as 95 nm were found in this region. Heights at least as small as 20 nm were also found within the curved walls. The second area of interest, the interphase region, displays many circular holes. As the interphase bleeds into the uncrosslinked area, the holes grow and coalesce until the undulating pattern is reached. As the interphase region approaches the crosslinked area, the holes shrink and the surface roughness ultimately appears more constant. Our interphase region is analogous to the theoretical interphase between two surfaces in which there is a change in density of material between two distinct phases. Our macroscopic interphase could be a result of a change in crosslink density due to scattering of photons into the edges of the masked region or a change in elasticity as the crosslinked polymer approaches the uncrosslinked polymer. The final area of interest is the crosslinked film. This part of the film resists dewetting and has smaller surface features (approximately 5 nm) compared to the interphase and uncrosslinked phase.

The crosslinked polymer can act as a microvessel/microvial that confines the uncrosslinked polymer to a defined space. Heating such a system above $T_g$ results in the formation of smaller patterns within the larger pattern. The structures of the smaller patterns can be controlled by changing the size of the larger pattern.

Example 7

Photochemical Immobilization of Carbohydrates

In order to create a novel surface suitable for immobilizing carbohydrates, Compound 4 was self-assembled on, glass (ArrayIt), silicon (Wafer World) and quartz (SPI) in anhydrous toluene to produce SAM 4 as follows (see FIG. 3). Substrates and glassware were cleaned by boiling in a "piranha" solution (7:3 sulfuric acid:$H_2O_2$) for one hour followed by an extensive rinse with water and methanol. Substrates were dried with a stream of argon and immersed in a 1 mmol solution of compound 1 in anhydrous toluene (Aldrich). The solution was kept under argon and left undisturbed for twelve hours. The surface was then removed and baked for two hours at 110° C. The resulting self-assembled monolayers were rinsed with toluene and sonicated three times for two minutes each in toluene, toluene:methanol 1:1, and methanol. Substrates were kept in argon-purged vials until further use.

Figure 23:
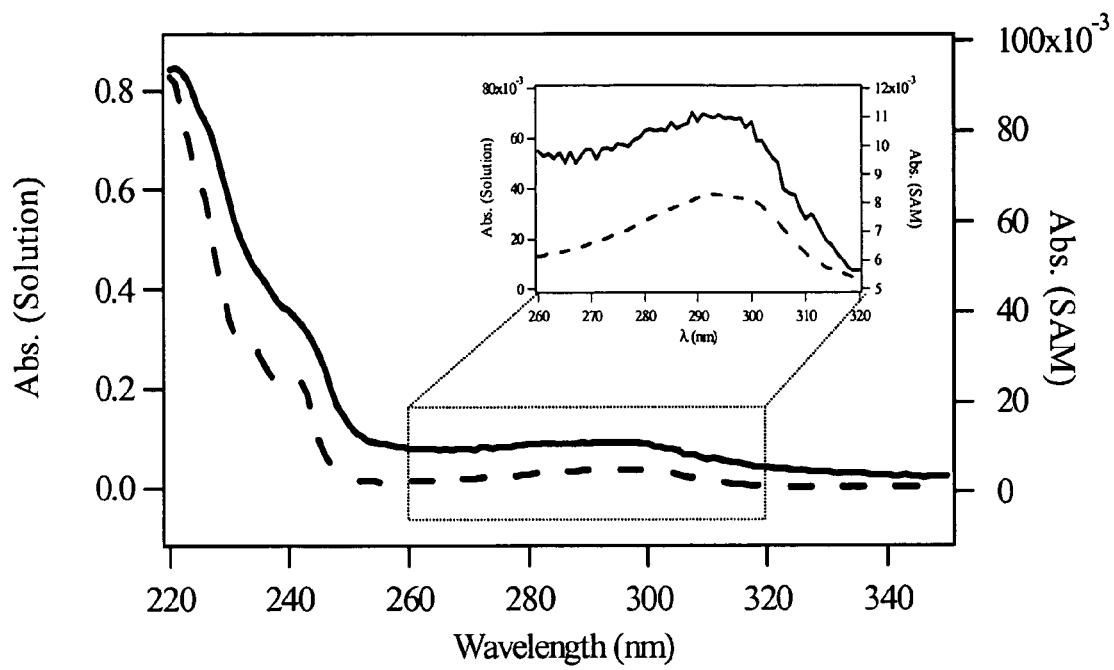
FIG. 23 shows a UV/vis spectra of a photoactive compound in ethanol (dashed line) and a self-assembled monolayer of Compound 4 (SAM 4) on a surface (straight line).

The self-assembly of Compound 4 on the surface was verified by the UV/V is spectroscopy. FIG. 23 shows the UV/V is spectrum of Compound 4 in ethanol (dashed line) and after forming SAM 4 (solid line). Assuming the extinction coefficient of the chromophore on the surface is the same as in solution, the approximate surface coverage was calculated to be 5.5 molecules per $nm^2$. A calculation using Chem3D® suggests about 4.9 aliphatic phthalimides can fit in a space of 1 $nm^2$, a value that is the same order of magnitude as the experimental value, suggesting that SAM 4 is densely packed.

In order to test the ability of surface bound phthalimides to photochemically immobilize sugars, FITC-conjugated polysaccharide films were spin-coated onto SAM 4 and irradiated with a medium pressure mercury lamp in an inert environment (dashed line). The fluorescein isothiocyanate (FITC)-conjugated α(1,6)dextrans weighing 20 kD or 2000 kD (Dextran-FITC) (Sigma) were spin-coated from a 10 mg/ml aqueous solution at 3000 RPM for 90 seconds and placed in argon purged quartz tubes. Irradiation was carried out with a Rayonet Photochemical Reactor equipped with lamps that emit at 300 nm. For ellipsometry and fluorescence experiments, the surface was rinsed by placing in $H_2O$ for 12 hours followed by rinsing with methanol. Substrates were blown dry with argon.

Figure 24:
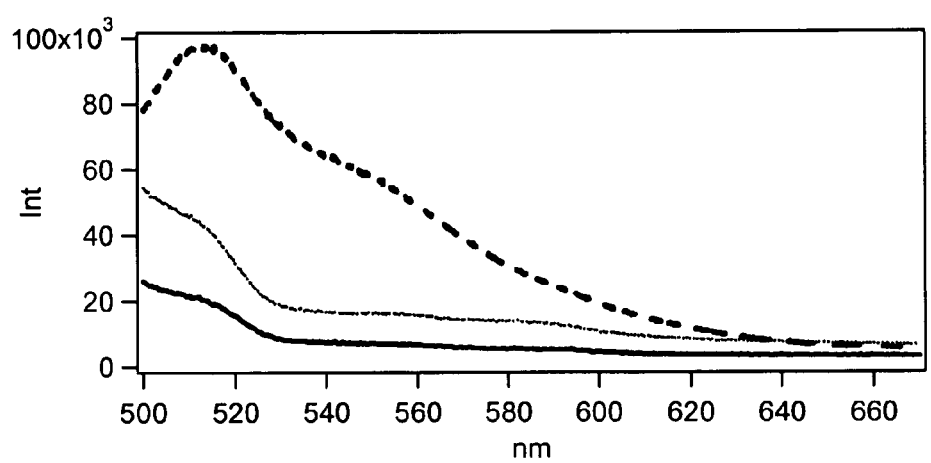
FIG. 24 shows a fluorescence spectra of 2000 kDA FITC-conjugated α(1,6)dextran films under three conditions; irradiated SAM 4 (dashed line), unirradiated SAM 4 (dotted line), and underivatized silicon (straight line). Each spectrum was obtained after washing the surfaces for twelve hours in water.

Two controls were also prepared similarly as described above. In the first, polysaccharides were spin-coated onto SAM 4 and left in the dark (dotted line). In the second, polysaccharides were spin-coated onto an underivatized silicon wafer (straight line). All three samples were placed in water filled vials for twelve hours. After removing the samples and rinsing with water and methanol followed by blow-drying with argon, the fluorescence spectra of each sample were obtained as shown in FIG. 24. Preferential retention of polysaccharides on the irradiated sample relative to the two controls indicates photochemical immobilization of the polysaccharides on SAM 4.

The film thicknesses of the three samples were measured using a Beaglehole ellipsometer in variable angle mode. A refractive index value of 1.5 was used for the organic layer. As shown in Table 1, the irradiated sample retains 7.1±0.3 nm of material after the rinse. The thickness of the material on the SAM kept in the dark was 0.7±0.3 nm and the thickness on the underivatized silicon wafer was 0.4±0.3 nm. The reported thicknesses do not include the thickness of the SAM (1.2 nm). The surfaces were further investigated with water contact angle measurements. The hydrophilic nature of the sugars reduced the water contact angle from 65±1° to 28±1° on the irradiated SAM. Inefficient immobilization on the dark control is evident from a post-rinse contact angle of 62±1°. The higher retention of material on the irradiated SAM demonstrates that self-assembled phthalimide monolayers are capable of photochemically bonding to an overlayer carbohydrate film despite any spatial restrictions on the chromophore as a result of placement in a constrained environment. We speculate that the nature of the bonding is covalent and results from radical-radical combination following hydrogen abstraction.

TABLE 1

Thickness and $H_2O$ contact angles of photochemically grafted polysaccharide films after rinsing with $H_2O$ for 12 hours.

| Sample | Thickness after Rinse (nm) | Contact Angle Before Casting Carbohydrate Film | Contact Angle After Rinse |
| --- | --- | --- | --- |
| Compound 2 SAM 2/Sugars/hv | 7.1 ± .3 | 65 ± 1° | 28 ± 1° |
| Compound 2 SAM 2/Sugars/dark | 0.7 ± .3 | 65 ± 1° | 62 ± 1° |
| No SAM/Sugars | 0.4 ± .3 | 65 ± 1° | 23 ± 1° |

The above experiments were also performed on self-assembled monolayers having benzophenone chromophores, another class of aromatic carbonyls that can photochemically abstract hydrogen from C—H groups and have been shown to graft polymers to surfaces. The resulting carbohydrate film thickness and fluorescence intensity were lower and the contact angle was higher than the films on SAM 4. Without wishing to be bound by theory, the lower performance may be due to the radical center in the benzophenone SAM occurring further from the surface than in the phthalimides, self-quenching of the excited state or a higher interfacial tension between the more hydrophobic benzophenone monolayer and the carbohydrate film in comparison to the phthalimide-carbohydrate interaction. Benzophenone SAMs have more hydrophobic character than SAM 4 (phthalimide SAM) as evidenced by a higher water contact angle of about 85°. Preliminary experiments with a microarray spotter have shown that hydrophilic surfaces are more easily spotted than hydrophobic surfaces. In any case, other photoactive carbonyl groups capable of abstracting hydrogen atoms can be substituted and may enhance or retard the reaction due to the efficiency of self-assembly, steric and energetic constraints.

Figure 25:
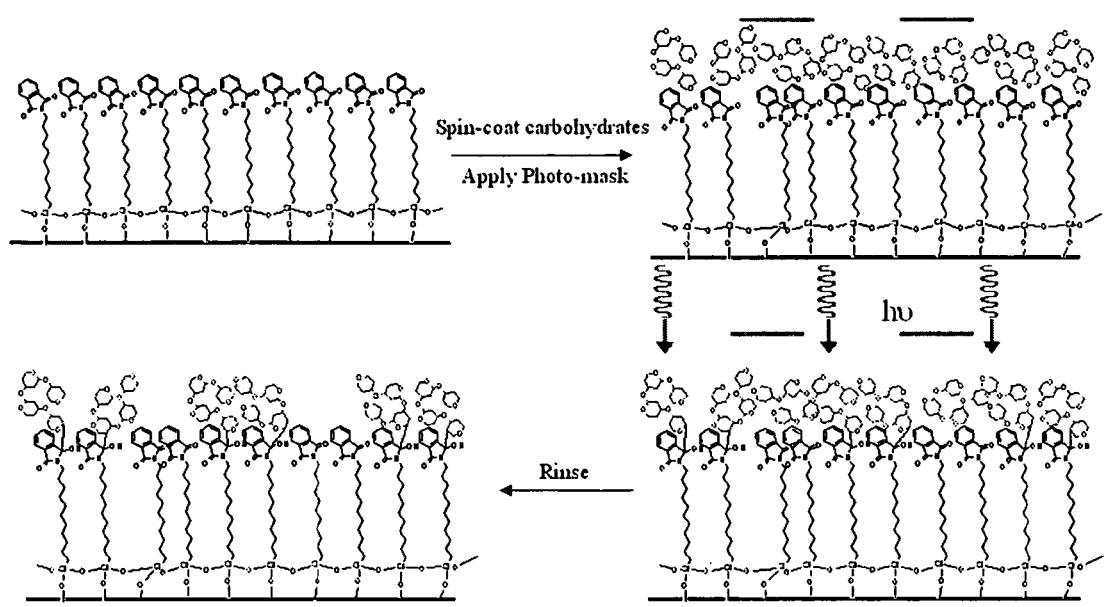
FIG. 25 shows a schematic illustration for direct chemical patterning of a surface with carbohydrates using a photolithographic technique.

In addition to covalently attaching underivatized sugars to a surface, patterns of grafted sugars were also generated, which is schematically shown in FIG. 25. A 75 mesh TEM grid (Electron Microscopy) was used as a photo-mask for all patterning experiments. Dextran-FITC 2000 kD and 20 kD polysaccharide films were prepared as described above. Glucose (Aldrich) was spin-coated from a solution of 26 mg in 1 ml of acetonitrile at 3000 RPM for 90 seconds. One drop of a sucrose (Aldrich) solution containing 1.5 g in 1 ml $H_2O$ was placed on a surface using a pipette. Approximately ¾ of the drop was removed with a pipette. In all cases, the photomask was placed on top of the carbohydrate film or droplet and pressed down with a quartz plate. Irradiation was carried out in an argon filled glove box with a desktop lamp containing a 300 nm Rayonet lamps for approximately 2 hours. The photoreaction was restricted to the transparent regions of the mask leaving the pattern of the mask written to the surface via attached carbohydrates. Samples were rinsed by sonicating in $H_2O$ for 15 minutes, changing the water and vial every 5 minutes. Sonication was accompanied by extensive rinsing with water and methanol. Samples were blown dry with argon.

Figure 26A:
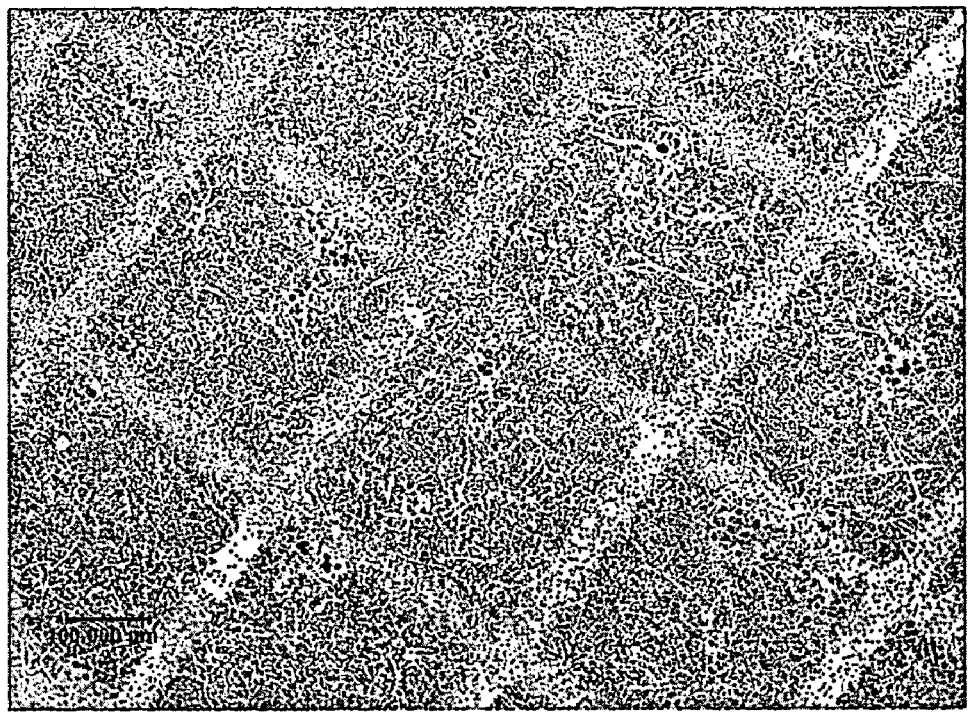
FIGS. 26A and 26B show water condensation experiments after patterning a surface with immobilized carbohydrates, where water is attracted to the hydrophilic carbohydrate coated regions.
Figure 26B:
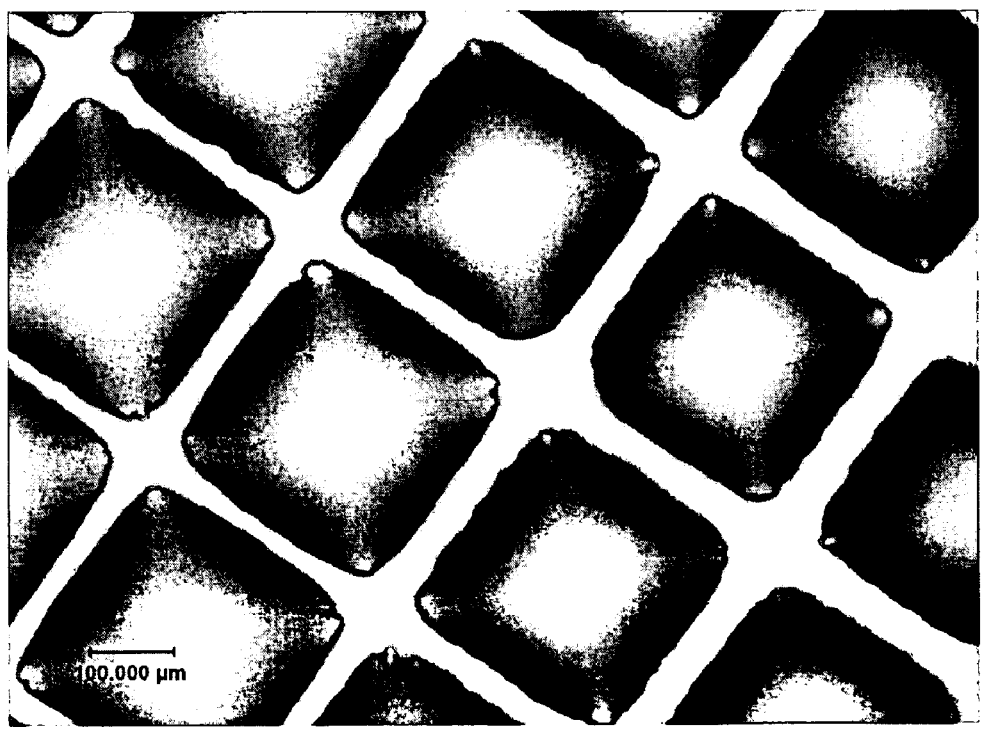

Patterns were visualized by condensing water onto the pattern and imaging with a Nikon Eclipse optical microscope equipped with an INSIGHT digital camera. Two methods were used to condense water onto the surface. In the first, the surface was exposed to an extended breath. In the second, the surface was held over boiling water. FIGS. 26A and 26B show water condensation images of the resulting patterns obtained from polysaccharides with a molecular weight of 2000 kD. FIG. 26A was obtained by breathing onto the sample and FIG. 26B was obtained by holding the sample over a beaker of boiling water for approximately 15 seconds. In both cases, hydrophilic attraction between water and the polysaccharides relative to the unmodified masked regions of the monolayer causes water to preferentially reside on the areas of the surface containing polysaccharide. The results were similar when 20 kD polysaccharides were patterned.

Figure 27A:
FIGS. 27A and 27B show breath condensation experiments after patterning a surface with immobilized sucrose (FIG. 27A) and glucose (FIG. 27B).
Figure 27B:
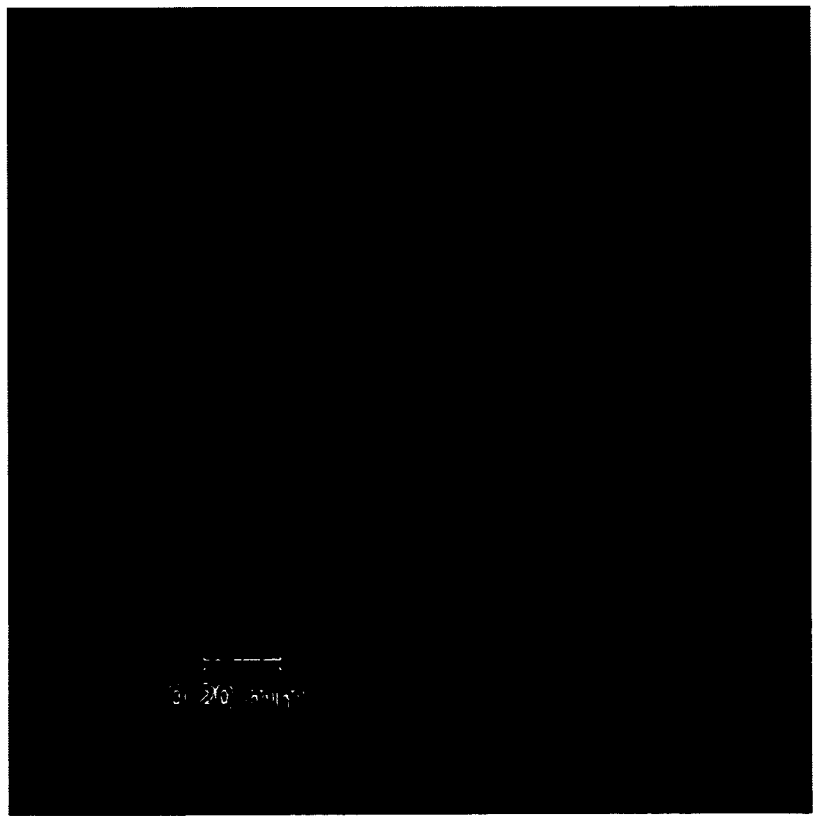

As described above, other studies suggested that the immobilization efficiency decreases with the decreasing molecular weight of the carbohydrate. In order to show the versatility of the invention, glucose and sucrose, two simple sugars at the extreme of low molecular weight containing both six and five member carbohydrate moieties, were tested. The resulting water condensation images are presented in FIGS. 27A and 27B. The visible patterns show that the invention is capable of immobilizing sugars of the lowest molecular weights.

As shown, the invention requires no chemical modification of the sugars prior to deposition. Further, because covalent attachment is involved, sugars of all molecular weights can be immobilized, whereas sugars of lower molecular weights were more prone to be washed away in the conventional art. The photochemical nature of the technique allows simple arrays to be created without a robot and makes the method adaptable to the full potential of photolithography, which is currently used in industry for the high-throughput fabrication of computer chips and nanoscale patterning. Multiple carbohydrate patterns can be immobilized by repeating the reaction with a different carbohydrate in a previously masked region. In conjunction with a microarray spotter, large libraries of carbohydrates can be immobilized on surfaces. The versatility and ease of the method provides an opportunity for biologists, chemists and engineers to investigate and create new biological materials.

Instrumental Measurements

UV-vis spectra were obtained using a Shimadzu (UV-2401 PC) UV-vis recording spectrophotometer. Contact angle measurements were performed with a Rame-Hart 100-00 contact angle goniometer using Millipore Milli-Q water. At least three droplets were measured on each sample and averaged. Thicknesses were measured with a Beaglehole ellipsometer in variable angle mode. A refractive index of 1.5 was used for all samples. Measurements were performed three times in different locations on the surface and averaged. Fluorescence spectra were obtained using a Jobin Yvon Fluorolog 3 spectrofluorimeter in front face mode. The surface was placed at an angle of 20° to a line parallel to the plane of the detector.

Example 8

Fabrication of Mixed Monolayers

Figure 28A:
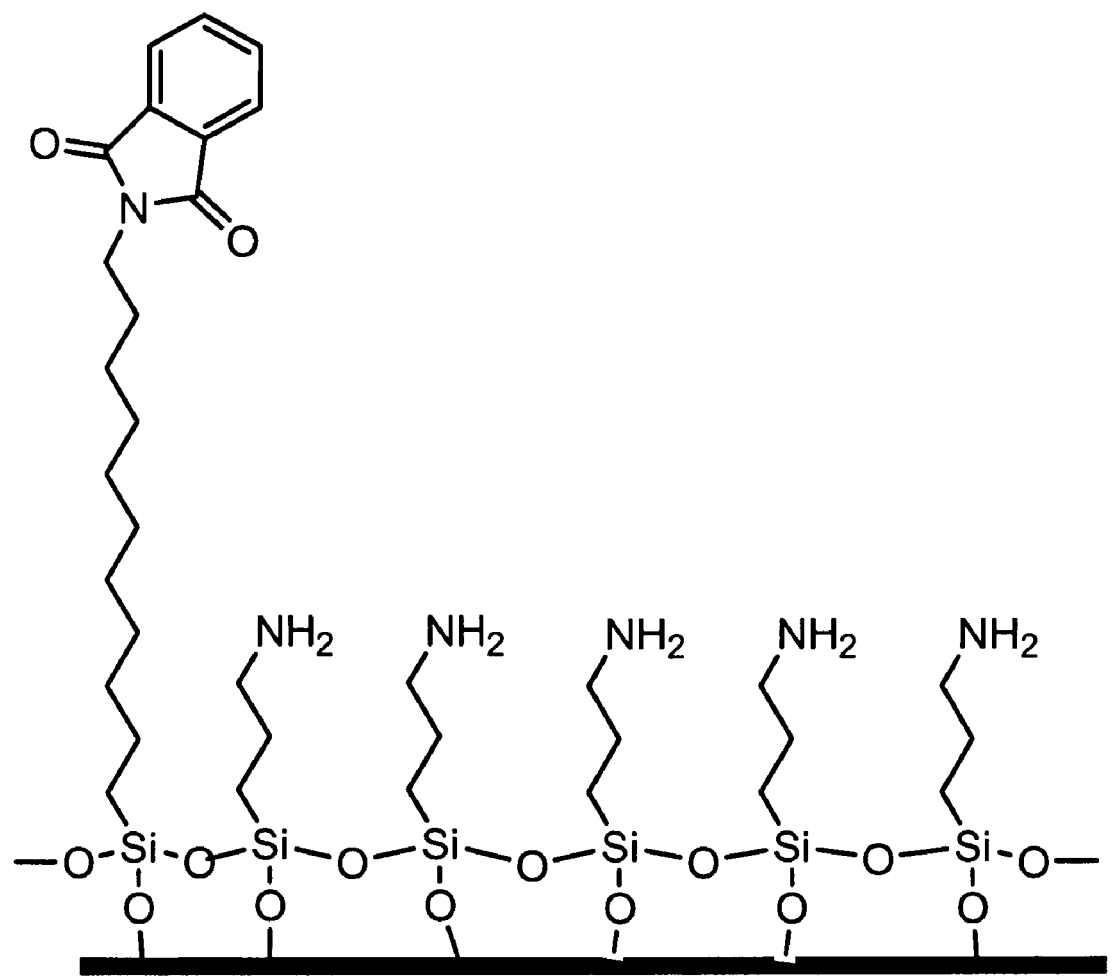
FIG. 28A shows a self-assembled mixed monolayer (SAM 4A or 4B) of the invention.

As schematically shown in FIG. 28A, mixed monolayers were formed from a solution containing a 5:1 ratio of aminopropyltrimethoxy silane to Compound 4 (SAM 4A). SAM 4A was made in the same manner as SAM 4, except that a 5× molar amount of aminopropyltrimethoxy silane (Gelest) was simultaneously added with Compound 4. The contact angle of the resulting surface was 72±1°. Without wishing to be bound by theory, the hydrophilic amine group can interact more favorably with the carbohydrates as compared to the more hydrophobic phenyl ring of Compound 4, decreasing the interfacial tension between the carbohydrate and the surface, and allowing for increased amounts of carbohydrates to be adsorbed to the surface for subsequent photo-immobilization. It should be noted that SAM 4A may be a multilayer rather than a monolayer.

Microarrays were robotically prepared as follows. Antigen preparations were dissolved in saline (0.9% NaCl) at a given concentration and were spotted as triplet replicate spots in parallel. The initial amount of antigen spotted was 0.35 ng per spot and diluted by serial dilutions of 1:5 thereafter (See also microarray images inserted in FIG. 19). A high-precision robot designed to produce cDNA microarrays (PIXSYS 5500C, Cartesian Technologies Irvine, Calif.) was utilized to spot carbohydrate antigens onto chemically modified glass slides as described. Both FAST Slides (Schleicher & Schuell, Keene, N.H.) and SAM 4A slides were spotted. The printed FAST slides were air-dried and stored at room temperature. The printed SAM 4A slides were subjected to UV irradiation in order to activate the photo-coupling of carbohydrates to the surface.

After microarray spotting, the SAM 4A slides were air-dried and placed in a quartz tube. The sealed tube was subsequently purged with argon or nitrogen before irradiation. UV irradiation was conducted by placing the quartz tube under a desktop lamp containing a 300 nm Rayonet bulb for one hour. Precaution was made to avoid skin and eye contact with the radiation during the irradiation process.

Figure 29A:
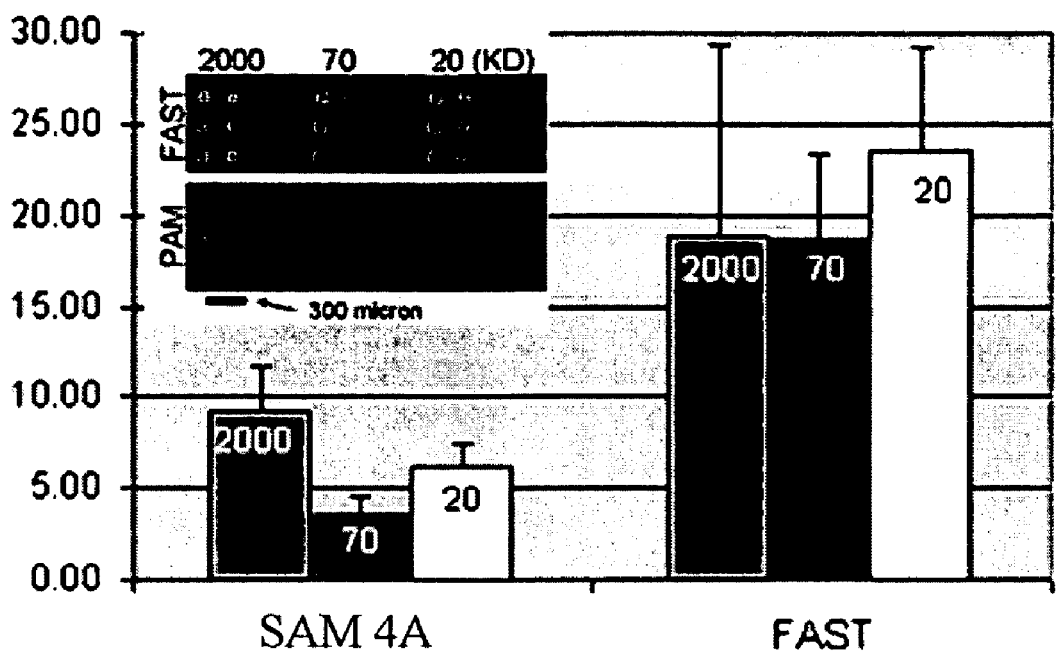
FIG. 29A shows a comparison of fluorescence emitted from a microarray containing spotted carbohydrates attached to SAM 4A and nitrocellulose coated surfaces (FAST) without further treatment.
Figure 29B:
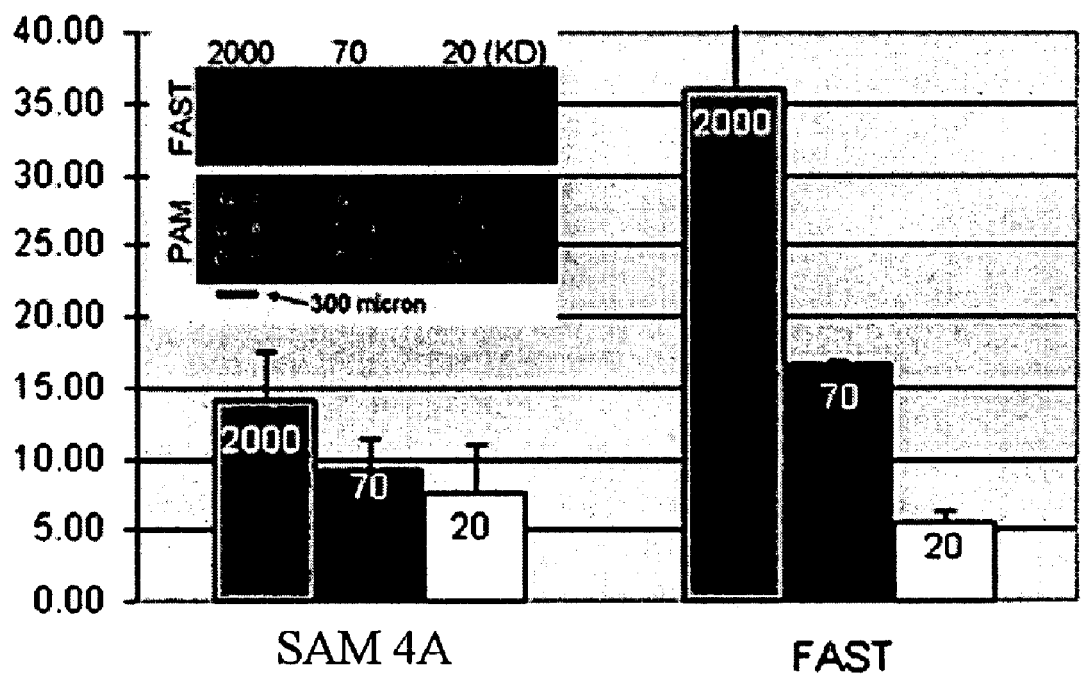
FIG. 29B shows a comparison of fluorescence emitted from a microarray containing spotted carbohydrates attached to SAM 4A and nitrocellulose coated surfaces (FAST) after depositing a specific anti-carbohydrate monoclonal antibody.

FIGS. 29A and 29B show the results after spotting SAM 4A using three fluorescein isothiocyanate (FITC)-conjugated α(1,6)dextrans with molecular weights (MWs) of 20, 70 and 2000 kDa, respectively. In these experiments, the amount of polysaccharides spotted on the surfaces was monitored by measuring the FITC signals associated with the carbohydrate arrays before irradiation (see FIG. 29A). By examining the fluorescent signals before treatment (FIG. 29A), it was determined that the amounts of carbohydrates adsorbed onto SAM 4A after spotting are significantly less than those spotted on the FAST slide. Without wishing to be bound by theory, this may be attributed to the two-dimensional nature of SAM 4A, which allows less polysaccharides to be delivered and adsorbed in comparison to nitrocellulose surfaces that involve thicker three-dimensional coatings.

Then, the printed microarrays were rinsed and washed with PBS (PH 7.4) and with 0.05% Tween 25 times with five minutes of incubation in each washing step. They were then "blocked" by incubating the slides in 1% BSA in PBS containing 0.05% NaN3 at room temperature (RT) for 30 minutes. Antibody staining was conducted at RT for one hour at given dilutions in 1% BSA PBS containing 0.05% $NaN_3$ and 0.05% Tween 20. Determination of immobilized polysaccharides on the surface after irradiation and extensive washing was performed by staining the arrays using a biotinylated anti-α(1,6)dextran monoclonal antibody, 16.4.12E. This antibody is specific for the terminal non-reducing end epitopes displayed by all three dextran-conjugates immobilized on the surface. Since a biotinylated anti-dextran antibody (mAb 16.4.12E) was applied in this study, streptavidin-Cy3 conjugate (Amersham Pharmasia) with wavelengths of excitation and emission at 552 and 570 nm, respectively, was applied to reveal the bound anti-dextran antibodies. The stained slides were rinsed five times with PBS and with 0.05% Tween 20 after each staining step. A ScanArray 5000A Standard Biochip Scanning System (PerkinElmer, Torrance, Calif.) equipped with multiple lasers, emission filters and ScanArray Acquisition Software was used to scan the microarray. Fluorescence intensity values for each array spot and its background were calculated using ScanArray Express (PerkinElmer, Torrance, Calif.). A nitrocellulose substrate (FAST), an established platform, was similarly treated to provide a comparative data.

The results illustrated in FIG. 29B demonstrate that SAM 4A retains a similar amount of material regardless of the molecular weight of the polysaccharides spotted. Neither an underivatized glass surface nor SAM 4A without UV irradiation showed a detectable signal after treatment with anti-α(1,6)dextran antibodies. These results were reproduced in multiple microarray assays. Thus, not only is SAM 4A suitable for use in the high-throughput construction of microarrays, but also the photo-immobilized carbohydrates retain their immunological properties, as defined by a specific antibody, after immobilization. These results show that the invention offers a plausible alternative to nitrocellulose for displaying lighter carbohydrates.

Figure 29C:
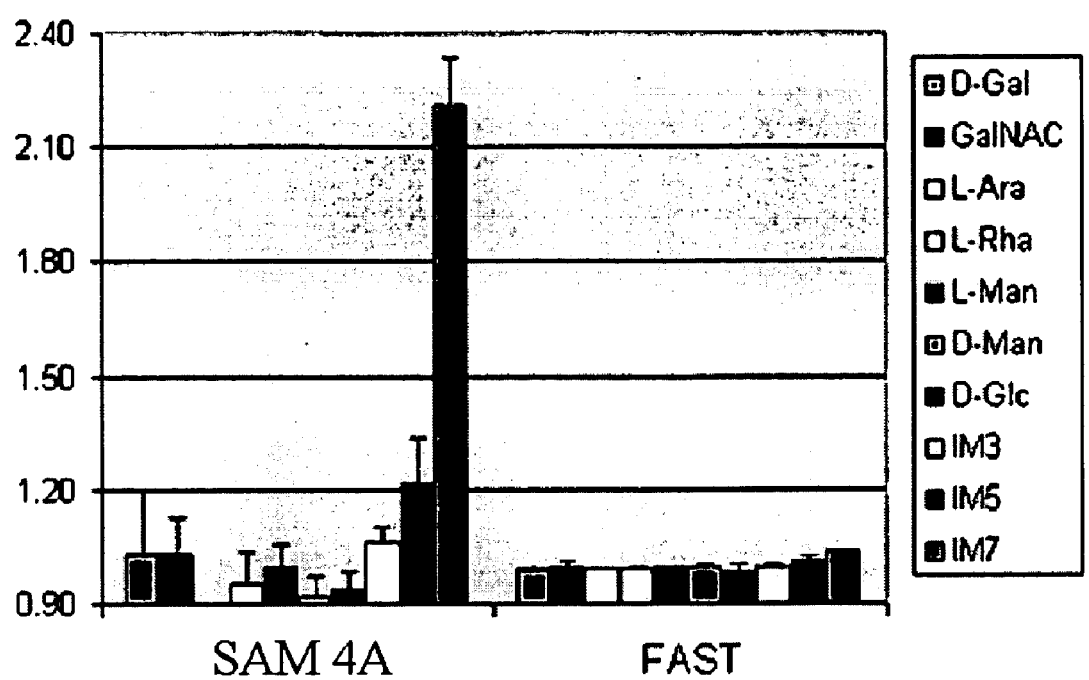
FIG. 29C shows epitope-display of immobilized mono- and oligosaccharides on SAM 4A and FAST surfaces.

A panel of mono- and oligosaccharide arrays on SAM 4A and FAST slides were also studied. The spotted arrays were probed with a biotinylated lectin ConA (see FIG. 29C), which is Man- and/or Glc-specific and requires the C-3, C-4 and C-5 hydroxyl groups of the Man or Glc ring for binding. The results showed that oligosaccharides with three (IM3), five (IM5) and seven glucoses (IM7) are reactive to ConA on the SAM 4A slide but not on the FAST slide. However, none of the spotted mono-saccharides was reactive to the lectin on these surfaces. The method of photo-coupling, which can target any CH—group on the carbohydrate rings with varying specificity depending on the structure of the ring, may interfere significantly with the lectin binding of mono-saccharides, Man or Glc. The limited specificity of the reaction and the lesser amount of carbohydrate epitopes present for smaller carbohydrates reduces the probability that a biologically-active epitope presents itself at the air-monolayer interface.

Figure 30:
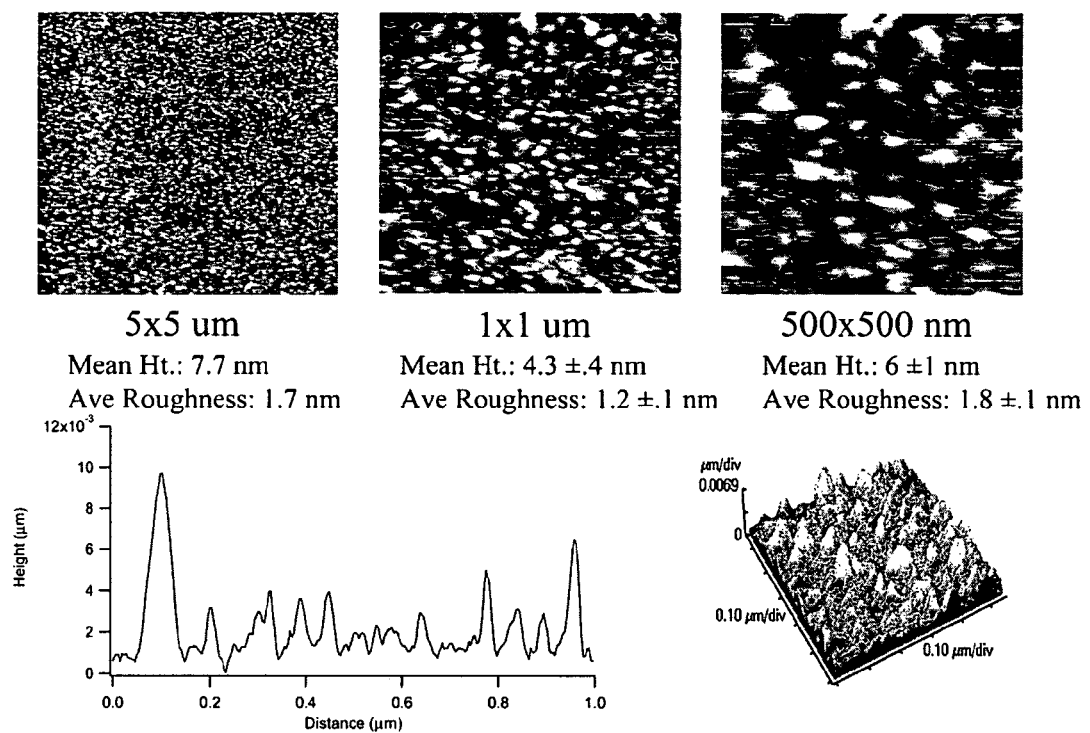
FIG. 30 shows an AFM image of SAM 4B on a substrate.

Mixed monolayers were formed from a solution containing a 20:1 ratio of aminopropyltrimethoxy silane to Compound 4 (SAM 4B). The 20:1 ratio of aminopropyltrimethoxy silane to Compound 4 was mixed in a vial containing anhydrous toluene. A microscope slide was placed in a vial, sealed, and purged with argon. The prepared solution was added into the sealed vial via a syringe and allowed to react overnight. The slide was then removed and rinsed as described above. As shown in FIG. 30, SAM 4B may be in the form of a multilayer rather than a monolayer.

Figures 31A, 31B:
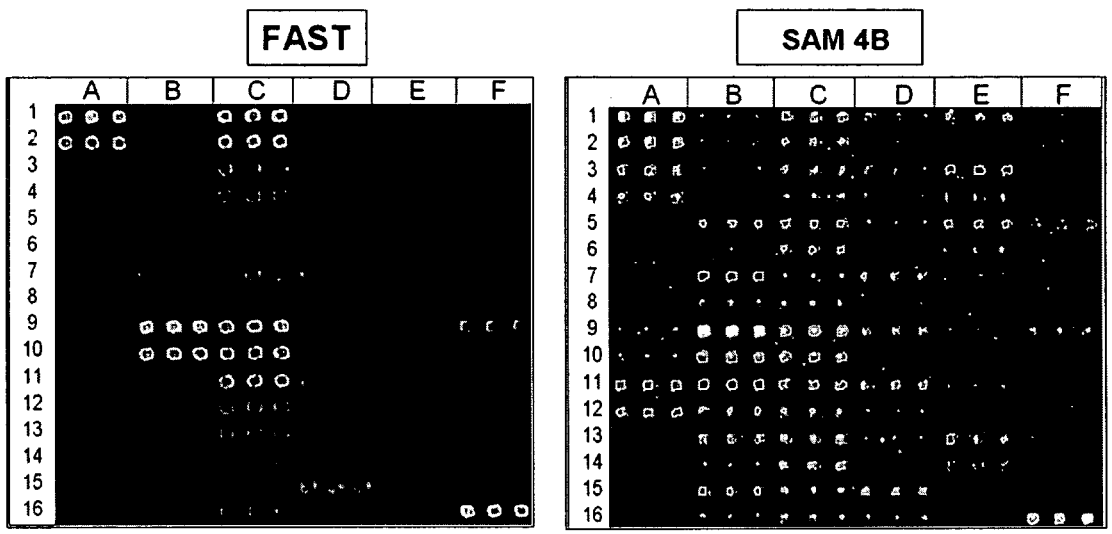
FIGS. 31A and 31B show a comparison of fluorescence emitted from a microarray containing spotted carbohydrates attached to SAM 4B and nitrocellulose coated surfaces (FAST) after depositing a IgG anti-carbohydrate monoclonal antibody.

A FAST slide and a SAM 4B slide were spotted with a panel of carbohydrates (38 total) and protein/peptide (8) preparations, as shown in FIGS. 31A and 31B. The slides were then stained with a preparation of human serum (1:25 dilution). The chip-bound human IgG antibodies were revealed with an anti-human IgG antibodies conjugated with Cy3. The microarray images were captured using ScanArray 5000A microarray scanner. As shown in FIG. 31A, the photo-generated carbohydrates using SAM 4B reveal a broader spectrum of IgG anti-carbohydrate antibodies as compared to the FAST slide.

As shown in FIGS. 31A and 31B, broader spectrum of IgG anti-carbohydrate antibodies were observed with SAM 4B as compared to those prepared on FAST slides.

Example 9

Immobilization of Polymers on Surfaces

Figure 32A:
FIGS. 32A through 32C show OM images of polyvinyl alcohol (PVA), poly(tert-butyl acrylate) (PTBA), and PS immobilized on a surface.
Figure 32B:
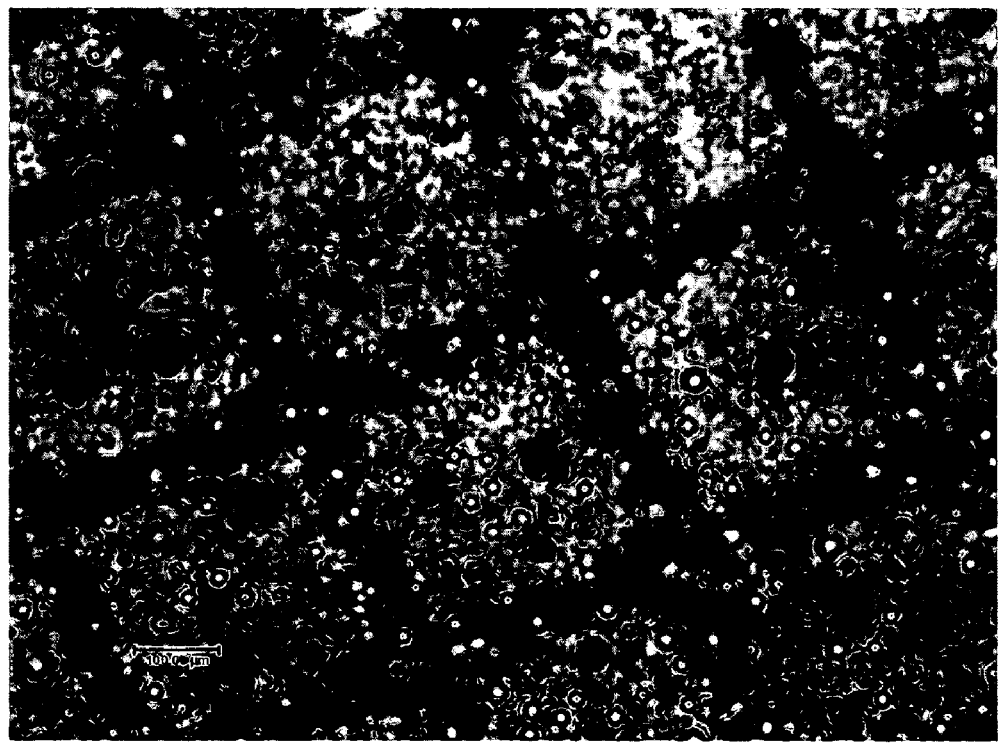
Figure 32C:
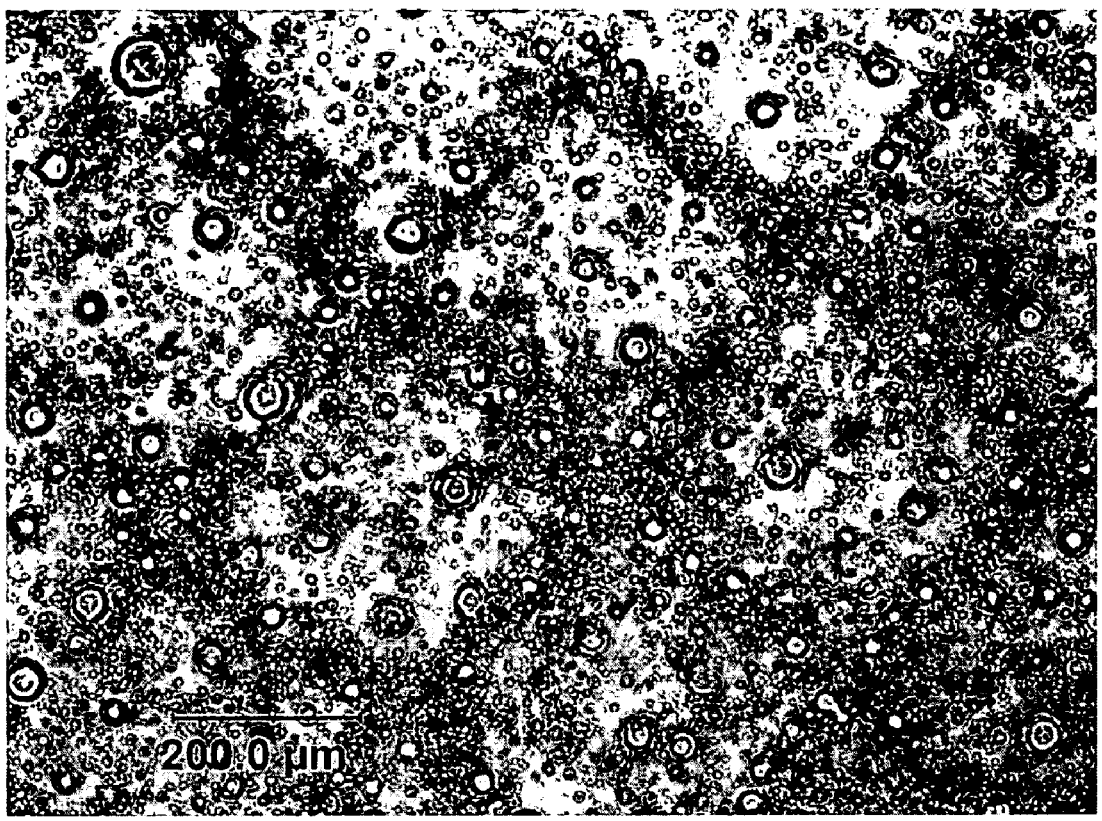

In addition to immobilization of various carbohydrates, variety of polymers were also immobilized and patterned on a surface. PS, poly(tert-butyl acrylate) (PTBA), and poly (vinyl alcohol) PVA were immobilized and patterned on SAM 4. The OM images of the immobilized PVA, PTBA, and PS patterns are shown in FIGS. 32A through 32C, respectively. PVA was imaged by breath condensation. PTBA and PS were imaged by spin coating a mixture of PS and triphenylsuphonium triflate onto the patterned surface.

Figure 33:
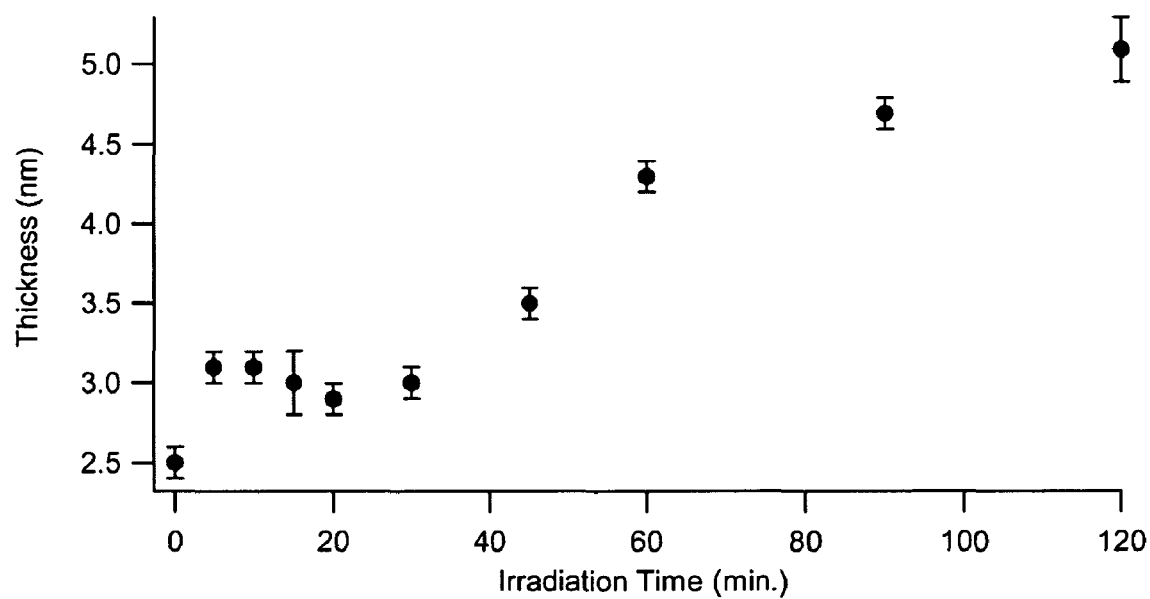
FIG. 33 shows a plot of the thickness of PVA immobilized on a surface as a function of irradiation time after the hot water treatment

To test for the robustness of the immobilized films, surfaces with PVA were irradiated for various time periods to obtain different thicknesses. The surfaces immobilized with PVA were rinsed in hot water after irradiation. The immobilized surfaces were placed in a vial of deionized water and heated to 75° C. for 15 minutes and to 90° C. for 2.5 hours. The deionized water was changed and the surface was rinsed with deionized water. Surfaces were then placed back into a heated water (about 95° C.) for additional three hours. FIG. 33 shows a plot of the thickness as a function of irradiation time after the hot water treatment. As shown, PVA remain immobilized on the surface after heat treatment and exhibit an increase in thickness with increasing irradiation time.

Example 10

Electroless Deposition of Metals

Moreover, electroless deposition of nickel was carried out to selectively deposit nickel on regions immobilized with polyacrylic acid (PAA). A glass surface was coated with SAM 4 and PAA (35 wt % in water) was spin-coated onto SAM 4 as described above. Then, the sample was irradiated through a photomask having lines of varying widths for about 4 to 5 hours. The sample was then rinsed with water and immersed in a aqueous catalyst solution containing 5 mM palladium tetraammonium dichloride for about 30 seconds. The sample was then removed and placed in deionized water for about 30 seconds to rinse off any catalyst that are not on the regions coated with PAA. The sample was then placed in a nickel bath for 15 minutes. The nickel bath contained 4 g of nickel sulfate, 2 g sodium citrate, 1 g of lactic acid, 0.2 g of dimethyl amine borane, and 100 mL of deionized water. The pH of the nickel bath was adjusted to 6.8±0.2 using ammonium hydroxide.

Figure 34:
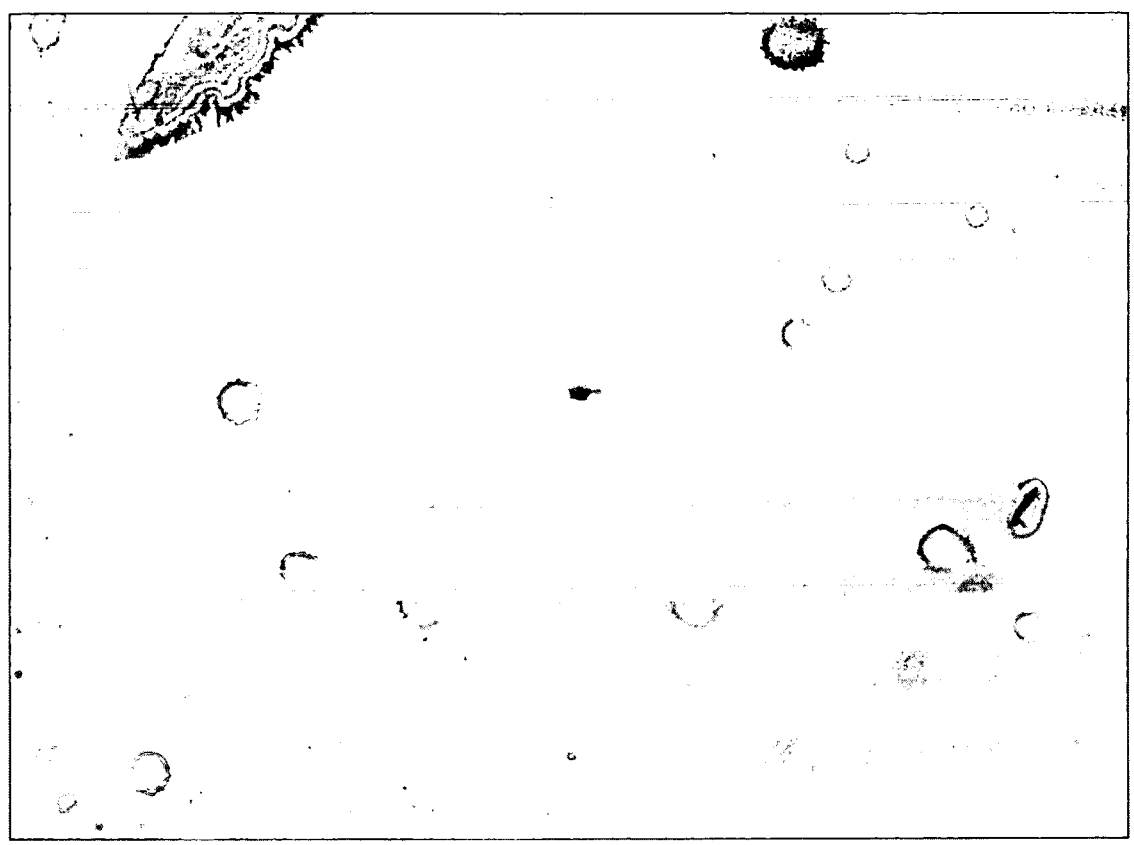
FIG. 34 shows OM image of selective electroless deposition of nickel on PAA immobilized surfaces.

FIG. 34 shows that nickel was selectively deposited onto only the PAA coated regions.

As various changes can be made without departing from the scope and spirit of the invention as described, it is intended that all subject matter contained in the above description, shown in the accompanying drawings, or defined in the appended claims be interpreted as illustrative, and not in a limiting sense.

We claim:

1. A compound of the formula

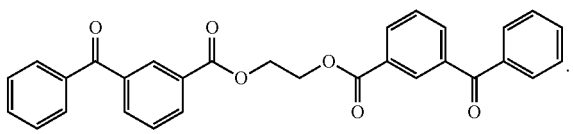

* * * * *